(12) United States Patent
Suerbaum et al.

(10) Patent No.: US 6,838,273 B2
(45) Date of Patent: Jan. 4, 2005

(54) **CLONING AND CHARACTERIZATION OF THE FLBA GENE OF *H. PYLORI*, PRODUCTION OF AFLAGELLATE STRAINS**

(75) Inventors: Sebastian Suerbaum, Bochum (DE); Agnès Labigne, Bures sur Yvette (FR)

(73) Assignee: Institut Pasteur and Institut National de la Sante et de la Recherche Medicale, Paris Cedex (FR)

( * ) Notice: Subject to any disclaimer, the term of this patent is extended or adjusted under 35 U.S.C. 154(b) by 184 days.

(21) Appl. No.: 09/015,078

(22) Filed: Jan. 29, 1998

(65) Prior Publication Data

US 2003/0152579 A1 Aug. 14, 2003

Related U.S. Application Data

(62) Division of application No. 08/671,757, filed on Jun. 28, 1996, now Pat. No. 6,476,213.

(30) Foreign Application Priority Data

Jul. 4, 1995 (FR) .............................. 95 08068

(51) Int. Cl.[7] .............. C12N 1/20; A01N 63/00
(52) U.S. Cl. .................. 435/252.3; 424/93.4
(58) Field of Search ................ 530/300, 350, 530/387.1; 435/7.1, 252.3; 436/500; 424/93.1, 93.2, 93.4

(56) References Cited

FOREIGN PATENT DOCUMENTS

| EP | 0 329 570 A3 | 8/1989 |
|---|---|---|
| FR | 2 669 929 | 6/1992 |
| WO | 93/07273 | 4/1993 |

OTHER PUBLICATIONS

Benjamini, Ed., Immunology: A Short Course, Wiley–Liss, pp. 174–175, 1991.*
Skolnick et al., Trends in Biotech., 18(1):34–39, 2000.*
Lelwala–Guruge et al, Scan. J. of Infect. Dis., 24(4):457–65, 1992.*
Haas et al, Mol. Microbiol., 1993, vol. 8, No. 4, pp. 753–60., 1993.*
Ferrero et al., "Construction of urease deficient mutants of *Helicobacter pylori* by allelic exchange", *Soc. Microb. Ecol. Dis.*, vol. 4(s), No. S1, Oct. 1991, p. s136, Article nA H4–1.
Josenhans et al., "Comparative Ultrastructural and Functional Studies of *Helicobacter pylori* and *Helicobacter mustelae* Flagellin Mutants: Both Flagellin Subunits, FlaA and FlaB, Are Necessary for full Motility in *Helicobacter* Species", *J. Bacteriology*, vol. 177, No. 1, Jun. 1996, pp. 3010–3020.
Miller et al., "A *Campylobacter jejuni* Homolog of the LcrD/FlbF Family of Proteins Is Necessary For Flagellar Biogenesis", *Infect. Immun.*, vol. 61, No. 71, Jul. 1993, pp. 2930–2936.
O'Toole et al., "Non–motile mutants of *Helicobacter pylori* and *Helicobacter mustelae* defective in flagellar hook production," *Mol. Micro.*, vol. 14, No. 4, 1994, pp. 691–703.
Ramakrishnan et al., "The Cell Cycle–Regulated Flagellar Gene flbF of *Caulobacter crescentus* is Homologous to a Virulence Locus (lcrD) of *Yersinia petis*", *J. Bacteriol.*, vol. 173, No. 22, Nov. 1991, pp. 7283–7292.
Suerbaum et al., "Cloning, Sequencing and Mutagenesis of the *H. pylori* flbA Gene—a Homolog of The lcrD/flbF/invA Family of Genes Associated with Motility and Virulence", *Am. J. Gastroenterol.*, vol. 89, No. 8, Aug. 1994, p. 1331, Article nA 185.
Suerbaum et al., "Cloning, Expression and Mutagenesis of the *H. pylori* flbA Gene—a Homolog of The lcrD/flbF Family of Genes Associated with Motility and Virulence", Abstracts of 95th General Meeting for American Society of Microbiology, May 21–25, 1995, p. 181, Article nA B–93.

\* cited by examiner

*Primary Examiner*—Gary Kunz
*Assistant Examiner*—Sharon Turner
(74) *Attorney, Agent, or Firm*—Finnegan, Henderson, Farabow, Garrett & Dunner, LLP

(57) ABSTRACT

The present application relates to nucleotide sequences which regulate the biosynthesis of the flagella proteins *Helicobacter pylori*, to the proteins encoded by these sequences and to aflagellate bacterial strains. The invention also relates to the use of these means for detecting an infection due to *H.pylori* or for protecting against such an infection.

22 Claims, 22 Drawing Sheets

Figure 1A:
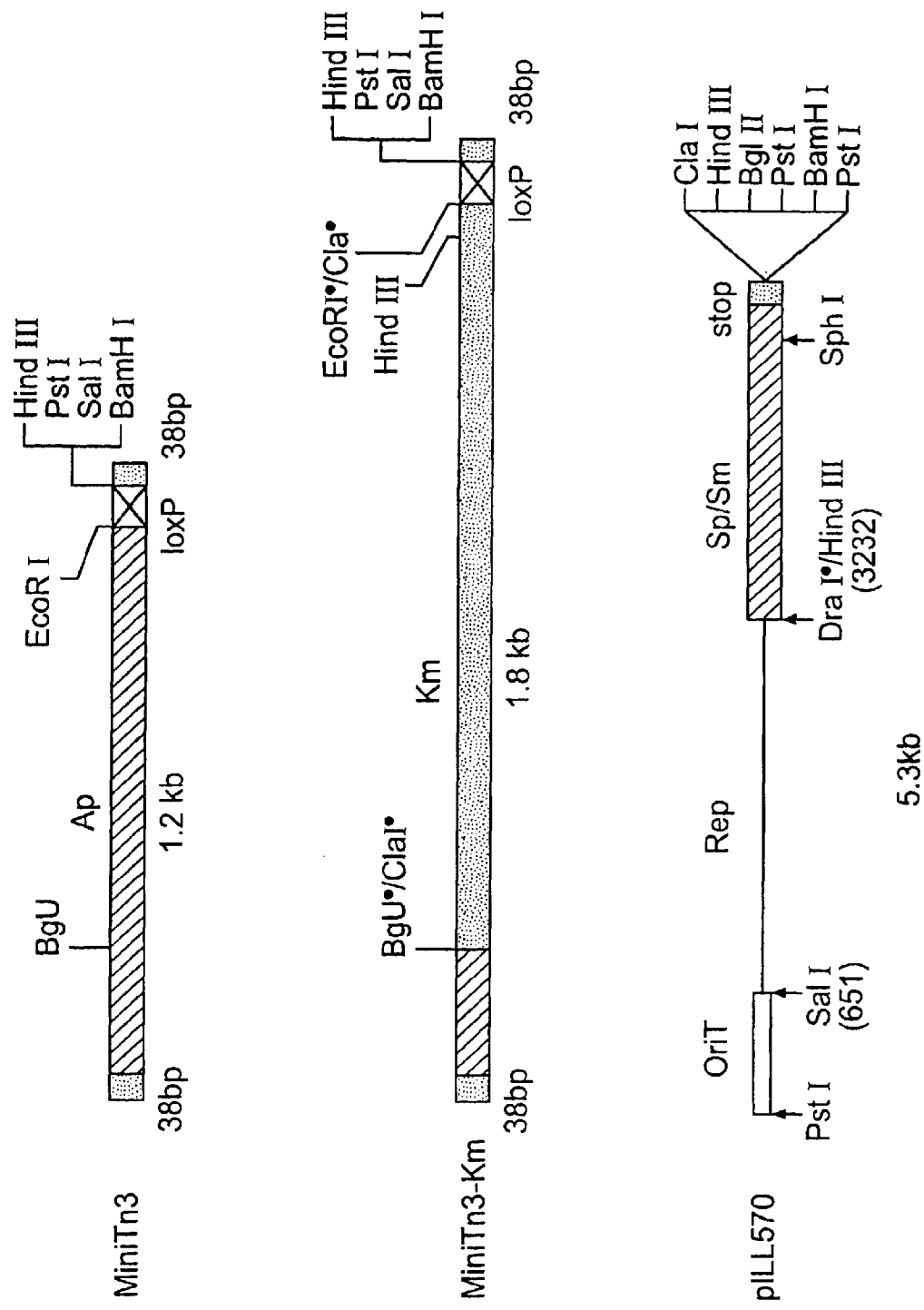

```
  1 AGC TTT TTT GTG CCA TAC TTT TAA ACT TTA TAT AAT AAG AGA CAA ACA CAC CTA CCA

61 AAA TTA AGG CAT TGA TTT TAG ATT ATG GCA AAC GAA CGC TCC AAA TTA GCT TTT AAA AAG
                                     M   A   N   E   R   S   K   L   A   F   K   K

121 ACT TTC CCT GTC TTT AAA CGC TTC TTG CAA TCC AAA GAC TTA GCC CTT GTC GTC TTT GTG
     T   F   P   V   F   K   R   F   L   Q   S   K   D   L   A   L   V   V   F   V

181 ATA GCG ATT TTA GCG ATC ATT ATT GTG CCG CCT TTT GTG TTG GAT TTT GAT TTT TTA CTC
     I   A   I   L   A   I   I   I   V   P   P   F   V   L   D   F   D   F   L   L

241 ACG ATT TCT ATC GCG CTA TCG ACT TTA TTA ATT GGG CTT TAT ATT GAC AAA CCG
     T   I   S   I   A   L   S   T   L   L   I   G   L   Y   I   D   K   P

301 ACT GAT TTT AGC GCT TTC CCC ACT AGA ATG ATT TTA ACC TTA TAC CGC TTG GCT TTA
     T   D   F   S   A   F   P   T   R   M   I   L   T   L   Y   R   L   A   L

361 AAT GTC GCC ACC ACT GCG TTT GGG GAA TTT CAA GGC TAT AAA GGG CCT AGC GCG GTG AGC
     N   V   A   T   T   A   F   G   E   F   Q   G   Y   K   G   P   S   A   V   S

421 ATT ATC ACG GCG TTT GGG AAT TAT GTG AGC GGG AAT TAT GTG ATT GGG GCT ATT
     I   I   T   A   F   G   N   Y   V   S   G   N   Y   V   I   G   A   I
```

FIG. 2A

FIG. 2B

```
481 ATC TTT AGT ATT TTA GTG CTG GTG AAT TTA GTT ACT AAT GGT TCT ACT AGG GTT
     I   F   S   I   L   V   L   V   N   L   V   T   N   G   S   T   R   V
                                           511
541 ACT GAA GTT AGG GCG CGA TTT GCC CTA GAC ATG GTT CCA GGA AAG CAA ATG GCG ATT GAT
     T   E   V   R   A   R   F   A   L   D   M   V   P   G   K   Q   M   A   I   D
                                           571
601 GCG GAT TTA AAT TCA GGG CTT ATT GAT GAT AAG GAA GCT AAA AAA CGG CGC GCC GCT CTA
     A   D   L   N   S   G   L   I   D   D   K   E   A   K   K   R   R   A   A   L
                                           631
661 AGC CAA GAA GCG TCT ATC ATT TAT GGT GCG ATG GAT GGC GCG TCT AAA TTT GTC AAA GGC GAT
     S   Q   E   A   S   I   I   Y   G   A   M   D   G   A   S   K   F   V   K   G   D
                                           691
721 GCG ATC GCT TCT ATC ATC ATT ACG CTT ATC AAT ATC ATT ATT GGG GGT TTA GTG GTG GGC GTG
     A   I   A   S   I   I   I   T   L   I   N   I   I   I   G   G   L   V   V   G   V
                                           751
781 TTC CAA AGG GAT ATG AGC TTG AGC TTT AGT ATT GCT ACT TTC ACT AGC ACT ATT GCG ATT GGC
     F   Q   R   D   M   S   L   S   F   S   I   A   T   F   T   S   T   I   A   I   G
                                           811
841 GAT GGG CTT GTA GGG CAA ATC CCT GCC TTA GCT CTT ATC ACA CGG ACC GGT ATT GTC GCC
     D   G   L   V   G   Q   I   P   A   L   A   L   I   T   R   T   G   I   V   A
                                           871
901 ACT CGC ACC ACG CAA AAC GAA GAA GAG GAC TTT GCT TCT AAG CTC ATC ACA CAG CTC ACC
     T   R   T   T   Q   N   E   E   E   D   F   A   S   K   L   I   T   Q   L   T
                                           931
```

```
 961 AAT AAA AGC AAA ACT TTA GTG ATT GTG GGG ATT TAT TGC ACC ATT CCT GGA
     N   K   S   K   T   L   V   I   V   G   I   Y   C   T   I   P   G
1021 CTC CCT ACC TTT TCT TTA GCG TTT GTA GGG TTT TTA TGC ATC TGG CTG ATT
     L   P   T   F   S   L   A   F   V   G   F   L   C   I   W   L   I
1081 AGC AGG GAG GGA AAG GAC GGG TTG CTC ACT CTC GAA AAT TAT TTG AGT CAA AAA TTC
     S   R   E   G   K   D   G   L   L   T   L   E   N   Y   L   S   Q   K   F
1141 GGC TTG GAT TTG AGC GAA AAA GAG ATT AAA CCC CAC AGC AAA ATC CCC ACC ACA
     G   L   D   L   S   E   K   E   I   K   P   H   S   K   I   P   T   T
1201 AGG GCT AAA ACC CAA GAA GAA TTA GCT TTG GCT TCC AAA AGA GAA GAG CAA GAG ATT GAT GAA GTG TTA
     R   A   K   T   Q   E   E   L   A   L   A   S   K   R   E   E   Q   E   I   D   E   V   L
1261 AAA ATT GAA TTT CTT GAA TTA TTA GAA AGG ATT AGG GCT TTA TAT CAG CTC TAC AGC TTA GCG GAC ATG AAA
     K   I   E   F   L   E   L   L   E   R   I   R   A   L   Y   Q   L   Y   S   L   A   D   M   K
1321 CAA GGG GGC GAT TTG ATG CCT CAA ATT AGG ATT AGG GGT ATT AGA AAA ATA GCG AGC GAC ATG TAT
     Q   G   G   D   L   M   P   Q   I   R   I   R   G   I   R   K   I   A   S   D   M   Y
1381 GGT TTT TTG ATG CCT CAA ATT AGG ATT AGG ATT AGG GAT AAT TTA CAA CTC CCC CCA ACG CAT TAT
     G   F   L   M   P   Q   I   R   I   R   I   R   D   N   L   Q   L   P   P   T   H   Y
```

*FIG. 2C*

FIG. 2D

```
1441
GAA ATC AAG CTT AAG GGC ATT GTG ATT GGT GAA GGC ATG GTG ATG CCG GAT AAG TTT TTA
 E   I   K   L   K   G   I   V   I   G   E   G   M   V   M   P   D   K   F   L
1501
GCC ATG AAT ACC GGT TTT GTG AAT AAA GAA ATT GAA GGC ATT CCT ACT AAA GAG CCG GCT
 A   M   N   T   G   F   V   N   K   E   I   E   G   I   P   T   K   E   P   A
1561
TTT GGA ATG GAC GCT TTA TGG ATT GAA ACT AAA AAT AAA GAA GAA GCC ATC ATT CAA GGC
 F   G   M   D   A   L   W   I   E   T   K   N   K   E   E   A   I   I   Q   G
1621
TAT ACC ATT ATT GAT CCA AGC ACC GTT ATT GCG ACG CAC ACC AGC TTA GAA TTA GTG AAA
 Y   T   I   I   D   P   S   T   V   I   A   T   H   T   S   L   E   L   V   K
1681
TAC GCT GAA GAT TTT ATC ACT AAA GAT GAA AGT AAA GTG AAA TCC CTT TTA GAG CGC TTG GCC AAA
 Y   A   E   D   F   I   T   K   D   E   S   K   V   K   S   L   L   E   R   L   A   K
1741/581
GAC TAT CCT ACG ATT GTA GAA GAG AAA ATC CCC ACC GGT GCG ATC CGA TCA GTC
 D   Y   P   T   I   V   E   E   K   I   P   T   G   A   I   R   S   V
1801
TTG CAA GCC TTG CAT GAA AAA ATT AAA GAC ATG CTC ACT ATT TTA GAA ACG
 L   Q   A   L   H   E   K   I   K   D   M   L   T   I   L   E   T
1861
ATT ACC GAT ATT GCG CCA TTA GTT CAA AAC GAT GTG AAT ATC TTA ACC GAA CAA GTG AGG
 I   T   D   I   A   P   L   V   Q   N   D   V   N   I   L   T   E   Q   V   R
1891
```

```
1921
GCG AGG CTT TCT AGG GTG ATC ACT AAC GCT TCT AAA TCT GAA GAC GGG CGT TTG AAA TTT
 A   R   L   S   R   V   I   T   N   A   S   K   E   D   G   R   L   K   F
1981                                                   1951
TTA ACC TTT TCT AGC CTA CTA ACC GAT AGC CAA TTT CTT AAT AAA TTG CGA GAA AAT GGC ACT
 L   T   F   S   S   L   L   T   D   S   Q   F   L   N   K   L   R   E   N   G   T
2041                                                   2011
TCT AAG AGC ATG AAA GCC CTA GTC CTC TCT AAT CAA TTT CAA GGC GAA ATT CTC ATT GAG TCT GAA
 S   K   S   M   K   A   L   V   L   S   N   Q   F   Q   G   E   I   L   I   E   S   E
2101                                                   2071
GAG GCC ATG AAA GCC CTA GTC CTC TCT AAT CAA TTT CAA GGC GAA ATT CTC ATT GAG TCT GAA
```

```
  1 MANKRS-KLAFKKTFPVEKRFLQSKDLALVVEVIAILAIIVPLPPFVLDFLLTISIALS  HpFlbA
  1 MAKNKIVDLVFPFLGPLIAPVLKAKSLTIVGFLVCILAIIIVPLPSPILDFFLALSIALS CjFlbA
  1 MADAAAPNASSMPSAKSLLDGLMRGEMGLALGVVGIIVLLIIPVPAPLLDVLLAISLTGS CcFlbF
  1 -------MNPHDLEWLNRIGERKDIMLAVLLAVVFMMVLPLPPLVLDILIAVNMTIS    YpLcrD
  1 ---------MLLSLLNSARLRPRLLILVLMVMIISMFVIPLPTYLVDFLIALNIVLA    StInvA
  1 -------------------------------MVMIIAMLIIPLPLPTYLVDFLIGLNIVLA SfMxiA
                                          *.*    ..*    *:

60 VLILIGLYIDKPTDFESAFPTLLLIVTLYRLALNVATTRMILTQGYKGPSAVSIIITAFG  HpFlbA
 61 VLILISIYIPKPTDLTFPTLILITLFRLSLNIATTRMILSEGQNGPEAVSEIIAAFG    CjFlbA
 61 VLILMTAILIKKPLEFTSFPTVLLVTLFRLGLNIASTRLILSHGQEGTGGAVIEAFG    CcFlbF
 52 VVLLMIAIYINSPLQFSAFPAVLLVTTLFRLALSVSTTRMILLQ-----ADAGQIVYTFG YpLcrD
 49 ILVFMGSFYIDRILSFSTFPAVLLITTLFRLALSISTSRLLIEA------DAGEIIATFG StInvA
 29 ILVFMGSFYIERILSFSTFPSVLLITTLFRLALSISTSRLILVDADRGK-----IITTFG SfMxiA
          *   .  :* .:*::::**::: ::::**.*.:  .            * **

120 EFSVSGNYVIGAIIFSILVLVNLLVVTNGSTRVTEVRARFALDAMPGKQMAIDADLNSGL HpFlbA
121 EFVVGGNMVIGVIVFCILVLINFMVVTKGSTRVSEVQARFTLDAMPGKQMAIDADLNAGL CjFlbA
121 HLMMQGNFVIGIVFEIILVVNFMVTKGSGRIAEVAARFTLDSMPGKQMAIDADLSTGL   CcFlbF
107 NFVVGGNLIVGIVIFLIITIVQFLVITKGSERVAEVSARFSLDAMPGKOMSIDGDMRAGV YpLcrD
104 QFVIGDSLAVGFVVESIVTVVVQFIVITKGSERVAEVAARFSLDGMPGKQMSIDADLKAGI StInvA
 84 QFVIGDSLAVGFVIFSIVTVVQFIVITKGSERVAEVAARFSLDGMPGKQMSIDADLKAGI SfMxiA
       .  :*.:   :: :: .::: *:* *  :.** **:**.****:*:* :
```

FIG. 3A

```
180 IDDKEAKKRRAALSQEADFYGAMDGASKFVKGDAIASIIITLINIIGGFLVGVFQRDMSL    HpFlbA
181 IDEQTARARRQEVIAEANFYGAMDGSSKFIKGDAVAGIIITIINIIGGFLIGSFQHDMAL    CjFlbA
181 ISQDEAKIRRKELEQESTFFGAMDGASKFVKGDAIAGLIITAINIIGGIIIGVVQHKMPF    CcFlbF
167 IDVNEARERRATIEKESQMFGSMDGAMKFVKGDAIAGLIIIFVNILGGVTIGVTQKGLAA    YpLcrD
164 IDADAARERRSVLERESQLYGSFDGAMKFIKGDAIAGIIIFVNFIGGISVGMTRHGMDL    StInvA
144 IDAAGAKERRSILERESQLYGSFDGAMKFIKGDAIAGIIIFVNLIGGISVGMSQHGMSL    SfMxiA
        *   **    *      ** ** *****  ** **  ..** * .   .

240 SFSASTFTILTIGDGLVGQIPALIIATRTGIVATRTTQNEEEDFASKLITQLTNKSKTLV    HpFlbA
241 SDAASTYTILTIGDGLVSQIPGLITSTATAIIITRASKDEENFAEGTLTQLLSEYRTLLI    CjFlbA
241 GDAASTYTIMTIGDGLVSQIPALIISIAAGMVVSKAGVEGSADKALTTQLAMNPVGLGMV    CcFlbF
227 AEALQLYSILTVGDGMVSQVPALLIAITAGIIVTRVSSEDSSDLGSDIGKQVVAQPKAML    YpLcrD
224 SSALSTYTMLTIGDGLVAQIPALLIAISAGFIVTRVNGDTDN-MGRNIMTQLLNNPFVLV    StInvA
204 SGALSTYTILTIGDGLVSQIPALLISISAGFMLTRVNGDSDN-MGRNIMSQIFGNPFVLI    SfMxiA
       . *.  *.****.*.**  ** .   * .   .       . . . .  .

300 IVGAIYC-FCTIPGLPTFSLAFVGALFLFIAWLISREGKDGLLTKLENYLSQKFGLDLSE    HpFlbA
301 VGFVLFI-FALVPGLPTLSLGFMALVFLSLGYLTKQVKEGKI----DITTVKKSKPSAA    CjFlbA
301 SASSG-I-IALIPGMPIFPFAAMALA-----------------------AGALAY    CcFlbF
287 IGGVLLLLFGLIPGFPTVTFLILALLVGCGGYMLSRKQSRNDEANQDLQSILTSGSGAPA    YpLcrD
283 VTAILTISMGTLPGFPLPVFVILSVVLSVLFYFKFREAKRSAAKPKTSKGEQPLSIEEKE    StInvA
263 VTSALALAIGMLPGFPFVFFLIAVTLTALFYKKVVEKEKSLSESDSSGYTG------    SfMxiA
     *    **
```

*FIG. 3B*

```
359 KPHSSKIKPHAPTTRAKTQEEIKREEEQAIDEVLKIEFLELALGYQLYSLADMKQGGDLL  HpFlbA
355 VASQSGAGGTTAAPAKKSEEEILKEEEHKINDILKVEILELELGYGLIKLAE----NELT  CjFlbA
331 KRVQDAKKPKALDPADLEAAAPSEPEEEPISASLAIDDVKIELGYGLLTLINDLDGRKLT  CcFlbF
347 ARTKAKTSGANKGRLGEQEAFAMTVPLLIDVDS-------------SQQEALEANALN   YpLcrD
343 GSSLGLIGDLDKVSTE--------------------------TVPLILLVPKSRREDLEKA  StInvA
316 ----------------TFEDIDNTHDSSLAMIENLDRISSETVPLILLFAENKINANDME  SfMxiA
                                       *                      *

419 ERIRGIRKKIASDYGFLMPQIRIRDNLQLPPTHYEIKLKGIVIGPGMVMPDKFLAMNTGF  HpFlbA
411 ERIRSMRRSIAESLGFLMPKIRIRDNLRLKPNEYSFKLKGVSIASAEIYPDKYLAMDSGF  CjFlbA
391 DQIRALRKTLASEYGFVMPPVRILDNMRLANQGYAIRIKEMEAGAGEVRLGCLMCMDPRG  CcFlbF
392 DELVRVRRALYLDLGVPFPGIHLRFNEGMGEGEYIISLQEVPVARGELKAGYLLVRESVS  YpLcrD
378 QLAERLRSQFFIDYGVRLPEVLLRDGEGLDDNSIVLLINEIRVEQFTVYFD--LMRVVNY  StInvA
359 GLIERIRSQFFIDYGVRLPTILYRTSNELKVDDIVLLINEVRADSFNIYFDKVCITDENG  SfMxiA
           *          *    .   . .  .    :      :  .

479 VNKEIEGIPTKEPAF--GMDALWIETKNKEEAIIQGYTIIDPSTVIATHTSELVKKYAED  HpFlbA
471 ITEEIEGIATKEPAF--NSDALWIDANLKDEATLNGYIVIDPASVISTHMSELIKAHASE  CjFlbA
451 GOVELPGEHVREPAF--GLPATWIADDLREEATFRGYTVVDPATVLTTHLTEILKENMAD  CcFlbF
452 QLELLGIPYEKGEHLLPDQEAFWVSVEYEERLEKSQLEFFSHSQVLTWHLSHVLREYAED  YpLcrD
436 SDEVVSFGINPTIHQQGSSQYFWVTHEEGEKLRELGYVLRNALDELYHCLAVTVARNVNE  StInvA
419 DIDALGIPVVSTS--YNERVISWDVSYTENLTNIDAKIKSAQDEFYHQLSQALLNNINE  SfMxiA
           *                  .     .
```

FIG. 3C

```
537 FITKDEVKSLLERLAKDYPTIVEESK-KI-PTGAIRSVLQALLHEKIPIKDMLTILETIT  HpFlbA
529 LLTRQEVQNLLDKVKNDYPIIVEGAL-GVAPVSLIQKILKDLLKHHIPIKDMLTILESVS  CjFlbA
509 LLSYAEVQKLLKELPETQKKLVDDLIPGTVTATTVQRVLQSLLRERVSIRDLPQILEGVG  CcFlbF
512 FIGIQETRYLLEQMEGGYGELIKEVQR-IVPLQRMTEILQRLVGEDISIRNMRSILEAMV  YpLcrD
496 YFGIQETKHMLDQLEAKFPDLLKEVLRH-ATVQRISEVLQRLLSERVSVRNMKLIMEALA  StInvA
477 IFGIQETKNMLDQFENRYPDLLKEVFRHV-TIQRISEVLQRLLGENISVRNLKLIMESLA  SfMxiA
                *                    *                   *       *

595 DIAPLVQNDVNILTEQVRARLSRVITNAPKSEDGRLKFLTFSTDSEQFLLNKLRENGTSK  HpFlbA
588 DIAR-VSKSFDMIEKVRASLARMITNMYLDDKGNLDIFILDSASSAVLMENVQFRDGSY  CjFlbA
569 EAAPHTA-SVTQLVEQVRARLARQLCWANRGDDGALPIITLSADWEQAFAEALIGPGDDK  CcFlbF
571 EWGQK-EKDVVQLTEYIRSSLKRYICYKYANGNNILPAYLFDQEVEEKIRSGVRQTSAGS  YpLcrD
555 LWAPR-EKDVINLVEHIRGAMARYICHKF-ANGGELRAVMVSAEVEDVIRKGIRQTSGST  StInvA
536 LWAPR-EKDVITLVEHVRASLSRYICSK-IAVSGEIKVVMLSGYIEDAIRKGIRQTSGGS  SfMxiA
         *                                *                   *

655 SLLLNVGELQKLIFAVSEEAMKVLQKGIAPVILIVEPNLRKALSNQMEQARIDVIVLSHA  HpFlbA
647 HLPLSVAQTGTLVDTLRAEVAVANGRIKPFILCVEPQLRKFIADICYNFSINIVVLSFA  CjFlbA
628 QLALPPSRLQDFIRGVRDSFERAALAGEAPVLL-TSPGVRPYVRSIIERFRGQTVVMSQN  CcFlbF
630 YLALEPAVTESLLEQVRKTIGDLSQIQSKP-VLIVSMDIRRYVRKLIESEYYGLPVLSYQ  YpLcrD
613 FLSLDPFASANLMDLITLKLDDLLIAH-KDLVLLTSVDVRRFIKKMIEGRFPDLEVLSFG  StInvA
594 FLNMDIEVSDEVMETLAHALREL-RNAKKNFVLLVSVDIRRFVKRLIDNRFEKSILVISYA  SfMxiA
                                              *

715 ELDPNSNFEEALGTIHINF                                           HpFlbA
707 EIAENTNFNTEGIIRIEL                                            CjFlbA
687 EIHPRARLKTVGMV---                                             CcFlbF
689 ELTQQINIQPLGRICL--                                            YpLcrD
672 EIADSKSVNVIKTI---                                             StInvA
653 EIDEAYTINVLKTI---                                             SfMxiA
```

FIG. 3D

| TYPE OF EXTRACT | DO @ 750nm | CONCENTRATION IN mg/ml |
|---|---|---|
| GLYCINE (AFTER CENTRIFUGATION FOR 15 min @ 3000 g) | 0.028 | 0.284 |
| N-OCTYL-GLYCOSIDE | 0.087 | 1.004 |
| SUPERNATANT 1 (AFTER 1ST PBS WASHING) | 0.059 | 0.844 |
| SUPERNATANT 2 (AFTER 2nd PBS WASHING) | 0.015 | 0.1105 |

| TYPE OF EXTRACT | DO @ 760 nm | CONCENTRATION IN µg/ml |
|---|---|---|
| GLYCINE (AFTER CENTRIFUGATION FOR 15min @ 3000g) | 0.279 | 202.86 |
| N-OCTYL-GLUCOSIDE | 0.243 | 873.99 |
| SUPERNATANT 1 (AFTER 1ST PBS WASHING) | 0.361 | 539.2 |
| SUPERNATANT 2 (AFTER 2ND PBS WASHING) | 0.218 | 77.875 |

| TYPE OF EXTRACT | DO @ 760 nm | CONCENTRATION IN µg/ml |
|---|---|---|
| GLYCINE RESIDUE (AFTER 15 min OF CENTRIFUGATION AT 3000g) | 0.099 | 297.5 |
| GLYCINE RESIDUE (AFTER EXTRACTION) | 0.093 | 2778.7 |
| N-OCTYL-GLUCOSIDE (AFTER EXTRACTION) | 0.275 | 972.0 |

*FIG. 13B*

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

ATGCCNGGNA AAGCARATG                                                19

(2) INFORMATION FOR SEQ ID NO: 2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

RAAYTTCATN GCNCCRTC                                                18

(2) INFORMATION FOR SEQ ID NO: 3:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

ATGCCAGGAA AGCAAATGGC GATTGATGCG GATTTAAATT CAGGGCTTAT TGATGATAAG    60

GAAGCTAAAA AACGGCGCGC CGCTCTAAGC CAAGAAGCGG ATTTTTATGG TGCGATGGAT    120

GGCGCGTCTA AATTT    135

(2) INFORMATION FOR SEQ ID NO: 4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

-continued

```
CGGGATCCGT GGTTACTAAT GGTTCTAC                                   28

(2) INFORMATION FOR SEQ ID NO: 5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

CGGGATCCTC ATGGCCTCTT CAGAGACC                                   28

(2) INFORMATION FOR SEQ ID NO: 6:

(i) SEQUENCE CHARACTERISTICS:
        (A) LENGTH: 2501 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

AGCTTTTTTG TGCCATACTT TTAAACTTTA TATTATAATA AGAGACAAAC ACACCTACCA    60

AAATTAAGGC ATTGATTTTA GATTATGGCA AACGAACGCT CCAAATTAGC TTTTAAAAAG   120

ACTTTCCCTG TCTTTAAACG CTTCTTGCAA TCCAAAGACT TAGCCCTTGT GGTCTTTGTG   180

ATAGCGATTT TAGCGATCAT TATCGTGCCG TTACCGCCTT TTGTGTTGGA TTTTTTACTC   240

ACGATTTCTA TCGCGCTATC GGTGTTGATT ATTTTAATCG GCTTTATAT TGACAAACCG    300

ACTGATTTTA GCGCTTTCCC CACTTTATTA CTCATTGTAA CCTTATACCG CTTGGCTTTA   360

AATGTCGCCA CCACTAGAAT GATTTTAACC CAAGGCTATA AAGGGCCTAG CGCGGTGAGC   420

ATTATTATCA CGGCGTTTGG GGAATTTAGC GTGAGCGGGA ATTATGTGAT TGGGGCTATT   480

ATCTTTAGTA TTTTAGTGCT GGTGAATTTA TTAGTGGTTA CTAATGGTTC TACTAGGGTT   540

ACTGAAGTTA GGGCGCGATT TGCCCTAGAC GCTATGCCAG AAAGCAAAT GGCGATTGAT    600

GCGGATTTAA ATTCAGGGCT TATTGATGAT AAGGAAGCTA AAAAACGGCG CGCCGCTCTA   660

AGCCAAGAAG CGGATTTTTA TGGTGCGATG GATGGCGCGT CTAAATTTGT CAAAGGCGAT   720

GCGATCGCTT CTATCATTAT CACGCTTATC AATATCATTG GGGTTTTTT AGTGGGCGTG    780

TTCCAAAGGG ATATGAGCTT GAGCTTTAGT GCTAGCACTT TCACTATCTT AACCATTGGC   840

GATGGGCTTG TAGGGCAAAT CCCTGCCTTA ATCATTGCGA CACGGACCGG TATTGTCGCC   900

ACTCGCACCA CGCAAAACGA AGAAGAGGAC TTTGCTTCTA AGCTCATCAC ACAGCTCACC   960

AATAAAAGCA AAACTTTAGT GATTGTGGGG GCGATTTATT GCTTTTGCAC CATTCCTGGA  1020

CTCCCTACCT TTTCTTTAGC GTTTGTAGGG CTCTCTTTTT TATTCATCGC ATGGCTGATT  1080

AGCAGGGAGG GAAAGGACGG GTTGCTCACT AAATTAGAAA ATTATTTGAG TCAAAAATTC  1140

GGCTTGGATT TGAGCGAAAA ACCCCACAGC TCCAAAATCA AACCCCACGC CCCCACCACA  1200

AGGGCTAAAA CCCAAGAAGA GATTAAAAGA GAAGAAGAGC AAGCCATTGA TGAAGTGTTA  1260

AAAATTGAAT TTTTAGAATT GGCTTTAGGC TATCAGCTCT ACAGCTTAGC GGACATGAAA  1320

CAAGGGGGCG ATTTGTTAGA AAGGATTAGG GGTATTAGAA AAAAGATAGC GAGCGATTAT  1380

GGTTTTTTGA TGCCTCAAAT TAGGATTAGG GATAATTTAC AACTCCCCCC AACGCATTAT  1440

GAAATCAAGC TTAAGGGCAT TGTGATTGGT GAAGGCATGG TGATGCCGGA TAAGTTTTA   1500
```

-continued

```
GCCATGAATA CCGGTTTTGT GAATAAAGAA ATTGAAGGCA TTCCTACTAA AGAGCCGGCT   1560

TTTGGAATGG ACGCTTTATG GATTGAAACT AAAAATAAAG AAGAAGCCAT CATTCAAGGC   1620

TATACCATTA TTGATCCAAG CACCGTTATT GCGACGCACA CCAGCGAATT AGTGAAAAAA   1680

TACGCTGAAG ATTTTATCAC TAAAGATGAA GTGAAATCCC TTTTAGAGCG CTTGGCCAAA   1740

GACTATCCTA CGATTGTAGA AGAGAGTAAA AAAATCCCCA CCGGTGCGAT CCGATCAGTC   1800

TTGCAAGCCT TGTTGCATGA AAAAATCCCC ATTAAAGACA TGCTCACTAT TTTAGAAACG   1860

ATTACCGATA TTGCGCCATT AGTTCAAAAC GATGTGAATA TCTTAACCGA ACAAGTGAGG   1920

GCGAGGCTTT CTAGGGTGAT CACTAACGCT TTTAAATCTG AAGACGGGCG TTTGAAATTT   1980

TTAACCTTTT CTACCGATAG CGAACAATTT TTGCTTAATA AATTGCGAGA AAATGGCACT   2040

TCTAAGAGCC TACTACTCAA TGTGGGCGAA TTGCAAAAAC TCATTGAAGC GGTCTCTGAA   2100

GAGGCCATGA AGTCTTGCA AAAGGGATC GCTCCGGTGA TTTTGATCGT AGAGCCTAAT   2160

TTAAGAAAAG CCCTTTCTAA TCAAATGGAG CAGGCTAGGA TTGATGTAAT CGTGCTAAGC   2220

CATGCTGAAT TAGATCCTAA CTCTAATTTT GAAGCCTTAG GCACGATCCA TATTAACTTT   2280

TAAGGGATAA ATAATTGATA AAAAAGGAGA ATGATGCAAG TTTATCACCT TTCACACATT   2340

GATTTAGACG GCTATGCATG CCAGCTTGTT TCAAAACAAT TTTTTAAAAA TATCCAATGC   2400

TATAACGCTA ATTACGGGCG TGAAGTCTCA GCGAGAATTT ATGAGATTTT AAACGCGATC   2460

GCTCAATCTA AGAGAGTGA ATTCCTTATT TTGATTAGCG A                        2501
```

(2) INFORMATION FOR SEQ ID NO: 7:

(i) SEQUENCE CHARACTERISTICS:
        (A) LENGTH: 732 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Met Ala Asn Glu Arg Ser Lys Leu Ala Phe Lys Lys Thr Phe Pro Val
 1               5                  10                  15

Phe Lys Arg Phe Leu Gln Ser Lys Asp Leu Ala Leu Val Val Phe Val
                20                  25                  30

Ile Ala Ile Leu Ala Ile Ile Ile Val Pro Leu Pro Pro Phe Val Leu
            35                  40                  45

Asp Phe Leu Leu Thr Ile Ser Ile Ala Leu Ser Val Leu Ile Ile Leu
    50                  55                  60

Ile Gly Leu Tyr Ile Asp Lys Pro Thr Asp Phe Ser Ala Phe Pro Thr
65                  70                  75                  80

Leu Leu Leu Ile Val Thr Leu Tyr Arg Leu Ala Leu Asn Val Ala Thr
                85                  90                  95

Thr Arg Met Ile Leu Thr Gln Gly Tyr Lys Gly Pro Ser Ala Val Ser
                100                 105                 110

Ile Ile Ile Thr Ala Phe Gly Glu Phe Ser Val Ser Gly Asn Tyr Val
            115                 120                 125

Ile Gly Ala Ile Ile Phe Ser Ile Leu Val Leu Val Asn Leu Leu Val
        130                 135                 140

Val Thr Asn Gly Ser Thr Arg Val Thr Glu Val Arg Ala Arg Phe Ala
145                 150                 155                 160

Leu Asp Ala Met Pro Gly Lys Gln Met Ala Ile Asp Ala Asp Leu Asn
```

-continued

```
                165                 170                 175
Ser Gly Leu Ile Asp Asp Lys Glu Ala Lys Arg Arg Ala Ala Leu
            180                 185                 190
Ser Gln Glu Ala Asp Phe Tyr Gly Ala Met Asp Gly Ala Ser Lys Phe
            195                 200                 205
Val Lys Gly Asp Ala Ile Ala Ser Ile Ile Thr Leu Ile Asn Ile
            210                 215                 220
Ile Gly Gly Phe Leu Val Gly Val Phe Gln Arg Asp Met Ser Leu Ser
225                 230                 235                 240
Phe Ser Ala Ser Thr Phe Thr Ile Leu Thr Ile Gly Ala Gly Leu Val
                245                 250                 255
Gly Gln Ile Pro Ala Leu Ile Ile Ala Thr Arg Thr Gly Ile Val Ala
                260                 265                 270
Thr Arg Thr Thr Gln Asn Glu Glu Glu Asp Phe Ala Ser Lys Leu Ile
                275                 280                 285
Thr Gln Leu Thr Asn Lys Ser Lys Thr Leu Val Ile Val Gly Ala Ile
                290                 295                 300
Tyr Cys Phe Cys Thr Ile Pro Gly Leu Pro Thr Phe Ser Leu Ala Phe
305                 310                 315                 320
Val Gly Ala Leu Phe Leu Phe Ile Ala Trp Leu Ile Ser Arg Glu Gly
                325                 330                 335
Lys Asp Gly Leu Leu Thr Lys Leu Glu Asn Tyr Leu Ser Gln Lys Phe
                340                 345                 350
Gly Leu Asp Leu Ser Glu Lys Pro His Ser Ser Lys Ile Lys Pro His
                355                 360                 365
Ala Pro Thr Thr Arg Ala Lys Thr Gln Glu Glu Ile Lys Arg Glu Glu
            370                 375                 380
Glu Gln Ala Ile Asp Glu Val Leu Lys Ile Glu Phe Leu Glu Leu Ala
385                 390                 395                 400
Leu Gly Thr Gln Leu Tyr Ser Leu Ala Asp Met Lys Gln Gly Gly Asp
                405                 410                 415
Leu Leu Glu Arg Ile Arg Gly Ile Arg Lys Lys Ile Ala Ser Asp Tyr
                420                 425                 430
Gly Phe Leu Met Pro Gln Ile Arg Ile Arg Asp Asn Leu Gln Leu Pro
                435                 440                 445
Pro Thr His Tyr Glu Ile Lys Leu Lys Gly Ile Val Ile Gly Glu Gly
                450                 455                 460
Met Val Met Pro Asp Lys Phe Leu Ala Met Asn Thr Gly Phe Val Asn
465                 470                 475                 480
Lys Glu Ile Glu Gly Ile Pro Thr Lys Glu Pro Ala Phe Gly Met Asp
                485                 490                 495
Ala Leu Trp Ile Glu Thr Lys Asn Lys Glu Glu Ala Ile Ile Gln Gly
                500                 505                 510
Tyr Thr Ile Ile Asp Pro Ser Thr Val Ile Ala Thr His Thr Ser Glu
                515                 520                 525
Leu Val Lys Lys Tyr Ala Glu Asp Phe Ile Thr Lys Asp Glu Val Lys
            530                 535                 540
Ser Leu Leu Glu Arg Leu Ala Lys Asp Tyr Pro Thr Ile Val Glu Glu
545                 550                 555                 560
Ser Lys Lys Ile Pro Thr Gly Ala Ile Arg Ser Val Leu Gln Ala Leu
                565                 570                 575
Leu His Glu Lys Ile Pro Ile Lys Asp Met Leu Thr Ile Leu Glu Thr
                580                 585                 590
```

-continued

```
Ile Thr Asp Ile Ala Pro Leu Val Gln Asn Asp Val Asn Ile Leu Thr
        595                 600                 605
Glu Gln Val Arg Ala Arg Leu Ser Arg Val Ile Thr Asn Ala Phe Lys
    610                 615                 620
Ser Glu Asp Gly Arg Leu Lys Phe Leu Thr Phe Ser Thr Asp Ser Glu
625                 630                 635                 640
Gln Phe Leu Leu Asn Lys Leu Arg Glu Asn Gly Thr Ser Lys Ser Leu
                645                 650                 655
Leu Leu Asn Val Gly Glu Leu Gln Lys Leu Ile Glu Ala Val Ser Glu
            660                 665                 670
Glu Ala Met Lys Val Leu Gln Lys Gly Ile Ala Pro Val Ile Leu Ile
        675                 680                 685
Val Glu Pro Asn Leu Arg Lys Ala Leu Ser Asn Gln Met Glu Gln Ala
    690                 695                 700
Arg Ile Asp Val Ile Val Leu Ser His Ala Glu Leu Asp Pro Asn Ser
705                 710                 715                 720
Asn Phe Glu Ala Leu Gly Thr Ile His Ile Asn Phe
                725                 730
```

(2) INFORMATION FOR SEQ ID NO: 8:

(i) SEQUENCE CHARACTERISTICS:
        (A) LENGTH: 732 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Met Ala Asn Glu Arg Ser Lys Leu Ala Phe Lys Lys Thr Phe Pro Val
1               5                   10                  15
Phe Lys Arg Phe Leu Gln Ser Lys Asp Leu Ala Leu Val Val Phe Val
                20                  25                  30
Ile Ala Ile Leu Ala Ile Ile Ile Val Pro Leu Pro Pro Phe Val Leu
            35                  40                  45
Asp Phe Leu Leu Thr Ile Ser Ile Ala Leu Ser Val Leu Ile Ile Leu
        50                  55                  60
Ile Gly Leu Tyr Ile Asp Lys Pro Thr Asp Phe Ser Ala Phe Pro Thr
65                  70                  75                  80
Leu Leu Leu Ile Val Thr Leu Tyr Arg Leu Ala Leu Asn Val Ala Thr
                85                  90                  95
Thr Arg Met Ile Leu Thr Gln Gly Tyr Lys Gly Pro Ser Ala Val Ser
            100                 105                 110
Ile Ile Ile Thr Ala Phe Gly Glu Phe Ser Val Ser Gly Asn Tyr Val
        115                 120                 125
Ile Gly Ala Ile Ile Phe Ser Ile Leu Val Leu Val Asn Leu Leu Val
    130                 135                 140
Val Thr Asn Gly Ser Thr Arg Val Thr Glu Val Arg Ala Arg Phe Ala
145                 150                 155                 160
Leu Asp Ala Met Pro Gly Lys Gln Met Ala Ile Asp Ala Asp Leu Asn
                165                 170                 175
Ser Gly Leu Ile Asp Asp Lys Glu Ala Lys Lys Arg Arg Ala Ala Leu
            180                 185                 190
Ser Gln Glu Ala Asp Phe Tyr Gly Ala Met Asp Gly Ala Ser Lys Phe
        195                 200                 205
```

-continued

Val Lys Gly Asp Ala Ile Ala Ser Ile Ile Ile Thr Leu Ile Asn Ile
    210             215                 220

Ile Gly Gly Phe Leu Val Gly Val Phe Gln Arg Asp Met Ser Leu Ser
225             230                 235                 240

Phe Ser Ala Ser Thr Phe Thr Ile Leu Thr Ile Gly Asp Gly Leu Val
            245                 250                 255

Gly Gln Ile Pro Ala Leu Ile Ile Ala Thr Arg Thr Gly Ile Val Ala
            260                 265                 270

Thr Arg Thr Thr Gln Asn Glu Glu Glu Asp Phe Ala Ser Lys Leu Ile
        275                 280                 285

Thr Gln Leu Thr Asn Lys Ser Lys Thr Leu Val Ile Val Gly Ala Ile
        290                 295                 300

Tyr Cys Phe Cys Thr Ile Pro Gly Leu Pro Thr Phe Ser Leu Ala Phe
305             310                 315                 320

Val Gly Ala Leu Phe Leu Phe Ile Ala Trp Leu Ile Ser Arg Glu Gly
            325                 330                 335

Lys Asp Gly Leu Leu Thr Lys Leu Glu Asn Tyr Leu Ser Gln Lys Phe
            340                 345                 350

Gly Leu Asp Leu Ser Glu Lys Pro His Ser Ser Lys Ile Lys Pro His
            355                 360                 365

Ala Pro Thr Thr Arg Ala Lys Thr Gln Glu Glu Ile Lys Arg Glu Glu
            370                 375                 380

Glu Gln Ala Ile Asp Glu Val Leu Lys Ile Glu Phe Leu Glu Leu Ala
385             390                 395                 400

Leu Gly Tyr Gln Leu Tyr Ser Leu Ala Asp Met Lys Gln Gly Gly Asp
            405                 410                 415

Leu Leu Glu Arg Ile Arg Gly Ile Arg Lys Lys Ile Ala Ser Asp Tyr
            420                 425                 430

Gly Phe Leu Met Pro Gln Ile Arg Ile Arg Asp Asn Leu Gln Leu Pro
            435                 440                 445

Pro Thr His Tyr Glu Ile Lys Leu Lys Gly Ile Val Ile Gly Glu Gly
    450                 455                 460

Met Val Met Pro Asp Lys Phe Leu Ala Met Asn Thr Gly Phe Val Asn
465             470                 475                 480

Lys Glu Ile Glu Gly Ile Pro Thr Lys Glu Pro Ala Phe Gly Met Asp
            485                 490                 495

Ala Leu Trp Ile Glu Thr Lys Asn Lys Glu Glu Ala Ile Ile Gln Gly
            500                 505                 510

Tyr Thr Ile Ile Asp Pro Ser Thr Val Ile Ala Thr His Thr Ser Glu
        515                 520                 525

Leu Val Lys Lys Tyr Ala Glu Asp Phe Ile Thr Lys Asp Glu Val Lys
    530                 535                 540

Ser Leu Leu Glu Arg Leu Ala Lys Asp Tyr Pro Thr Ile Val Glu Glu
545             550                 555                 560

Ser Lys Lys Ile Pro Thr Gly Ala Ile Arg Ser Val Leu Gln Ala Leu
            565                 570                 575

Leu His Glu Lys Ile Pro Ile Lys Asp Met Leu Thr Ile Leu Glu Thr
            580                 585                 590

Ile Thr Asp Ile Ala Pro Leu Val Gln Asn Asp Val Asn Ile Leu Thr
            595                 600                 605

Glu Gln Val Arg Ala Arg Leu Ser Arg Val Ile Thr Asn Ala Phe Lys
            610                 615                 620

```
Ser Glu Asp Gly Arg Leu Lys Phe Leu Thr Phe Ser Thr Asp Ser Glu
625                 630                 635                 640

Gln Phe Leu Leu Asn Lys Leu Arg Glu Asn Gly Thr Ser Lys Ser Leu
            645                 650                 655

Leu Leu Asn Val Gly Glu Leu Gln Lys Leu Ile Glu Ala Val Ser Glu
        660                 665                 670

Glu Ala Met Lys Val Leu Gln Lys Gly Ile Ala Pro Val Ile Leu Ile
            675                 680                 685

Val Glu Pro Asn Leu Arg Lys Ala Leu Ser Asn Gln Met Glu Gln Ala
        690                 695                 700

Arg Ile Asp Val Ile Val Leu Ser His Ala Glu Leu Asp Pro Asn Ser
705                 710                 715                 720

Asn Phe Glu Ala Leu Gly Thr Ile His Ile Asn Phe
                    725                 730

(2) INFORMATION FOR SEQ ID NO: 9:

(i) SEQUENCE CHARACTERISTICS:
        (A) LENGTH: 724 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Met Ala Lys Asn Lys Ile Val Asp Leu Val Phe Pro Phe Leu Gly Pro
1               5                   10                  15

Leu Ile Ala Pro Val Leu Lys Ala Lys Ser Leu Thr Ile Val Gly Phe
            20                  25                  30

Leu Val Cys Ile Leu Ala Ile Ile Val Pro Leu Pro Ser Pro Ile
        35                  40                  45

Leu Asp Phe Phe Leu Ala Leu Ser Ile Ala Leu Ser Val Leu Ile Ile
    50                  55                  60

Leu Ile Ser Ile Tyr Ile Pro Lys Pro Thr Asp Leu Thr Thr Phe Pro
65                  70                  75                  80

Thr Leu Ile Leu Ile Ile Thr Leu Phe Arg Leu Ser Leu Asn Ile Ala
            85                  90                  95

Thr Thr Arg Met Ile Leu Ser Glu Gly Gln Asn Gly Pro Glu Ala Val
            100                 105                 110

Ser Glu Ile Ile Ala Ala Phe Gly Glu Phe Val Val Gly Gly Asn Met
        115                 120                 125

Val Ile Gly Val Ile Val Phe Cys Ile Leu Val Leu Ile Asn Phe Met
    130                 135                 140

Val Val Thr Lys Gly Ser Thr Arg Val Ser Glu Val Gln Ala Arg Phe
145                 150                 155                 160

Thr Leu Asp Ala Met Pro Gly Lys Gln Met Ala Ile Asp Ala Asp Leu
            165                 170                 175

Asn Ala Gly Leu Ile Asp Glu Gln Thr Ala Arg Ala Arg Arg Gln Glu
        180                 185                 190

Val Ile Ala Glu Ala Asn Phe Tyr Gly Ala Met Asp Gly Ser Ser Lys
    195                 200                 205

Phe Ile Lys Gly Asp Ala Val Ala Gly Ile Ile Thr Ile Ile Asn
        210                 215                 220

Ile Ile Gly Gly Phe Leu Ile Gly Ser Phe Gln His Asp Met Ala Leu
225                 230                 235                 240
```

-continued

```
Ser Asp Ala Ala Ser Thr Tyr Thr Ile Leu Thr Ile Gly Asp Gly Leu
            245                 250                 255

Val Ser Gln Ile Pro Gly Leu Ile Thr Ser Thr Ala Thr Ala Ile Ile
        260                 265                 270

Ile Thr Arg Ala Ser Lys Asp Glu Glu Asn Phe Ala Glu Gly Thr Leu
    275                 280                 285

Thr Gln Leu Leu Ser Glu Tyr Arg Thr Leu Leu Ile Val Gly Phe Val
290                 295                 300

Leu Phe Ile Phe Ala Leu Val Pro Gly Leu Pro Thr Leu Ser Leu Gly
305                 310                 315                 320

Phe Met Ala Leu Val Phe Leu Ser Leu Gly Tyr Leu Tyr Lys Gln Val
                325                 330                 335

Lys Glu Gly Lys Ile Asp Ile Thr Thr Val Lys Ser Lys Pro Ser
                340                 345                 350

Ala Ala Val Ala Ser Gln Ser Gly Ala Gly Thr Thr Ala Ala Pro
                355                 360                 365

Ala Lys Lys Ser Glu Glu Ile Leu Lys Glu Glu His Lys Ile
            370                 375                 380

Asn Asp Ile Leu Lys Val Glu Ile Leu Glu Leu Glu Leu Gly Tyr Gly
385                 390                 395                 400

Leu Ile Lys Leu Ala Glu Asn Glu Leu Thr Glu Arg Ile Arg Ser Met
                405                 410                 415

Arg Arg Ser Ile Ala Glu Ser Leu Gly Phe Leu Met Pro Lys Ile Arg
            420                 425                 430

Ile Arg Asp Asn Leu Arg Leu Lys Pro Asn Glu Tyr Ser Phe Lys Leu
        435                 440                 445

Lys Gly Val Ser Ile Ala Ser Ala Glu Ile Tyr Pro Asp Lys Tyr Leu
    450                 455                 460

Ala Met Asp Ser Gly Phe Ile Thr Glu Glu Ile Glu Gly Ile Ala Thr
465                 470                 475                 480

Lys Glu Pro Ala Phe Asn Ser Asp Ala Leu Trp Ile Asp Ala Asn Leu
                485                 490                 495

Lys Asp Glu Ala Thr Leu Asn Gly Tyr Ile Val Ile Asp Pro Ala Ser
            500                 505                 510

Val Ile Ser Thr His Met Ser Glu Leu Ala Lys Ala His Ala Ser Glu
        515                 520                 525

Leu Leu Thr Arg Gln Glu Val Gln Asn Leu Leu Asp Lys Val Lys Asn
    530                 535                 540

Asp Tyr Pro Ile Ile Val Glu Gly Ala Leu Gly Val Ala Pro Val Ser
545                 550                 555                 560

Leu Ile Gln Lys Ile Leu Lys Asp Leu Leu Lys His His Ile Pro Ile
                565                 570                 575

Lys Asp Met Leu Thr Ile Leu Glu Ser Val Ser Asp Ile Ala Glu Val
            580                 585                 590

Ser Lys Ser Phe Asp Met Ile Ile Glu His Val Arg Ala Ser Leu Ala
        595                 600                 605

Arg Met Ile Thr Asn Met Tyr Leu Asp Asp Lys Gly Asn Leu Asp Ile
    610                 615                 620

Phe Ile Leu Asp Ser Ala Ser Ser Ala Val Leu Met Glu Asn Val Gln
625                 630                 635                 640

Phe Arg Asp Gly Ser Tyr His Leu Pro Leu Ser Val Ala Gln Thr Gly
                645                 650                 655

Thr Leu Val Asp Thr Leu Arg Ala Glu Val Ala Ala Val Ala Asn Gly
```

```
                    660                 665                 670
Arg Ile Lys Pro Phe Ile Leu Cys Val Glu Pro Gln Leu Arg Lys Phe
            675                 680                 685

Ile Ala Asp Ile Cys Tyr Asn Phe Ser Ile Asn Ile Val Val Leu Ser
690                 695                 700

Phe Ala Glu Ile Ala Glu Asn Thr Asn Phe Asn Thr Glu Gly Ile Ile
705                 710                 715                 720

Arg Ile Glu Leu (2) INFORMATION FOR SEQ ID NO: 10:

(i) SEQUENCE CHARACTERISTICS:
        (A) LENGTH: 700 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Met Ala Asp Ala Ala Ala Pro Asn Ala Ser Ser Met Pro Ser Ala Lys
1               5                   10                  15

Ser Leu Leu Asp Gly Leu Met Arg Gly Glu Met Gly Leu Ala Leu Gly
            20                  25                  30

Val Val Gly Ile Ile Val Leu Ile Ile Pro Val Pro Ala Pro Leu
        35                  40                  45

Leu Asp Val Leu Leu Ala Ile Ser Leu Thr Gly Ser Val Leu Ile Leu
50                  55                  60

Met Thr Ala Ile Leu Ile Lys Lys Pro Leu Glu Phe Thr Ser Phe Pro
65                  70                  75                  80

Thr Val Leu Leu Val Thr Thr Leu Phe Arg Leu Gly Leu Asn Ile Ala
                85                  90                  95

Ser Thr Arg Leu Ile Leu Ser His Gly Gln Glu Gly Thr Gly Gly Ala
            100                 105                 110

Gly Ala Val Ile Glu Ala Phe Gly His Leu Met Met Gln Gly Asn Phe
            115                 120                 125

Val Ile Gly Val Ile Val Phe Ile Ile Leu Ile Val Val Asn Phe Met
        130                 135                 140

Val Val Thr Lys Gly Ser Gly Arg Ile Ala Glu Val Ala Ala Arg Phe
145                 150                 155                 160

Thr Leu Asp Ser Met Pro Gly Lys Gln Met Ala Ile Asp Ala Asp Leu
                165                 170                 175

Ser Thr Gly Leu Ile Ser Gln Asp Glu Ala Lys Ile Arg Arg Lys Glu
            180                 185                 190

Leu Glu Gln Glu Ser Thr Phe Phe Gly Ala Met Asp Gly Ala Ser Lys
            195                 200                 205

Phe Val Lys Gly Asp Ala Ile Ala Gly Leu Ile Ile Thr Ala Ile Asn
        210                 215                 220

Ile Ile Gly Gly Ile Ile Ile Gly Val Val Gln His Lys Met Pro Phe
225                 230                 235                 240

Gly Asp Ala Ala Ser Thr Tyr Thr Ile Met Thr Ile Gly Asp Gly Leu
                245                 250                 255

Val Ser Gln Ile Pro Ala Leu Ile Ile Ser Ile Ala Ala Gly Met Val
            260                 265                 270

Val Ser Lys Ala Gly Val Glu Gly Ser Ala Asp Lys Ala Leu Thr Thr
            275                 280                 285
```

```
Gln Leu Ala Met Asn Pro Val Gly Leu Gly Met Val Ser Ala Ser Ser
    290                 295                 300

Gly Ile Ile Ala Leu Ile Pro Gly Met Pro Ile Phe Pro Phe Ala Ala
305                 310                 315                 320

Met Ala Leu Ala Ala Gly Ala Leu Ala Tyr Lys Arg Val Gln Asp Ala
                325                 330                 335

Lys Lys Pro Lys Ala Leu Asp Pro Ala Asp Leu Glu Ala Ala Pro
                340                 345                 350

Ser Glu Pro Glu Glu Pro Ile Ser Ala Ser Leu Ala Ile Asp Asp
    355                 360                 365

Val Lys Ile Glu Leu Gly Tyr Gly Leu Leu Thr Leu Ile Asn Asp Leu
    370                 375                 380

Asp Gly Arg Lys Leu Thr Asp Gln Ile Arg Ala Leu Arg Lys Thr Leu
385                 390                 395                 400

Ala Ser Glu Tyr Gly Phe Val Met Pro Pro Val Arg Ile Leu Asp Asn
                405                 410                 415

Met Arg Leu Ala Asn Gln Gly Tyr Ala Ile Arg Ile Lys Glu Met Glu
        420                 425                 430

Ala Gly Ala Gly Glu Val Arg Leu Gly Cys Leu Met Cys Met Asp Pro
        435                 440                 445

Arg Gly Gly Gln Val Glu Leu Pro Gly Glu His Val Arg Glu Pro Ala
    450                 455                 460

Phe Gly Leu Pro Ala Thr Trp Ile Ala Asp Asp Leu Arg Glu Glu Ala
465                 470                 475                 480

Thr Phe Arg Gly Tyr Thr Val Val Asp Pro Ala Thr Val Leu Thr Thr
                485                 490                 495

His Leu Thr Glu Ile Leu Lys Glu Asn Met Ala Asp Leu Leu Ser Tyr
            500                 505                 510

Ala Glu Val Gln Lys Leu Leu Lys Glu Leu Pro Glu Thr Gln Lys Lys
        515                 520                 525

Leu Val Asp Asp Leu Ile Pro Gly Thr Val Thr Ala Thr Thr Val Gln
    530                 535                 540

Arg Val Leu Gln Ser Leu Leu Arg Glu Arg Val Ser Ile Arg Asp Leu
545                 550                 555                 560

Pro Gln Ile Leu Glu Gly Val Gly Glu Ala Ala Pro His Thr Ala Ser
                565                 570                 575

Val Thr Gln Leu Val Glu Gln Val Arg Ala Arg Leu Ala Arg Gln Leu
                580                 585                 590

Cys Trp Ala Asn Arg Gly Asp Asp Gly Ala Leu Pro Ile Ile Thr Leu
        595                 600                 605

Ser Ala Asp Trp Glu Gln Ala Phe Ala Glu Ala Leu Ile Gly Pro Gly
    610                 615                 620

Asp Asp Lys Gln Leu Ala Leu Pro Pro Ser Arg Leu Gln Asp Phe Ile
625                 630                 635                 640

Arg Gly Val Arg Asp Ser Phe Glu Arg Ala Ala Leu Ala Gly Glu Ala
                645                 650                 655

Pro Val Leu Leu Thr Ser Pro Gly Val Arg Pro Tyr Val Arg Ser Ile
            660                 665                 670

Ile Glu Arg Phe Arg Gly Gln Thr Val Val Met Ser Gln Asn Glu Ile
        675                 680                 685

His Pro Arg Ala Arg Leu Lys Thr Val Gly Met Val
    690                 695                 700
```

(2) INFORMATION FOR SEQ ID NO: 11:

(i) SEQUENCE CHARACTERISTICS:
        (A) LENGTH: 704 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

```
Met Asn Pro His Asp Leu Glu Trp Leu Asn Arg Ile Gly Glu Arg Lys
  1               5                  10                  15

Asp Ile Met Leu Ala Val Leu Leu Ala Val Val Phe Met Met Val
             20                  25                  30

Leu Pro Leu Pro Pro Leu Val Leu Asp Ile Leu Ile Ala Val Asn Met
             35                  40                  45

Thr Ile Ser Val Leu Leu Met Ile Ala Ile Tyr Ile Asn Ser Pro
 50                  55                  60

Leu Gln Phe Ser Ala Phe Pro Ala Val Leu Leu Val Thr Thr Leu Phe
 65                  70                  75                  80

Arg Leu Ala Leu Ser Val Ser Thr Thr Arg Met Ile Leu Leu Gln Ala
                 85                  90                  95

Asp Ala Gly Gln Ile Val Tyr Thr Phe Gly Asn Phe Val Val Gly Gly
                100                 105                 110

Asn Leu Ile Val Gly Ile Val Ile Phe Leu Ile Ile Thr Ile Val Gln
            115                 120                 125

Phe Leu Val Ile Thr Lys Gly Ser Glu Arg Val Ala Glu Val Ser Ala
130                 135                 140

Arg Phe Ser Leu Asp Ala Met Pro Gly Lys Gln Met Ser Ile Asp Gly
145                 150                 155                 160

Asp Met Arg Ala Gly Val Ile Asp Val Asn Glu Ala Arg Glu Arg Arg
                165                 170                 175

Ala Thr Ile Glu Lys Glu Ser Gln Met Phe Gly Ser Met Asp Gly Ala
                180                 185                 190

Met Lys Phe Val Lys Gly Asp Ala Ile Ala Gly Leu Ile Ile Ile Phe
            195                 200                 205

Val Asn Ile Leu Gly Gly Val Thr Ile Gly Val Thr Gln Lys Gly Leu
210                 215                 220

Ala Ala Ala Glu Ala Leu Gln Leu Tyr Ser Ile Leu Thr Val Gly Asp
225                 230                 235                 240

Gly Met Val Ser Gln Val Pro Ala Leu Leu Ile Ala Ile Thr Ala Gly
                245                 250                 255

Ile Ile Val Thr Arg Val Ser Ser Glu Asp Ser Ser Asp Leu Gly Ser
            260                 265                 270

Asp Ile Gly Lys Gln Val Ala Gln Pro Lys Ala Met Leu Ile Gly
            275                 280                 285

Gly Val Leu Leu Leu Leu Phe Gly Leu Ile Pro Gly Phe Pro Thr Val
            290                 295                 300

Thr Phe Leu Ile Leu Ala Leu Leu Val Gly Cys Gly Gly Tyr Met Leu
305                 310                 315                 320

Ser Arg Lys Gln Ser Arg Asn Asp Glu Ala Asn Gln Asp Leu Gln Ser
                325                 330                 335

Ile Leu Thr Ser Gly Ser Gly Ala Pro Ala Ala Arg Thr Lys Ala Lys
            340                 345                 350
```

-continued

```
Thr Ser Gly Ala Asn Lys Gly Arg Leu Gly Glu Gln Glu Ala Phe Ala
        355                 360                 365
Met Thr Val Pro Leu Leu Ile Asp Val Asp Ser Ser Gln Gln Glu Ala
    370                 375                 380
Leu Glu Ala Asn Ala Leu Asn Asp Glu Leu Val Arg Val Arg Arg Ala
385                 390                 395                 400
Leu Tyr Leu Asp Leu Gly Val Pro Phe Pro Gly Ile His Leu Arg Phe
                405                 410                 415
Asn Glu Gly Met Gly Glu Gly Glu Tyr Ile Ile Ser Leu Gln Glu Val
            420                 425                 430
Pro Val Ala Arg Gly Glu Leu Lys Ala Gly Tyr Leu Leu Val Arg Glu
        435                 440                 445
Ser Val Ser Gln Leu Glu Leu Leu Gly Ile Pro Tyr Glu Lys Gly Glu
    450                 455                 460
His Leu Leu Pro Asp Gln Glu Ala Phe Trp Val Ser Val Glu Tyr Glu
465                 470                 475                 480
Glu Arg Leu Glu Lys Ser Gln Leu Glu Phe Phe Ser His Ser Gln Val
                485                 490                 495
Leu Thr Trp His Leu Ser His Val Leu Arg Glu Tyr Ala Glu Asp Phe
            500                 505                 510
Ile Gly Ile Gln Glu Thr Arg Tyr Leu Leu Glu Gln Met Glu Gly Gly
        515                 520                 525
Tyr Gly Glu Leu Ile Lys Glu Val Gln Arg Ile Val Pro Leu Gln Arg
    530                 535                 540
Met Thr Glu Ile Leu Gln Arg Leu Val Gly Glu Asp Ile Ser Ile Arg
545                 550                 555                 560
Asn Met Arg Ser Ile Leu Glu Ala Met Val Glu Trp Gly Gln Lys Glu
                565                 570                 575
Lys Asp Val Val Gln Leu Thr Glu Tyr Ile Arg Ser Ser Leu Lys Arg
            580                 585                 590
Tyr Ile Cys Tyr Lys Tyr Ala Asn Gly Asn Asn Ile Leu Pro Ala Tyr
        595                 600                 605
Leu Phe Asp Gln Glu Val Glu Lys Ile Arg Ser Gly Val Arg Gln
    610                 615                 620
Thr Ser Ala Gly Ser Tyr Leu Ala Leu Glu Pro Ala Val Thr Glu Ser
625                 630                 635                 640
Leu Leu Glu Gln Val Arg Lys Thr Ile Gly Asp Leu Ser Gln Ile Gln
                645                 650                 655
Ser Lys Pro Val Leu Ile Val Ser Met Asp Ile Arg Arg Tyr Val Arg
            660                 665                 670
Lys Leu Ile Glu Ser Glu Tyr Tyr Gly Leu Pro Val Leu Ser Tyr Gln
        675                 680                 685
Glu Leu Thr Gln Gln Ile Asn Ile Gln Pro Leu Gly Arg Ile Cys Leu
    690                 695                 700
```

(2) INFORMATION FOR SEQ ID NO: 12:

(i) SEQUENCE CHARACTERISTICS:
        (A) LENGTH: 685 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Met Leu Leu Ser Leu Leu Asn Ser Ala Arg Leu Arg Pro Glu Leu Leu
 1               5                  10                  15

Ile Leu Val Leu Met Val Met Ile Ile Ser Met Phe Val Ile Pro Leu
             20                  25                  30

Pro Thr Tyr Leu Val Asp Phe Leu Ile Ala Leu Asn Ile Val Leu Ala
         35                  40                  45

Ile Leu Val Phe Met Gly Ser Phe Tyr Ile Asp Arg Ile Leu Ser Phe
 50                  55                  60

Ser Thr Phe Pro Ala Val Leu Leu Ile Thr Thr Leu Phe Arg Leu Ala
 65              70                  75                  80

Leu Ser Ile Ser Thr Ser Arg Leu Ile Leu Ile Glu Ala Asp Ala Gly
             85                  90                  95

Glu Ile Ile Ala Thr Phe Gly Gln Phe Val Ile Gly Asp Ser Leu Ala
            100                 105                 110

Val Gly Phe Val Val Phe Ser Ile Val Thr Val Val Gln Phe Ile Val
        115                 120                 125

Ile Thr Lys Gly Ser Glu Arg Val Ala Glu Val Ala Ala Arg Phe Ser
    130                 135                 140

Leu Asp Gly Met Pro Gly Lys Gln Met Ser Ile Asp Ala Asp Leu Lys
145                 150                 155                 160

Ala Gly Ile Ile Asp Ala Asp Ala Ala Arg Glu Arg Arg Ser Val Leu
                165                 170                 175

Glu Arg Glu Ser Gln Leu Tyr Gly Ser Phe Asp Gly Ala Met Lys Phe
            180                 185                 190

Ile Lys Gly Asp Ala Ile Ala Gly Ile Ile Ile Phe Val Asn Phe
    195                 200                 205

Ile Gly Gly Ile Ser Val Gly Met Thr Arg His Gly Met Asp Leu Ser
    210                 215                 220

Ser Ala Leu Ser Thr Tyr Thr Met Leu Thr Ile Gly Asp Gly Leu Val
225                 230                 235                 240

Ala Gln Ile Pro Ala Leu Leu Ile Ala Ile Ser Ala Gly Phe Ile Val
                245                 250                 255

Thr Arg Val Asn Gly Asp Thr Asp Asn Met Gly Arg Asn Ile Met Thr
            260                 265                 270

Gln Leu Leu Asn Asn Pro Phe Val Leu Val Val Thr Ala Ile Leu Thr
    275                 280                 285

Ile Ser Met Gly Thr Leu Pro Gly Phe Pro Leu Pro Val Phe Val Ile
    290                 295                 300

Leu Ser Val Val Leu Ser Val Leu Phe Tyr Phe Lys Phe Arg Glu Ala
305                 310                 315                 320

Lys Arg Ser Ala Ala Lys Pro Lys Thr Ser Lys Gly Glu Gln Pro Leu
                325                 330                 335

Ser Ile Glu Glu Lys Glu Gly Ser Ser Leu Gly Leu Ile Gly Asp Leu
            340                 345                 350

Asp Lys Val Ser Thr Glu Thr Val Pro Leu Ile Leu Leu Val Pro Lys
            355                 360                 365

Ser Arg Arg Glu Asp Leu Glu Lys Ala Gln Leu Ala Glu Arg Leu Arg
        370                 375                 380

Ser Gln Phe Phe Ile Asp Tyr Gly Val Arg Leu Pro Glu Val Leu Leu
385                 390                 395                 400

Arg Asp Gly Glu Gly Leu Asp Asp Asn Ser Ile Val Leu Leu Ile Asn
                405                 410                 415

Glu Ile Arg Val Glu Gln Phe Thr Val Tyr Phe Asp Leu Met Arg Val
```

```
                    420             425             430
    Val Asn Tyr Ser Asp Glu Val Val Ser Phe Gly Ile Asn Pro Thr Ile
            435             440             445

His Gln Gln Gly Ser Ser Gln Tyr Phe Trp Val Thr His Glu Glu Gly
        450             455             460

Glu Lys Leu Arg Glu Leu Gly Tyr Val Leu Arg Asn Ala Leu Asp Glu
    465             470             475             480

Leu Tyr His Cys Leu Ala Val Thr Val Ala Arg Asn Val Asn Glu Tyr
                    485             490             495

Phe Gly Ile Gln Glu Thr Lys His Met Leu Asp Gln Leu Glu Ala Lys
                500             505             510

Phe Pro Asp Leu Leu Lys Glu Val Leu Arg His Ala Thr Val Gln Arg
                515             520             525

Ile Ser Glu Val Leu Gln Arg Leu Leu Ser Glu Arg Val Ser Val Arg
        530             535             540

Asn Met Lys Leu Ile Met Glu Ala Leu Ala Leu Trp Ala Pro Arg Glu
    545             550             555             560

Lys Asp Val Ile Asn Leu Val Glu His Ile Arg Gly Ala Met Ala Arg
                    565             570             575

Tyr Ile Cys His Lys Phe Ala Asn Gly Gly Glu Leu Arg Ala Val Met
                580             585             590

Val Ser Ala Glu Val Glu Asp Val Ile Arg Lys Gly Ile Arg Gln Thr
        595             600             605

Ser Gly Ser Thr Phe Leu Ser Leu Asp Pro Glu Ala Ser Ala Asn Leu
        610             615             620

Met Asp Leu Ile Thr Leu Lys Leu Asp Asp Leu Leu Ile Ala His Lys
    625             630             635             640

Asp Leu Val Leu Leu Thr Ser Val Asp Val Arg Arg Phe Ile Lys Lys
                    645             650             655

Met Ile Glu Gly Arg Phe Pro Asp Leu Glu Val Leu Ser Phe Gly Glu
                660             665             670

Ile Ala Asp Ser Lys Ser Val Asn Val Ile Lys Thr Ile
                675             680             685

(2) INFORMATION FOR SEQ ID NO: 13:

(i) SEQUENCE CHARACTERISTICS:
        (A) LENGTH: 666 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Met Val Met Ile Ile Ala Met Leu Ile Ile Pro Leu Pro Thr Tyr Leu
1               5               10              15

Val Asp Phe Leu Ile Gly Leu Asn Ile Val Leu Ala Ile Leu Val Phe
                20              25              30

Met Gly Ser Phe Tyr Ile Glu Arg Ile Leu Ser Phe Ser Thr Phe Pro
            35              40              45

Ser Val Leu Leu Ile Thr Thr Leu Phe Arg Leu Ala Leu Ser Ile Ser
        50              55              60

Thr Ser Arg Leu Ile Leu Val Asp Ala Asp Arg Gly Lys Ile Ile Thr
65              70              75              80

Thr Phe Gly Gln Phe Val Ile Gly Asp Ser Leu Ala Val Gly Phe Val
```

-continued

```
                85                  90                  95
Ile Phe Ser Ile Val Thr Val Val Gln Phe Ile Val Thr Lys Gly
                100                 105                 110
Ser Glu Arg Val Ala Glu Val Ala Ala Arg Phe Ser Leu Asp Gly Met
                115                 120                 125
Pro Gly Lys Gln Met Ser Ile Asp Ala Asp Leu Lys Ala Gly Ile Ile
            130                 135                 140
Asp Ala Ala Gly Ala Lys Glu Arg Arg Ser Ile Leu Glu Arg Glu Ser
145                 150                 155                 160
Gln Leu Tyr Gly Ser Phe Asp Gly Ala Met Lys Phe Ile Lys Gly Asp
                165                 170                 175
Ala Ile Ala Gly Ile Ile Ile Ile Phe Val Asn Leu Ile Gly Gly Ile
                180                 185                 190
Ser Val Gly Met Ser Gln His Gly Met Ser Leu Ser Gly Ala Leu Ser
            195                 200                 205
Thr Tyr Thr Ile Leu Thr Ile Gly Asp Gly Leu Val Ser Gln Ile Pro
            210                 215                 220
Ala Leu Leu Ile Ser Ile Ser Ala Gly Phe Met Leu Thr Arg Val Asn
225                 230                 235                 240
Gly Asp Ser Asp Asn Met Gly Arg Asn Ile Met Ser Gln Ile Phe Gly
                245                 250                 255
Asn Pro Phe Val Leu Ile Val Thr Ser Ala Leu Ala Leu Ala Ile Gly
                260                 265                 270
Met Leu Pro Gly Phe Pro Phe Val Phe Leu Ile Ala Val Thr
                275                 280                 285
Leu Thr Ala Leu Phe Tyr Tyr Lys Lys Val Val Glu Lys Glu Lys Ser
            290                 295                 300
Leu Ser Glu Ser Asp Ser Ser Gly Tyr Thr Gly Thr Phe Asp Ile Asp
305                 310                 315                 320
Asn Thr His Asp Ser Ser Leu Ala Met Ile Glu Asn Leu Asp Arg Ile
                325                 330                 335
Ser Ser Glu Thr Val Pro Leu Ile Leu Leu Phe Ala Glu Asn Lys Ile
            340                 345                 350
Asn Ala Asn Asp Met Glu Gly Leu Ile Glu Arg Ile Arg Ser Gln Phe
            355                 360                 365
Phe Ile Asp Tyr Gly Val Arg Leu Pro Thr Ile Leu Tyr Arg Thr Ser
            370                 375                 380
Asn Glu Leu Lys Val Asp Asp Ile Val Leu Leu Ile Asn Glu Val Arg
385                 390                 395                 400
Ala Asp Ser Phe Asn Ile Tyr Phe Asp Lys Val Cys Ile Thr Asp Glu
                405                 410                 415
Asn Gly Asp Ile Asp Ala Leu Gly Ile Pro Val Val Ser Thr Ser Tyr
            420                 425                 430
Asn Glu Arg Val Ile Ser Trp Val Asp Val Ser Tyr Thr Glu Asn Leu
            435                 440                 445
Thr Asn Ile Asp Ala Lys Ile Lys Ser Ala Gln Asp Glu Phe Tyr His
        450                 455                 460
Gln Leu Ser Gln Ala Leu Leu Asn Ile Asn Glu Ile Phe Gly Ile
465                 470                 475                 480
Gln Glu Thr Lys Asn Met Leu Asp Gln Phe Glu Asn Arg Tyr Pro Asp
                485                 490                 495
Leu Leu Lys Glu Val Phe Arg His Val Thr Ile Gln Arg Ile Ser Glu
                500                 505                 510
```

-continued

```
Val Leu Gln Arg Leu Leu Gly Glu Asn Ile Ser Val Arg Asn Leu Lys
        515                 520                 525

Leu Ile Met Glu Ser Leu Ala Leu Trp Ala Pro Arg Glu Lys Asp Val
        530                 535                 540

Ile Thr Leu Val Glu His Val Arg Ala Ser Leu Ser Arg Tyr Ile Cys
545                 550                 555                 560

Ser Lys Ile Ala Val Ser Gly Glu Ile Lys Val Val Met Leu Ser Gly
                565                 570                 575

Tyr Ile Glu Asp Ala Ile Arg Lys Gly Ile Arg Gln Thr Ser Gly Gly
                580                 585                 590

Ser Phe Leu Asn Met Asp Ile Glu Val Ser Asp Glu Val Met Glu Thr
        595                 600                 605

Leu Ala His Ala Leu Arg Glu Leu Arg Asn Ala Lys Lys Asn Phe Val
        610                 615                 620

Leu Leu Val Ser Val Asp Ile Arg Arg Phe Val Lys Arg Leu Ile Asp
625                 630                 635                 640

Asn Arg Phe Lys Ser Ile Leu Val Ile Ser Tyr Ala Glu Ile Asp Glu
                645                 650                 655

Ala Tyr Thr Ile Asn Val Leu Lys Thr Ile
                660                 665
```

CLONING AND CHARACTERIZATION OF THE FLBA GENE OF *H. PYLORI*, PRODUCTION OF AFLAGELLATE STRAINS

This application is a divisional application of U.S. application Ser. No. 08/671,757 filed Jun. 28, 1996, now U.S. Pat. No. 6,476,213. Under the provisions of Section 119 of 35 U.S.C., applicants hereby claim the benefit of the filing date of French Patent Application No. 95 08068, filed Jul. 4, 1995, for this U.S. patent application Ser. No. 09/015,078.

*Helicobacter pylori* (also designated as *H.pylori*) is a Gram-negative bacterium which, to date, has been found exclusively on the surface of the mucosa of the stomach in man.

In common with most bacteria, *H.pylori* is sensitive to a medium which is at acid pH but, nevertheless, is able to tolerate acidity in the presence of physiological concentrations of urea (Marshall et al. (1990) Gastroenterol. 99: 697–702). By hydrolysing the urea to form carbon dioxide and ammonia, which are released into the microenvironment of the bacterium, the *H. pylori* urease enables the bacterium to survive in the acidic environment of the stomach. Recently, studies carried out on animal models have provided data suggesting that the urease is an important factor in the colonization of the gastric mucosa (Eaton et al. (1991) Infect. Immun. 59: 2470–2475). The urease is also suspected of causing injury, either directly or indirectly, to the gastric mucosa.

Currently, *Helicobacter pylori* (*H. pylori*) is recognized as being the etiological agent of antral gastrites, and appears to be one of the cofactors required for the development of ulcers. Furthermore, it appears that the development of gastric carcinomas may be associated with the presence of *H. pylori*.

In order to develop novel sensitive and specific means for detecting in-vitro infections due to bacteria of the *Helicobacter pylori* species, the inventors have been taking an interest in the system for regulating the mobility of these bacteria.

With this aim in view, they have been interested in different modifications of the *H. pylori* strains, modifications which did not affect the recognition of these bacteria by sera from infected patients but which nevertheless rendered it possible to avoid obtaining reactions of the "false positive" type, in particular with bacteria of the Campylobacter family, for example *Campylobacter jejuni*.

Furthermore, the inventors observed that it was possible, if need be, for the modified bacteria which were obtained to be employed in constructing immunogenic compositions or compositions used for vaccination. In this respect, the invention proposes, in particular, live attenuated bacterial strains.

In a first step, the inventors identified and isolated the gene flbA which is involved in the regulation of the biosynthesis of the flagella of *H. pylori* and, as a consequence, in the regulation of the mobility of the bacterium. The biosynthesis of the flagella comprises synthesizing flagellins A and B and synthesizing the sheath. The flbA gene regulates both the synthesis of flagellins A and B and the synthesis of the sheath which contains these flagellins. The inventors established that the flbA gene was also important in that it regulated the biosynthesis of the anchoring protein of the bacterium, also termed the "hook".

The invention therefore relates to a nucleotide sequence from the flbA gene regulating the biosynthesis of the proteins of the *Helicobacter pylori* flagella, characterized in that it is able to hybridize, under conditions of high stringency, with a probe corresponding to a nucleotide fragment from *H. pylori* which has been amplified using two oligonucleotides having the following sequences:

OLF1bA-1: ATGCCTCGAGGTCGAAAAGCAAGATG (SEQ ID NO:1).

OLF1bA-2: GAAATCTTCATACTGGCAGCTCC AGTC (SEQ ID NO:2), or able to hybridize, under conditions of high stringency, with these oliqonucleotides.

Such a sequence can be obtained by the steps of:

screening a genomic library containing the chromosomal DNA of an *H. pylori* strain with a probe corresponding to a nucleotide fragment from *H. pylori* which has been amplified using two oligonucleotides having the following sequences:

OLF1bA-1: ATGCCTCGAGGTCGAAAAGCAAGATG (SEQ ID NO:1).

OLF1bA-2: GAAATCTTCATACTGGCAGCTCC AGTC (SEQ ID NO:2), or able to hybridize, under conditions of high stringency, with these oligonucleotides, recovering the DNA sequences, which hybridize with said probe, subcloning the DNA sequences, which have been obtained in an appropriate vector of the plasmid type and selecting those modifiedvectors, which hybridize under conditions of high stringency with the probe corresponding to the DNA fragment from *H. pylori* which has been amplified using oligonucleotides OLF1bA-1 and OLF1bA-2, sequencing the DNA fragments contained in the plasmid vectors which hybridize with the above mentioned probe, and determining the open reading frame contained in these fragments.

Advantageously, those DNA fragments will be used to reconstitute the coding sequence of the FlbA gene, corresponding to an open reading frame comprising approximately 2196 nucleotides.

The genomic library containing the chromosomal DNA of *H. pylori* can be obtained from an *H. pylori* strain. A cosmid library may also be prepared from the chromosomal DNA of *H. pylori*.

An example of a strain which can be used for constructing this library is the strain N6, which was deposited in the NCIMB on 26 Jun. 1992 under No. NCIMB40512.

The two oligonucleotide primers which are used for preparing the probe which is intended for hybridizing the sought-after DNA which is present in the *H. pylori* DNA library are selected from the conserved regions of the various proteins of the LcrD/FlbF family.

The two oligonucleotide primers, OLFlbA-1 and OLFlbA-2, enabled a fragment to be amplified which was usable as a probe and which was of 130 base pairs, having the following sequence:

ATG CCA GGA AAG CAA ATG GCG ATT GAT GCG GAT TTA AAT TCA GGG CTT ATT GAT GAT AAG GAA GCT AAA AAA CGG CGC GCC GCT CTA AGC CAA GAA GCG GAT TTT TAT GGT GCG ATG GAT GGC GCG TCT AAA TTT (SEQ ID NO:3).

The conditions of high stringency referred to above are the following: the hybridization is carried out at 42° C. in the presence of 50% formamide in a 2×SSC buffer containing 0.1% SDS (1×SSC corresponds to 0.15 M NaCl plus 15 mM sodium citrate—pH 7.0). The washings are carried out at 68° C., for example twice during a period of one hour, using 2×SSC plus 0.1% SDS.

A nucleotide sequence which is particularly interesting in accordance with the invention is the sequence of the flbA gene corresponding to the sequence of nucleotides (SEQ ID NO:6) depicted in FIG. 2, or to a nucleotide sequence which hybridizes, under conditions of high stringency, with the abovementioned sequence.

According to another embodiment of the invention, the nucleotide sequence which is the subject-matter of the present application is characterized in that it encodes a protein having the amino acid sequence, (SEQ ID NO:7) depicted in FIG. 2 or an amino acid sequence possessing the same regulatory properties, with regard to the biosynthesis of the flagellar proteins of H. pylori, as the abovementioned sequence.

The invention also relates to a nucleotide sequence which corresponds to the previous definitions and which is modified by deletion, substitution or insertion of bases or of a fragment of a nucleotide sequence, such that:

either the flbA gene is no longer expressed in a host cell,
or the expression of the flbA gene in a host cell does not enable the A and B flagellins or the sheath which contains them to be biosynthesized and, if this is the case, does not enable the H. pylori anchoring protein or the hook, to be synthesized.

The modification to which the nucleotide sequence of the invention is subjected should be such that it is irreversible and, in particular, that it remains irreversible when this sequence is recombined with the flbA gene which is present in a bacterium which is transformed with a nucleotide sequence which is modified in this manner. This recombination is, for example, of the "double crossing over" type. Preferably, the modification of the nucleotide sequence should not involve any substantial modification—after replacement, by this modified sequence, of the corresponding fragment of the normal flbA gene in a given H. pylori strain—of the functions of the neighbouring genes.

Also included within the scope of the invention are nucleotide sequences which constitute a fragment of the flbA gene meeting the above criteria. As examples, fragments which are the subject-matter of the invention consist of at least 6 nucleotide sequences, preferably at least 50, if not at least 100 nucleotides.

Such fragments are, for example, selected either on account of their specific flbA gene character or because they belong to conserved regions of several genes encoding proteins of the LcrD/FlbP family.

Figure 1B:
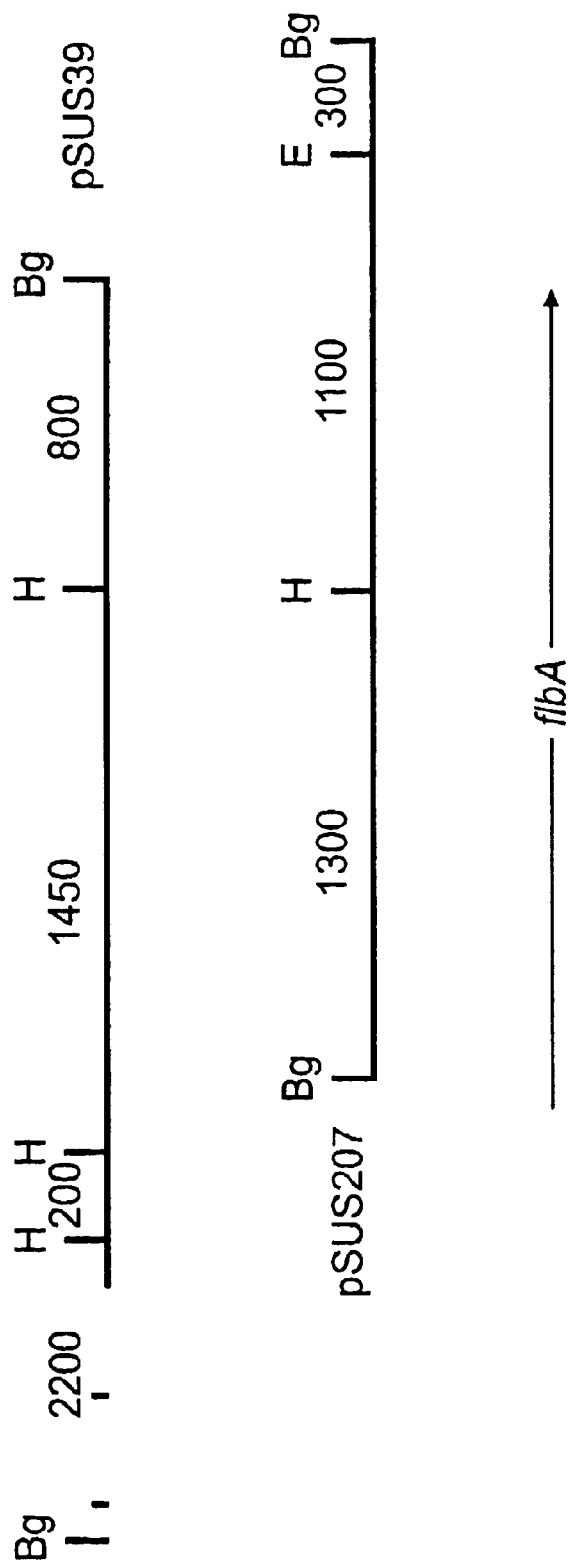

According to another embodiment, the invention is also directed towards the fragments of the flbA gene which are delimited by the restriction sites which are present in the gene. Some of these sites are defined, by way of example, in FIG. 1B.

Another fragment according to the invention is a fragment of at least 1000 bp which is derived from any region of the flbA gene and which preferably includes a restriction site or is capable of accommodating a restriction site.

Other nucleotide sequences of the invention are, for example, recombinant nucleic acids which comprise a nucleotide sequence such as those which have bee described above, itself modified by the insertion of a cassette containing a marker, for example a gene for resistance to an antibiotic or a gene for resistance to a heavy metal such as described in Application FR 9406202, which was filed on May 20, 1994.

Thus, a cassette for resistance to kanamycin can be inserted. Various techniques can be used in this context and reference is made, in particular, to the paper of Labigne A. et al. (J. of Bacteriology, Vol. 170, 1988, p 1704–1708) and the paper of Labigne A. et al. (Res. Microbiol 1992, 143, 15–26).

The invention also relates to specific oligonucleotides from a previously defined nucleotide sequence, which oligonucleotides are characterized in that they possess one of the following sequences:

OLFlbA-1: ATGCCTCGAGGTCGAAAAGCAAGATG (SEQ ID NO:1)

OLFlbA-2: GAAATCTTCATACTGGCAGCTCCAGTC (SEQ ID NO:2)

OLFlbA-7: CGGGATCCGTGGTTACTAATGGTTCTAC (SEQ ID NO:4)

OLFlbA-8: CGGGATCCTCATGGCCTCTTCAGAGACC (SEQ ID NO:5)

According to another embodiment, the invention relates to an amino acid sequence from the FlbA protein of H. pylori, which sequence is characterized in that it is encoded by a nucleotide sequence such as previously defined.

A specific amino acid sequence (SEQ ID NO:7) from the FlbA protein of H. pylori, is depicted in FIG. 2.

Thus, within the scope of the invention, the flbA gene and the protein expressed by this gene can be of interest, in particular for employment in immunogenic compositions or compositions used for vaccination.

The invention is also directed towards bacterial strains of Helicobacter pylori which possess an aflagellate phenotype, which phenotype results from the mutation, by substitution, addition and/or deletion of bases or of a nucleotide fragment, of the above-defined nucleotide sequences of the flbA gene involved in the regulation of the biosynthesis of the flagellar proteins of H. pylori.

This modification of the flbA gene makes it possible to obtain a strain of the aflagellate type, that in which no longer expresses the FlaA and FlaB proteins and which preferably no longer expresses the proteins of the sheath.

According to one embodiment of this bacterial strain, the strain which is obtained additionally lacks the hook protein of H. pylori.

Preferably, a bacterial strain which meets the abovementioned criteria is characterized in that it is obtained from the strain NG, which was deposited in the NCIMB on Jun. 26, 1992 under number NCIMB 40512.

By way of example, the invention relates to a recombinant aflagellate strain of H. pylori which is designated N6flbA- and was deposited in the NCIMB on Jun. 30, 1995 under the No. NCIMB 40747.

Such aflagellate strains of H. pylori are of particular interest for employment in serology and, as a consequence, for the in-vitro detection of an infection due to H. pylori. These strains are advantageously of the recombinant type.

In particular, these strains exhibit the advantage of enabling an infection due to H. pylori to be detected in vitro in a specific and sensitive manner. In other words, the invention advantageously enables an infection due to H. pylori to be detected specifically while avoiding, in particular, "false-positive" results, for example with bacterial strains such as Salmonella or Campylobacter.

Given that the strains of H. pylori of the aflagellate type, which have thus been defined, my also have other applications, for example may be employed in the preparation of vaccine compositions, there can be interest in preparing recombinant aflagellate bacterial strains which possess a second modification or mutation, for example an aflagellate bacterial strain can be prepared which is characterized in that it is additionally mutated in such a way that it produces an attenuated urease, or even no longer produces urease, with the mutation consisting, for example, of a mutation of the nucleotide sequence of one or more genes selected from among the genes ureA, ureB, ureC, ureD, ureE, ureF, ureG, ureH or ureI. The urease structural genes, designated urcA, ureB, ureC and ureD of urease, have been described in the publication (Labigne et al (1991) J. Bacteriol. 173: 1920–1931). The other genes have been described in Patent Application EP 0610322.

The bacterial strains of the invention may be employed as such or in extract form, and, in particular, the invention relates to a total bacterial strain extract which is obtained from the previously described strains.

Such a bacterial extract can be prepared by extracting with n-octyl glucoside. In this case, the preparation technique which is employed is that described by LELWALA-GURUGE J. (Scand. J. Infect. Dis. 1992, 24: 457–465).

Another bacterial extract can be obtained by extracting with PBS or glycine using the techniques described, respectively, by BAZILLOU M. et al (Clin. Diagn. Lab. Immuno., 1994, 1: 310–317) and AGUIRRE P. M. (Eur. J. Clin Microbiol. Infect. Dis., 1992 11: 634–639).

Within the scope of these applications, the invention relates to a composition for the in-vitro detection of an infection due to *H. pylori* in a sample of biological fluid obtained from a patient, in particular in a sample of serum, which composition includes, as the active principle, a bacterial strain of the invention or a bacterial extract in accordance with the description given above.

The biological samples which are used may be of any type and can, in particular, be any type of biological fluid, such as serum, saliva or urine, for example.

In the same way, the techniques which are employed for the detection are any techniques which involve reactions of the immunological type, in particular of the antigen/antibody type. For example, use is made of techniques such as Western blot, ELISA, etc.

The invention also relates, therefore, to a method for the in-vitro detection of an infection due to *H. pylori* in a sample of biological fluid taken from a patient, in particular in a sample of serum, which method comprises the steps of:

bringing the sample under test into contact with a bacterial strain according to the invention or with a bacterial extract as defined above, detecting an immunological reaction between the said bacterial strain and antibodies which are directed against *H. pylori* and which are present in the sample under test.

By way of example, an in-vitro detection on a biological sample in order to look for an infection due to *H. pylori* can be carried out by implementing the following steps:

plates are covered with the antigen which is used for the detection and which may be a pure or recombinant protein or else an aflagellate strain or a bacterial extract, in particular an NOG (n-octyl glucoside) extract of the N6flbA-strain (by way of example, the quantity of extract might be 3 μg/ml or the quantity of antigen might be 2 μg/ml), a range of negative and positive controls (the positive control being employed at differing dilutions) is used, and patient sera, which are diluted to 1/100, are tested in parallel (volume deposited, 100 μl), an incubation step is then carried out, for example at 37° C. for one hour, which step is followed by several successive washings and by a further incubation, for example at 37° C. for 1 hour, with a monoclonal conjugate (of the human IgG type labelled with peroxidase), which conjugate is employed at differing dilutions (for example at a dilution of 1/32000 in the case of an antigen and at a dilution of 1/64000 in the case of a bacterial extract), with the deposited volume being 100 μl, after the incubation with the monoclonal conjugate, several different washings are carried out (for Example 4) and the enzymic reaction is developed, in the dark and for 30 minutes, using "OPD+substrate". The enzymic reaction is then stopped by adding $H_2SO_4$, after which the optical densities, OD's, are read at 492 nm/620 nm.

The invention is furthermore directed to an immunogenic composition for obtaining antibodies against *H. pylori*, which composition is characterized in that it includes, as the active principle, a bacterial strain according to the invention or an extract of this bacterial strain.

According to one particular embodiment of the invention, an immunogenic composition for obtaining antibodies against *H. pylori* is characterized in that it includes an amino acid sequence from the FlbA protein.

Also included within the scope of the present invention is a vaccinating composition for obtaining antibodies which protect against an infection due to *H. pylori*, characterized in that it includes, as the active principle, a bacterial strain according to the invention or a bacterial extract according to the above definitions.

Another vaccinating composition for obtaining antibodies against an infection due to *H. pylori* is characterized in that it includes, as the active principle, antigens of the urease type, in particular antigens encoded by the genes ureA, ureB, ureC, or ureD and a protein having an amino acid sequence as defined above.

The invention also relates to monoclonal antibodies or polyclonal sera which are directed against a previously described amino acid sequence. These antibodies are obtained by techniques which are known per se, in particular by immunizing an animal with the chosen antigen, followed either by producing and recovering the antibodies which are produced and selecting those among them which specifically recognize *H. pylori*, or by preparing hybridomas, by fusing spleen cells from the previously immunized animal with myeloma cells, with these hybridomas then being cultured in order to obtain monoclonal antibodies, which are selected on the basis of the specificity with which they recognize the chosen *H. pylori* antigen.

Other monoclonal antibodies or polyclonal sera according to the invention are directed against an aflagellate *H. pylori* strain such as described in the preceding pages.

The invention furthermore relates to a composition for the in vitro detection of an infection due to *H. pylori* in a biological sample, which composition includes, as the active principle, monoclonal antibodies or a polyclonal serum which have been obtained against an *H. pylori* strain of the aflagellate phenotype according to the invention.

The invention also relates to nucleotide sequences, as the active principle of a medicament, which encode amino acid sequences according to the invention, which amino acid sequences are able to induce an immunogenic response in an animal or in a patient. A technique for employing nucleotide sequences as medicaments has been described by DONNELY et al 1995, Nature Medic. 1(6), pp. 583–587.

FIG. 1

1A: Restriction map of the plasmid pILL570 and of the mini transposon Tn3 containing the cassette of the gene for resistance to kanamycin.

1B: Linear restriction maps of the recombinant plasmids pSUS39 and pSUS207. The numbers which are shown correspond to the sizes of the restriction fragments, expressed in base pairs, H: HindIII; Bg: BglII. The presence of an asterisk indicates that the restriction site was modified during the cloning and that it is no longer recognized by the corresponding restriction enzyme.

FIG. 2: Nucleotide sequence (SEQ ID NO:6) of the flbA of *H. pylori* and the deduced amino acid sequence, given in one-letter code.

FIG. 3: Multiple alignment of the FlbA protein of *H. pylori* (SEQ ID NO:8) with five other members of the LcrDk/FlbF family (SEQ ID NOS:9–13). CjFlbA: *Campylobacter jejuni* FlbA (SEQ ID NO:9); CcFlbF: *Caulobacter crescentus*, FlbF (SEQ ID NO:10); YpLerD: *Xersinia pestis* LerD(SEQ ID NO:11); StInvA: *Salmonella typhimurium* InvA(SEQ ID NO:12); SfMxiA: *Shigella flexneri* MxiA (SEQ ID NO:13). The asterisks indicate the positions of the amino acids which are conserved in all the homologs of the LerD/FlbF family; the dots indicate the positions of the amino acids which are conserved in at least 5 out of the 6 homologous proteins; the conserved amino acid sequences which were used for synthesizing the degenerate oligonucleotides (OLFlbA-1 and OLFlbA-2) are underlined. Particular note should be taken of the degree of conservation of the N-terminal domain of these homologous proteins, which contrasts with the degree of variability of the hydrophilic domain of the C-terminal region.

Figure 4:
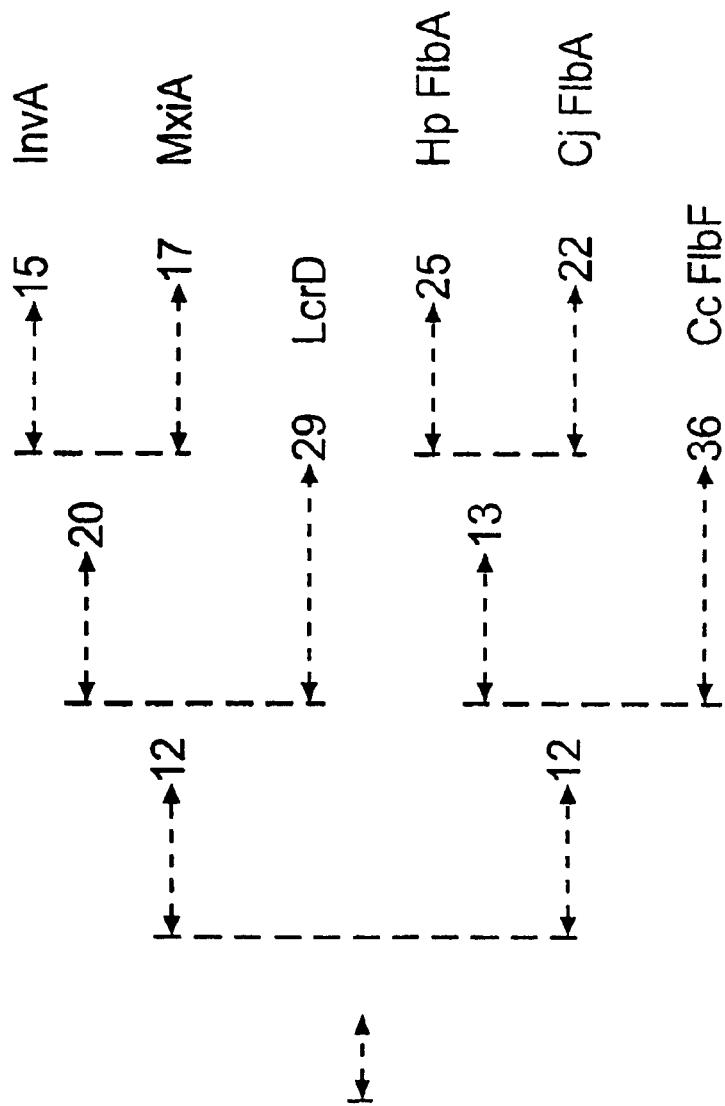

FIG. 4: Diagrammatic depiction of the phylogenetic tree of six proteins belonging to the LerD/FlbF family. The proteins which are involved in regulating the expression of mobility, i.e. FlbA of *H. pylori* (HpFlbA) and of *Campylobacter jejuni* (CjFlbA), and FlbF of *Caulobacter crescentus* (CcFlbF) form a branch which is distinct from that of the proteins involved in the secretion of virulence proteins (InvA, MxiA and LerD of *Salmonella, Shigella* and *Yersinis*, respectively). The numbers which are shown depict the relative evolutionary distance.

Figure 5:
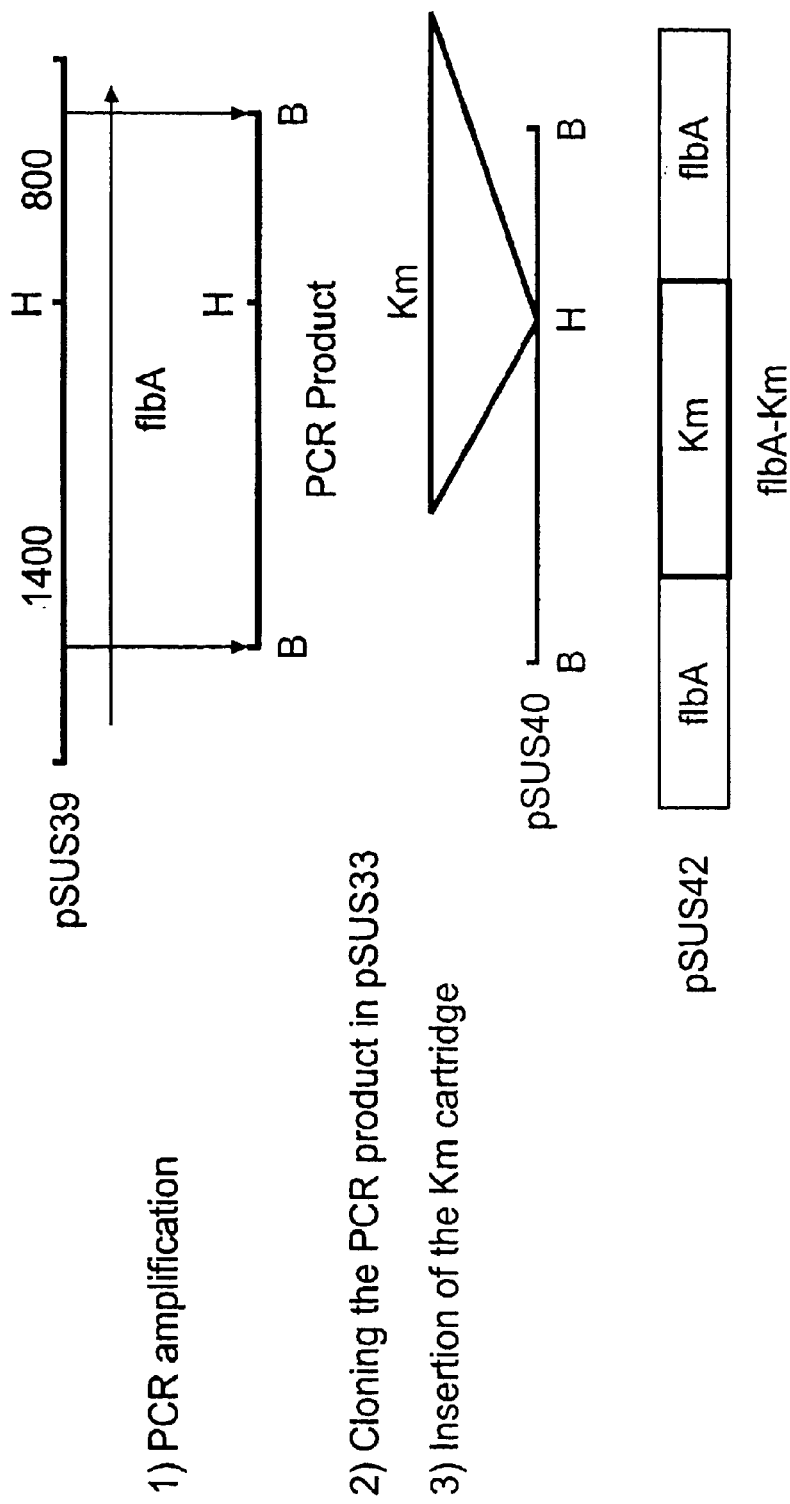

FIG. 5: Diagrammatic representation of the strategy which was followed for constructing the isogenic mutants of *H. pylori* strain N6, i.e. mutants in which the gene encoding the FlbA protein was inactivated by inserting a gene encoding for resistance to kanamycin.

Figure 6:
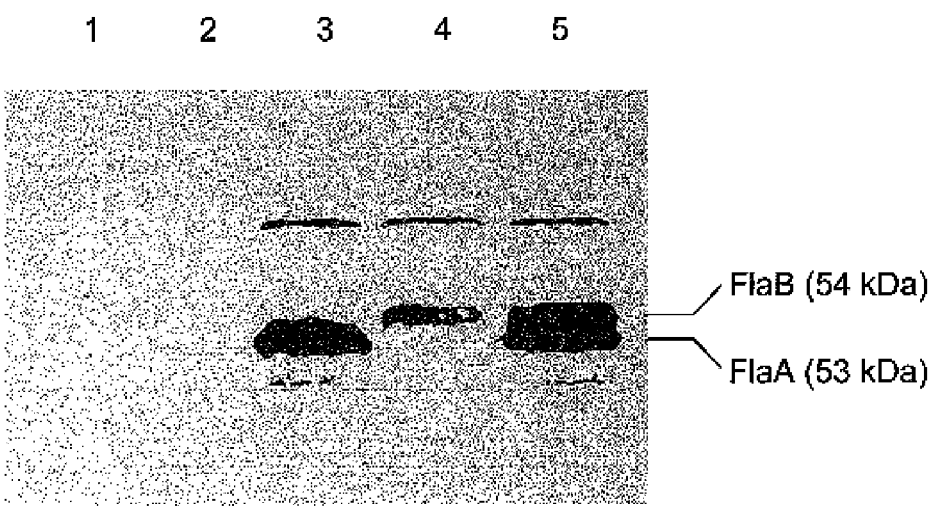
Figure 7:
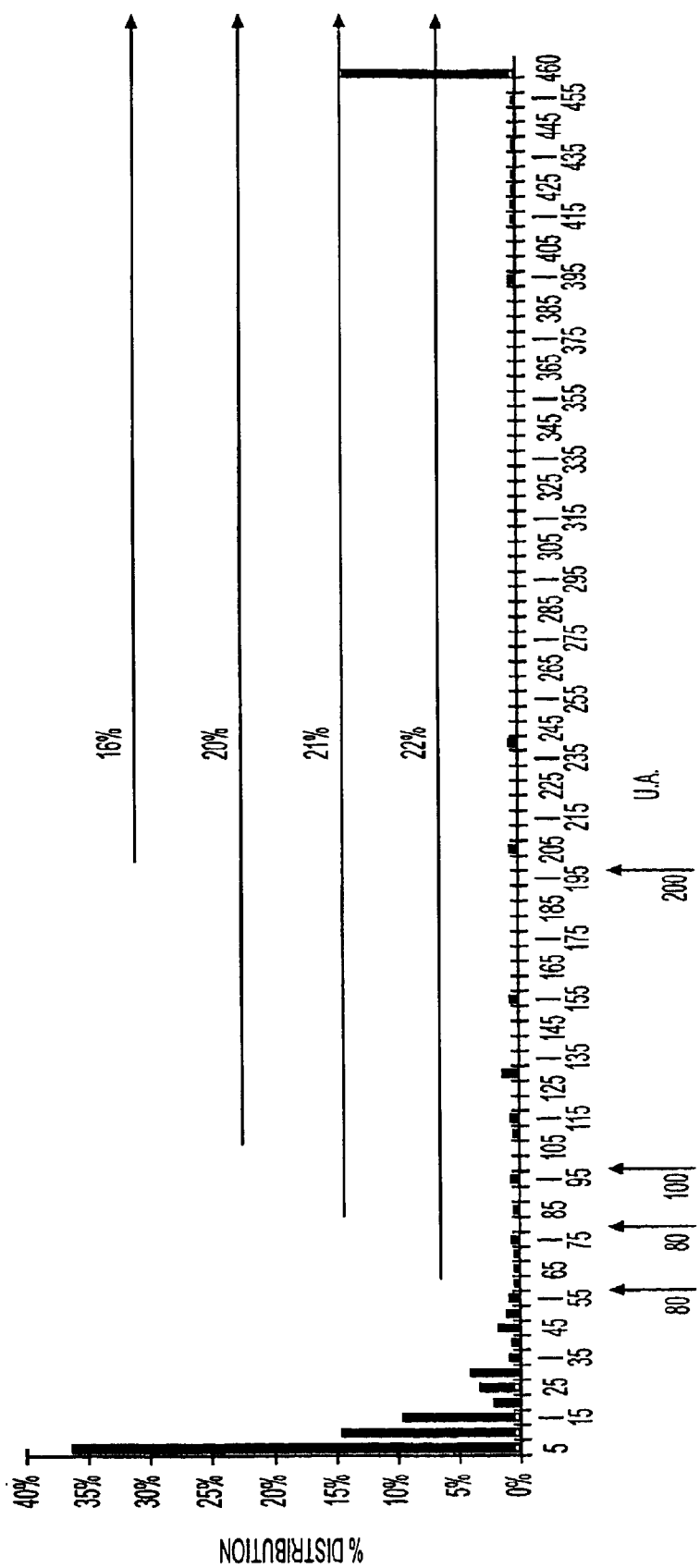
Figure 8:
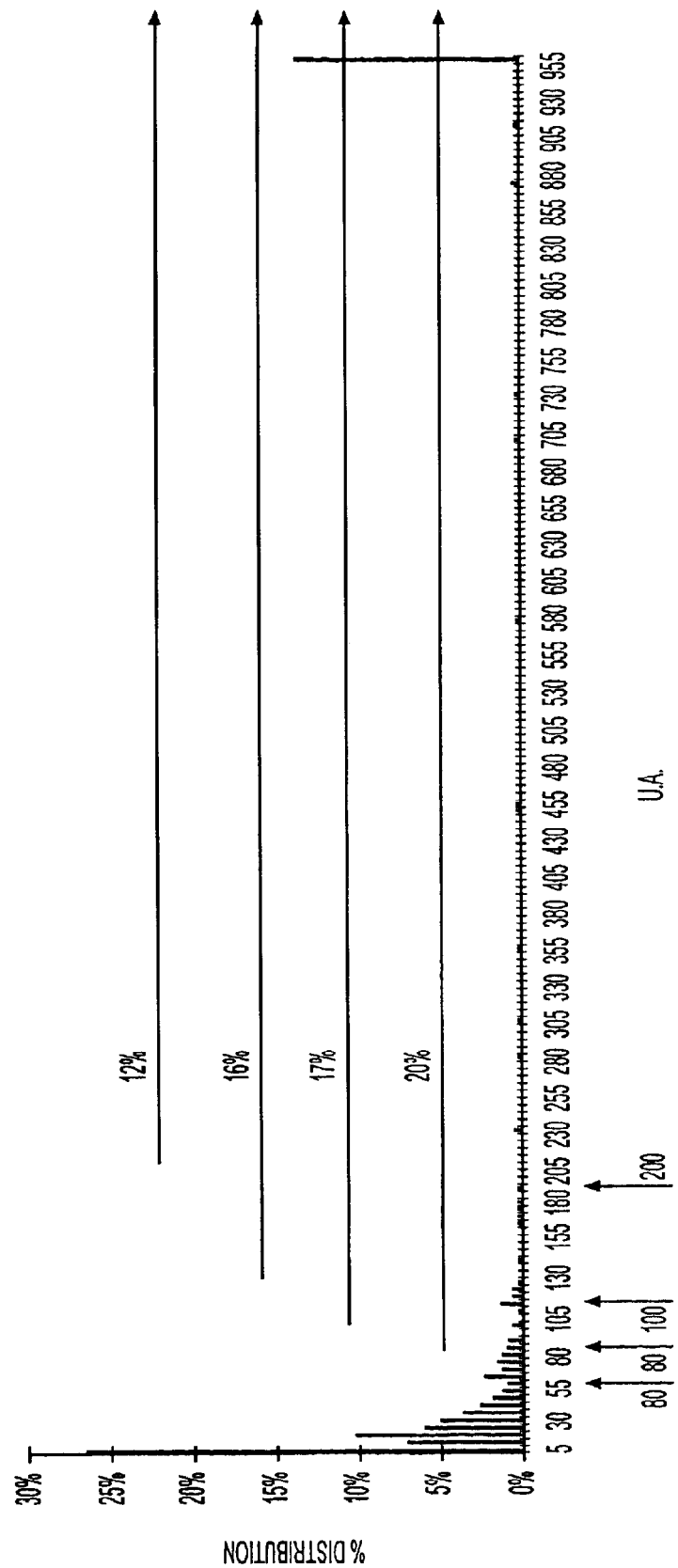
Figure 9:
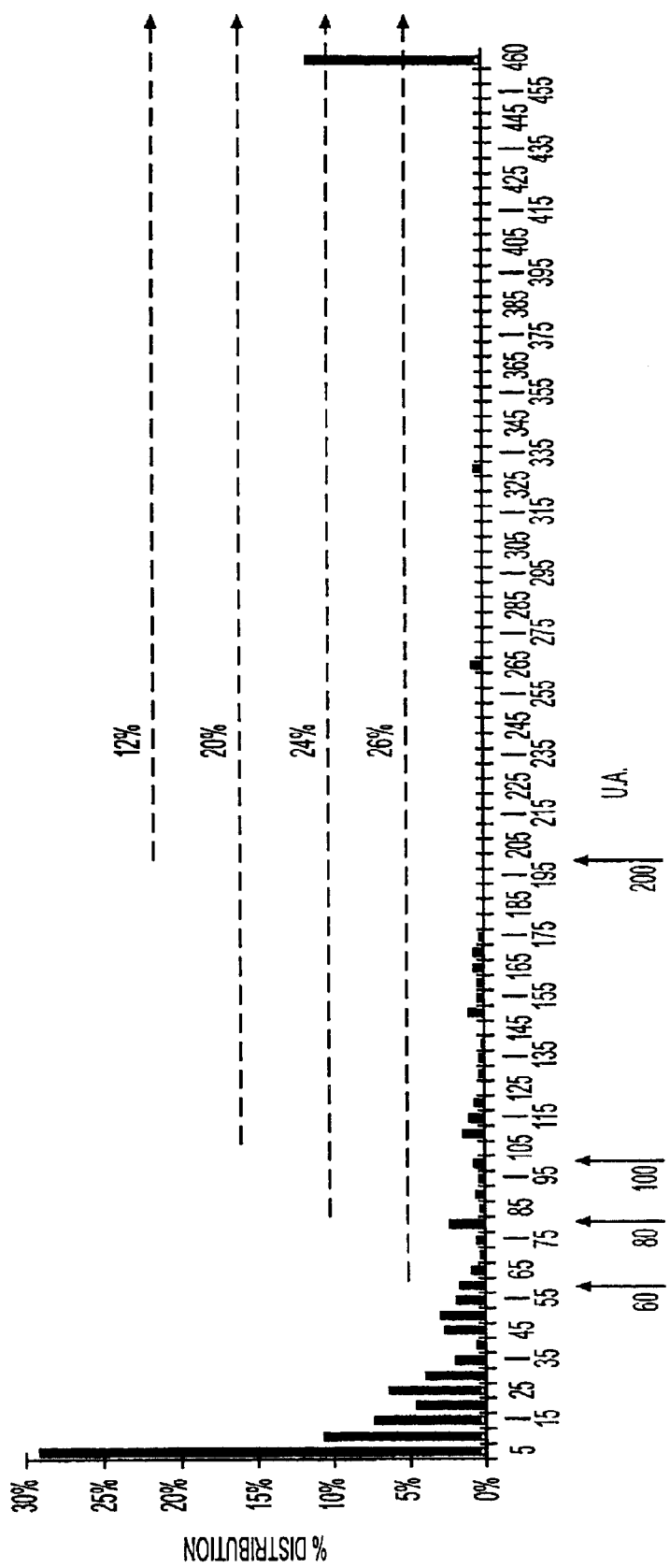
Figure 10:
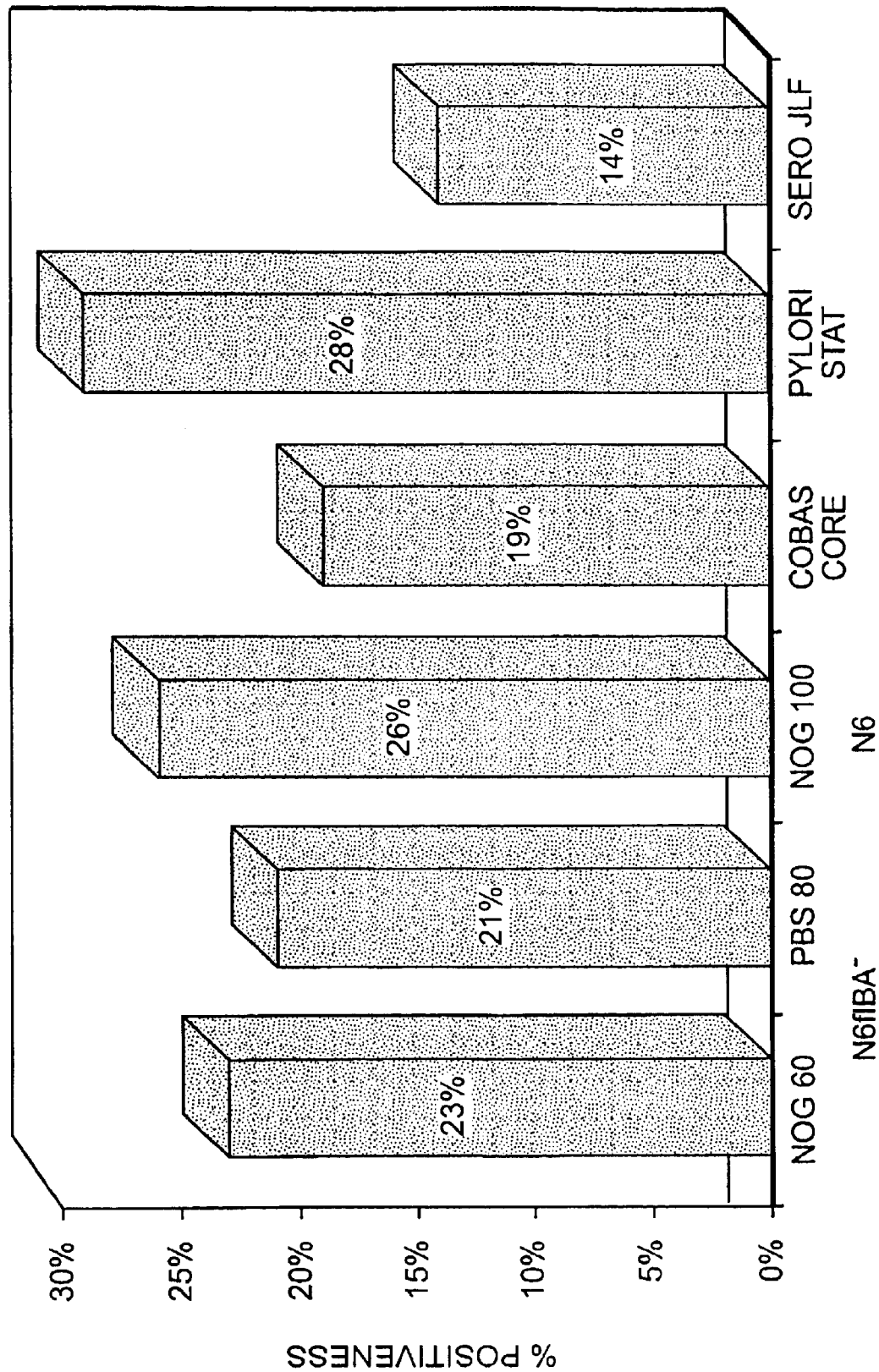
Figure 11:
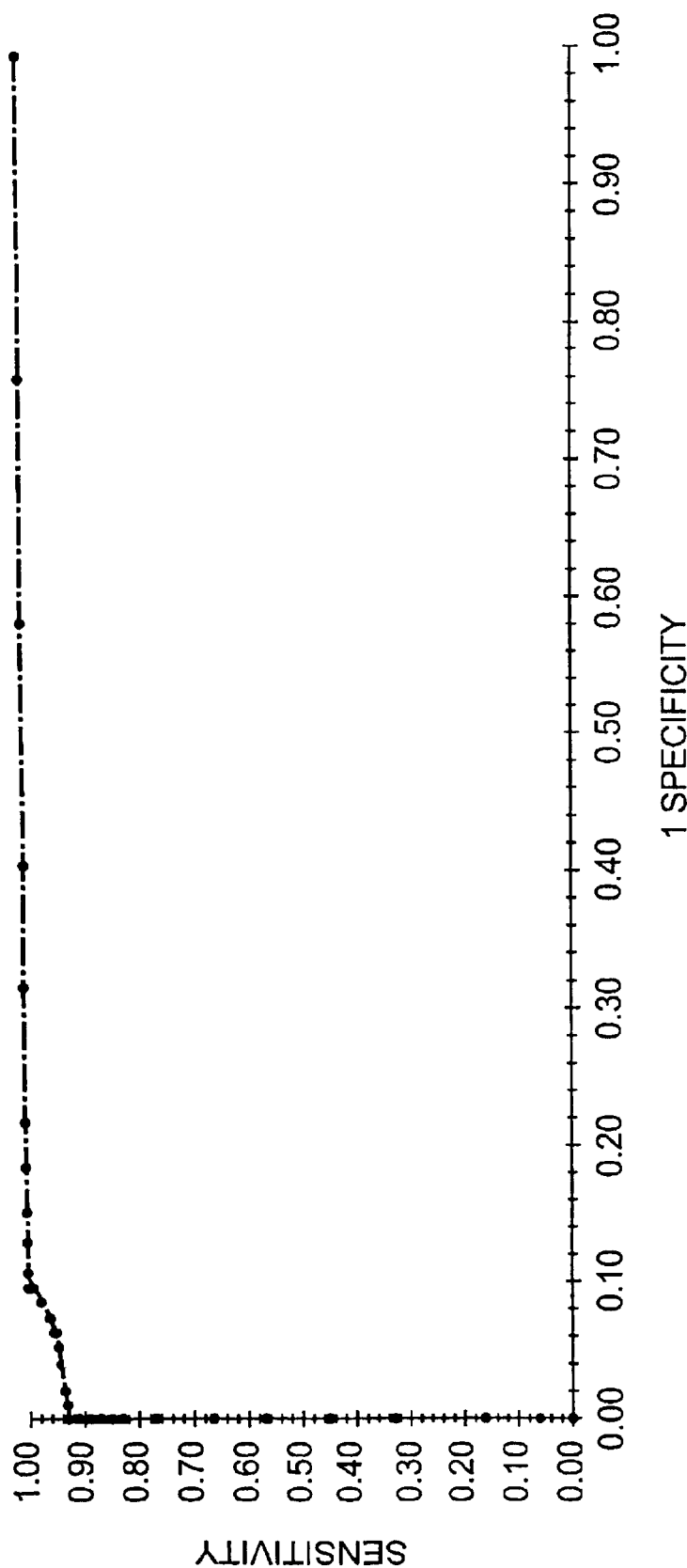

FIG. 6: Analysis by immoblotting (Western blot) of the proteins from an N6-flbA⁻ mutant using AK179 antiserum (3), which is specifically directed against flagella which have been purified from *H. pylori*: 1: N6-flbA mutant; 2: flaA/flaB double mutant; 3: flaB (B) mutant; 4: flaA (8) mutant; 5: wild-type N6 strain.

FIGS. 7 to 11: Comparative results from the serology carried out on *H. pylori*.

Figure 12:
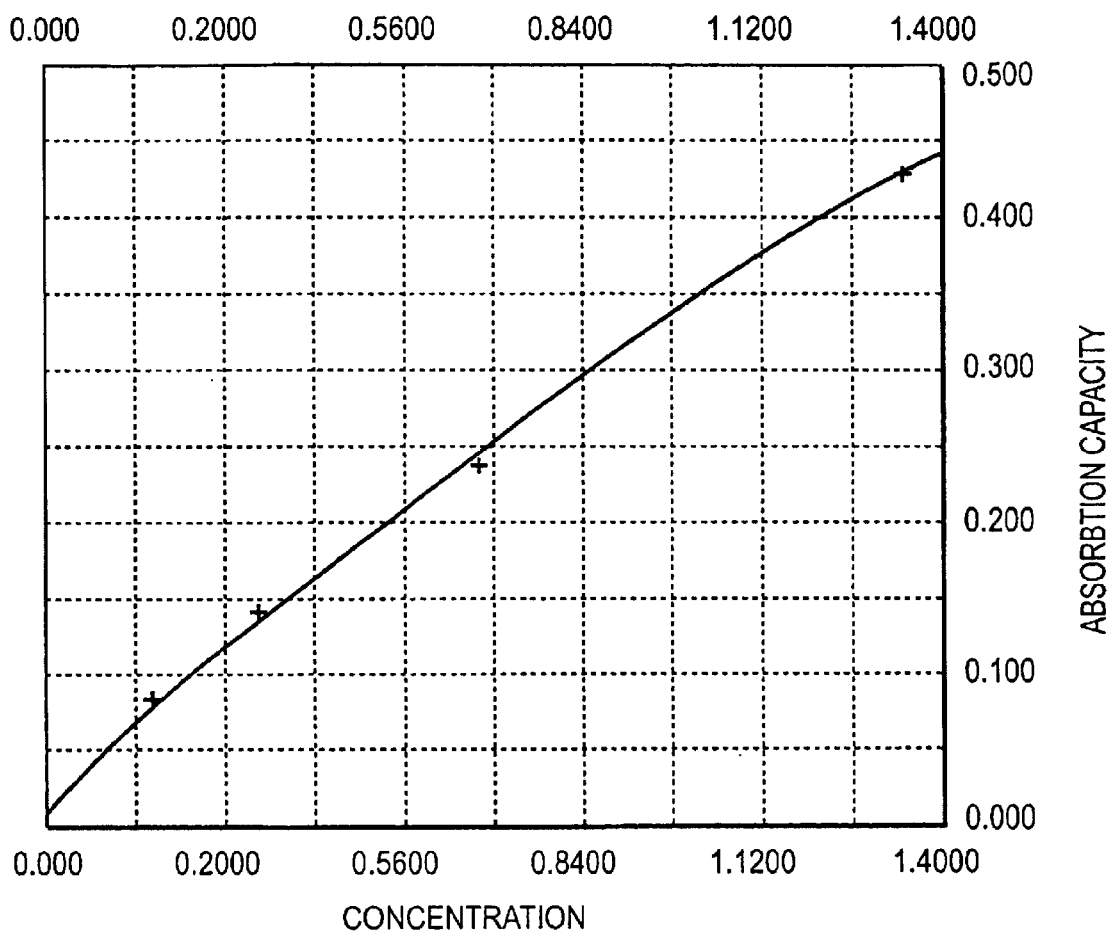
Figure 13A:
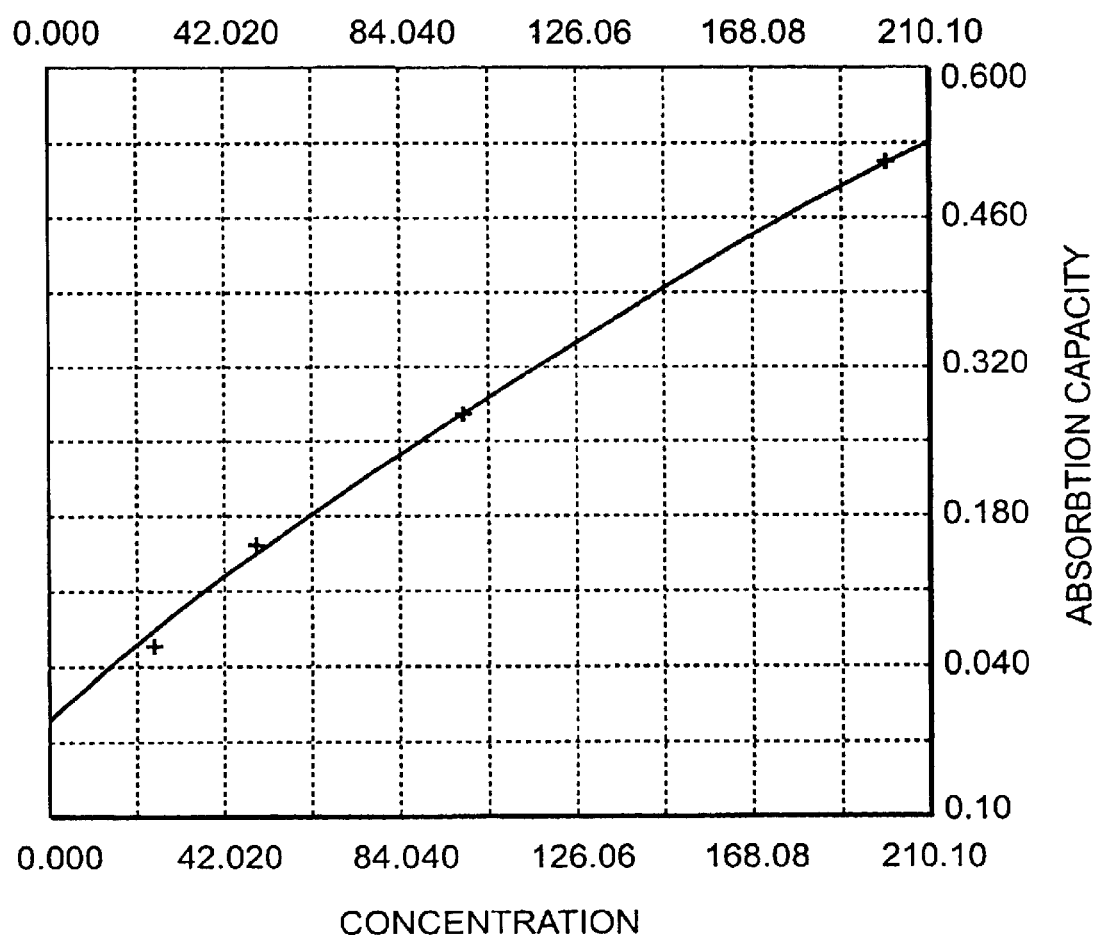

FIGS. 12 and 13: Extractions using the aflagellate strain N6flbA-: the extractions were carried out using glycine, PRS or NOG.

FIG. 12: The curves were constructed on the basis of the following data:

| STD# | CONC | NET ABS 750.0 | CALC CONC | DIFF | COEFFS: | MEAN: |
|---|---|---|---|---|---|---|
| 1 | 0.0000 | 0.0020 | −0.003 | 0.0080 | P2 = 2.0324 | −1.0356E-07 |
| 2 | 0.1660 | 0.0760 | 0.1721 | −0.006 | P1 = 2.2753 | |
| 3 | 0.3300 | 0.1400 | 0.3459 | −0.016 | PO = 0 | |
| 4 | 0.6650 | 0.2390 | 0.6474 | 0.0176 | | |
| 5 | 1.3300 | 0.4280 | 1.3336 | −0.004 | | |

S.D.: 0.0130

FIG. 13: Minimethod (BIO-RAD) protein assays Glycine: diluted 1/2; glucoside: diluted 1/10; supernatant 1: diluted 1/4; supernatant 2: not diluted.

The curves were constructed on the basis of the following data:

| STD# | CONC | NET ABS 750.0 | CALC CONC | DIFF | COEFFS: |
|---|---|---|---|---|---|
| 1 | 0.0000 | −0.003 | 1.5398 | −1.540 | P2 = 144.63 |
| 2 | 25.000 | 0.0600 | 21.861 | 3.1392 | P1 = 314.31 |
| 3 | 50.000 | 0.1470 | 51.810 | −1.810 | PO = 2.4815 |
| 4 | 100.00 | 0.2750 | 99.855 | 0.1454 | |
| 5 | 200.00 | 0.5090 | 199.94 | 0.0636 | |

EXAMPLES

I Identification of the flbA gene and preparation of aflgellate strains

Among the proteins which are known to play a role in regulating the expression of bacterial mobility, the proteins belonging to the recently identified LcrD/FlbF family, which include the LerD protein of the bacteria of the genus *Yersinia* (6), the InvA protein of *Salmonella* (2), MxiA of *Shigella* (1), FlbF of *Caulobacter crescentus* (7) and LfbA of *Campylobacter jejuni* (4) are proteins of interest. The LerD, InvA and Mxie proteins are involved in the regulation and/or the secretion of proteins which are associated with the virulence of the bacteria which express them, whereas the FlbF protein of *Caulobacter crescentus* and the FlbA protein of *Campylobacter jejuni* are involved in regulating the biosynthesis of the flagella and therefore involved in regulating mobility. The homologs of the LerD/FlbA family which are known to date possess very conserved domains, especially in the N-terminal part of these proteins, and it was therefore possible to use two of these conserved regions (MPGKQM, amino acids 151 to 156 of the LerD protein of *Xersinia*) and MDGAMKF (amino acids 189 to 195 of LerD) for defining two degenerate oligonucleotides (OLFlbA-1 and OLFlbA-2, Table 1), which were synthesized and which have served as nucleotide primers in the gene amplification experiments which were carried out on the chromosomal DNA of *Helicobacter pylori*. In this way, it was possible to amplify a fragment of 130 base pairs (bp), and determination of its nucleotide sequence demonstrated that this fragment encoded a segment of a protein which was very homologous to the proteins of the LerD/FlbF family. This amplified fragment was then labelled radioactively and used as a probe to screen an *H. pylori* cosmid library.

This fragment corresponds to the sequence contained between nucleotides 575 and 707 of the sequence depicted in FIG. 2 (SEQ ID NO:6).

One of the cosmids of the genomic library was identified as encoding the LerD/FlbF homolog of *H. pylori* and was then subjected to a partial digestion with Sau3A so as to construct a mini library (200 subclones) of the cosmid in vector pILL570, containing inserted fragments possessing a size of between 2 and 5 (kilobases). Vector pILL570 has been described in the paper by Labigne A. et al (Institut Pasteur/Elsevier Paris 1992. Rec. Microbiol. 1992, 143, 15–26). Its restriction map is given in FIG. 1A. These 200 clones were then hybridized to the 130 bp probe, and the clones which harboured plasmids pSUS39 and pSUS207 gave a positive hybridization. The linear restriction maps of these two recombinant plasmids are depicted in FIG. 13 and demonstrate that the two inserts of these clones have overlapping sequences. Determination of the nucleotide sequences of these two inserts revealed that neither of the two inserts contained the flbA gene in its entirety. The flbA gene of *H. pylori*, designated in this way due to its homology with the flbA gene of *Campylobacter jejuni*, corresponds to an open reading frame of 2196 nucleotides and encodes a protein having a calculated molecular mass of 80.1 kilodaltons. The nucleotide sequence (SEQ ID NO:6) of flbA and the amino acid sequence (SEQ ID NO:7) of FlbA are given in FIG. 2. Consensus sequences which are characteristic for promoter or terminator sequences have not been detected upstream and downstream of the open reading frame.

The FlbA protein exhibits similarities with the FlbA protein of *Campylobacter jejuni* and the FlbF protein of *Caulobacter crescentus*, both of which are involved in mobility (51.7% and 40.4% identity, respectively) whereas these percentages are lower with members of the LerD/FlbF protein family which are not involved in mobility: 32.8% identity with LerD from *Yersinia*, 30.5% with MxfA from *Shigella* and 29.3% with InvA from *Salmonella*. A multiple alignment of the amino acid sequences of these proteins (SEQ ID NOS:9–13) with that of *H. pylori* FlbA (SEQ ID NO:8) is given in FIG. 3. The most conserved regions of the homologs of the LerD/FlbF family are located in the N-terminal part of the proteins.

The phylogenetic evolution of the proteins involved in mobility (FlbA and FlbF) and that of the proteins involved in regulating the expression and/or the secretion of proteins associated with virulence is depicted diagrammatically by a phylogenetic tree (FIG. 4). Two distinct branches can be seen: *H. pylori* FlbA belongs unambiguously to the branch corresponding to the regulatory proteins involved in the biosynthesis of the flagella.

Construction and Characterization of Isogenic Mutants of *H. pylori* Which are Deficient in the Synthesis of the FlbA Protein.

A 1600 base pair fragment was amplified from plasmid pSUS39 using the oligonucleotides OLFlbA-7 and OLFlbA-8 (Table 1), each of which contains a BamHI restriction site at its 5' end. In its central region, this amplified fragment contains a unique HindIII restriction endonuclease site and was cloned into vector pSUS33, which is a derivative of plasmid pUC19 in which the HindIII site situated in the multiple cloning site has been deleted. In order to obtain pSUS33, plasmid pUC19 was restricted with HindIII; the sticky ends resulting from this restriction were treated with Klenow enzyme and T4 DNA polymerase in order to produce blunt ends; the resulting fragment was religated with T4 DNA ligase and introduced into *E. coli* DH5x in order to produce pSUS33. The recombinant plasmid resulting from the integration of the 1600 base pair fragment into pSUS33 was designated pSUS40; it was linearized with HindIII, its ends were blunt-ended and the SmaI kanamycin cassette, which was derived from plasmid pILL600 (Labigna A. et al, 1988, J. Bacter. 170, 1704–1708), was cloned into this unique site, resulting in plasmid pSUS42. Plasmid pSUS42 was then introduced by electroporation into the "N6" strain of *H. pylori*. The electroporation was carried out in accordance with the technique described by Perrero R. L. et al (Journal of Bacteriology, July 1992, pp. 4212–4217, Vol. 174, No. 13). The transformants which were obtained after selecting on a selective medium containing kanamycin (25 μg/ml) were then characterized genotypically and phenotypically. FIG. 5 shows a diagram of the procedure which was followed for the construction of mutants. Genotypic characterization of these mutants, by gene amplification and Southern hybridization, demonstrated that the genomes of the transformants which were resistant to kanamycin contained the resistance gene inserted in the middle of the flbA gene and that there had therefore been an allelic replacement, by means of double crossing-over, of the wild-type copy of the flbA gene by the inactive flbA-Km copy, with the loss of the nucleotide sequences of the pSUS33 vector. Phenotypic characterization of the flbA⁻ mutants of *H. pylori* demonstrated that they were not mobile; furthermore, analysis of these mutants by electron microscopy revealed that there was a total absence of the flagellum elements and an absence of the flagellum sheath. The immunoblotting experiments (Western blots) which were carried out using antibodies directed against the proteins of the entire flagellum of *H. pylori* (FIG. 6) demonstrated that two peptide bands corresponding to the flagellar subunits FlaA and FlaB were absent, as was a band corresponding to a polypeptide of an apparent mass of 90 kilodaltons, which is a protein which has recently been identified by O'Toole and collaborators (5) as being the hook protein (or anchoring protein) of the flagellum (5).

Taken as a whole, these results suggest that the FlbA protein of *H. pylori* is essential for the biosynthesis of all the flagellar structures and that inactivation of the gene encoding this protein results in complete cessation of the synthesis of any structure entering into the formation of the flagellum and not in interruption of the export of the constituents of these structures.

TABLE 1

Oligonucleotides employed in this study

| Oligo-nucleotide | Position | Strand | Nucleotide Sequence |
|---|---|---|---|
| OLFlbA-1 | AS-151–156 (LcrD) | + | ATGCCTCGAGGTCGAAAAGCAAGATG (SEQ ID NO:1) |
| OLFlbA-2 | AS-189–195 (LcrD) | − | GAAATCTTCATACTGGCAGCTCCAGTC (SEQ ID NO:2) |
| OLFlbA-7 | 515–534 | + | CGGGATCCGTGGTTACTAATGGTTCTAC (SEQ ID NO:4) |
| OLFlbA-8 | 2092–2111 | − | CGGGATCCTCATGGCCTCTTCAGAGACC (SEQ ID NO:5) |

| Models studied | |
|---|---|
| 1) HspAmr1E | recombinant protein of 47.5 kD (HspA = 13 kD) A sensitivity of 41% and a specificity of 96% were obtained on the population termed population 1 of documented sera. |

-continued

| Models studied | |
|---|---|
| 2) N6flbA- | aflagellate strain of *Helicobacter pylori* 3 extractions were carried out: - n-Octyl glucoside - PBS - Glycine For the time being, the extraction with n-octyl glucoside. (NOG) appears to be the best. |
| 3) -N6 | corresponding wild-type strain An extraction was carried out with n-octyl glucoside. |

A second population of sera was employed (population II). This population consists of some one hundred sera which are well documented from the clinical, endoscopic, histological, bacteriological and anatomopathological points of view. It was this population II which was used to assess the performances of the different models under study. Five different populations were tested.

5 populations of tested sera:
  300 ordinary sera (FNTS)
  18 sera which were positive by WHITTAKER serology (CBMS)
  92 well documented sera termed sera of population II
  87 sera which were documented from the bacteriological and anatomopathological points of view and which were termed sera of population I.
  23 sera exhibiting cross reactions:
    10 anti-Legionella positive sera
    10 anti-Chlamydia positive sera
    3 anti-Campylobacter positive sera Two competing kits, which bibliographic studies indicated were effective, were tested in parallel.

2 tested commercial kits:
  Cobas Core (ROCHE)
  Pylori Stat (WHITTAKER)

Results

The Ordinary Sera (FNTS) (FIGS. 8 to 11, Table 2)

300 sera were taken through the following models:
  Hsp A malE
  N6 flBA-
  N6

The epidemiological studies give seroprevalences, in France, of between 20 and 25%. The distribution of 300 blood donor sera was studied and the prevalence of positivity was calculated for different threshold values in order to validate the threshold value which was previously defined using the CBMS serum library (WHITTAKER serology).

This study enables the different tests to be compared using the same seroprevalence.

The first 43 sera were also taken through the following models:
  Cobas Core (ROCHE)
  Pylori Stat (WHITTAKER)
  serology known as JLF serology (ELISA test, based on an aqueous extract of several bacterial strains)

The results are expressed in arbitrary units and for different threshold values; a positive result is written as 1 and a negative result is written as 0.

On comparing these 43 sera in different tests, it can be observed that:
  the aflagellate strain N6flbA- and the Cobas Core test (Roche) give comparable seroprevalences of the order of 20%.
  HspA gives a very low seroprevalence (7%), which suggests a lack of sensitivity in view of the subsequent results.
  the JLF serology appears to be very specific since the seroprevalence is only 14%, considering the subsequent results.
  the Pylori Stat test (Whittaker) gives a high seroprevalence (29%), which might indicate a lack of specificity or a threshold value which is too low.

TABLE 2A

Comparison of 43 FNTS sera with regard to:

| No. | HspA | 150 | C50 + H | C30 + H | C. Core | 8 | P. Stat | 0.35 | N6flBA- PBS | 100 | 80 | 60 | NOG | 100 | 80 | 60 | JLF Scro. | 0.30 | N6 NOG | 100 |
|---|---|---|---|---|---|---|---|---|---|---|---|---|---|---|---|---|---|---|---|---|
| 1 | 0 | 0 | 1 | 1 | 170 | 1 | 0.70 | 1 | 3390 | 1 | 1 | 1 | 3105 | 1 | 1 | 1 | 0.75 | 1 | >928 | 1 |
| 2 | 0 | 0 | 0 | 0 | 0 | 0 | 0.21 | 0 | 4 | 0 | 0 | 0 | 3 | 0 | 0 | 0 | 0.01 | 0 | 5 | 0 |
| 3 | 0 | 0 | 0 | 0 | 3 | 0 | 0.23 | 0 | 6 | 0 | 0 | 0 | 4 | 0 | 0 | 0 | 0.01 | 0 | 6 | 0 |
| 4 | 0 | 0 | 0 | 0 | 4 | 0 | 0.19 | 0 | 4 | 0 | 0 | 0 | 3 | 0 | 0 | 0 | 0.02 | 0 | 4 | 0 |
| 5 | 0 | 0 | 0 | 0 | 3 | 0 | 0.28 | 0 | 12 | 0 | 0 | 0 | 6 | 0 | 0 | 0 | 0.08 | 0 | 27 | 0 |
| 6 | 1 | 0 | 0 | 0 | 2 | 0 | 0.17 | 0 | 0 | 0 | 0 | 0 | 0 | 0 | 0 | 0 | 0.01 | 0 | 0 | 0 |
| 7 | 2 | 0 | 0 | 0 | 3 | 0 | 0.32 | 0 | 41 | 0 | 0 | 0 | 36 | 0 | 0 | 0 | 0.02 | 0 | 13 | 0 |
| 8 | 79 | 0 | 0 | 0 | 137 | 1 | 0.57 | 1 | 3391 | 1 | 1 | 1 | 3109 | 1 | 1 | 1 | 1.43 | 1 | >928 | 1 |
| 9 | 0 | 0 | 0 | 0 | 3 | 0 | 0.35 | 1 | 23 | 0 | 0 | 0 | 21 | 0 | 0 | 0 | 0.05 | 0 | 16 | 0 |
| 10 | 0 | 0 | 0 | 0 | 1 | 0 | 0.34 | 0 | 26 | 0 | 0 | 0 | 14 | 0 | 0 | 0 | 0.02 | 0 | 31 | 0 |
| 11 | 0 | 0 | 0 | 0 | 3 | 0 | 0.23 | 0 | 61 | 0 | 0 | 1 | 33 | 0 | 0 | 0 | 0.00 | 0 | 77 | 0 |
| 12 | 0 | 0 | 0 | 0 | 0 | 0 | 0.19 | 0 | 0 | 0 | 0 | 0 | 0 | 0 | 0 | 0 | 0.02 | 0 | 0 | 0 |
| 13 | 0 | 0 | 0 | 0 | 1 | 0 | 0.19 | 0 | 51 | 0 | 0 | 0 | 28 | 0 | 0 | 0 | 0.02 | 0 | 57 | 0 |
| 14 | 0 | 0 | 0 | 0 | 3 | 0 | 0.25 | 0 | 4 | 0 | 0 | 0 | 4 | 0 | 0 | 0 | 0.02 | 0 | 11 | 0 |
| 15 | 1 | 0 | 0 | 0 | 3 | 0 | 0.27 | 0 | 4 | 0 | 0 | 0 | 3 | 0 | 0 | 0 | 0.02 | 0 | 7 | 0 |
| 16 | 0 | 0 | 0 | 0 | 0 | 0 | 0.37 | 1 | 62 | 0 | 0 | 1 | 51 | 0 | 0 | 0 | 0.05 | 0 | 97 | 0 |
| 17 | 0 | 0 | 0 | 0 | 1 | 0 | 0.22 | 0 | 5 | 0 | 0 | 0 | 2 | 0 | 0 | 0 | 0.03 | 0 | 13 | 0 |
| 18 | 0 | 0 | 0 | 0 | 1 | 0 | 0.25 | 0 | 13 | 0 | 0 | 0 | 8 | 0 | 0 | 0 | 0.00 | 0 | 18 | 0 |
| 19 | 0 | 0 | 0 | 0 | 0 | 0 | 0.27 | 0 | 4 | 0 | 0 | 0 | 4 | 0 | 0 | 0 | 0.05 | 0 | 15 | 0 |
| 20 | 0 | 0 | 0 | 0 | 1 | 0 | 0.21 | 0 | 23 | 0 | 0 | 0 | 12 | 0 | 0 | 0 | 0.01 | 0 | 31 | 0 |
| 21 | 0 | 0 | 0 | 0 | 18 | 1 | 0.46 | 1 | 54 | 0 | 0 | 0 | 204 | 1 | 1 | 1 | 0.24 | 0 | 331 | 1 |

TABLE 2B

Comparison of 43 FNTS sera with regard to:

| No. | HspA | C50 + 150 | C30 + H | C. H | Core | 8 | P. Stat | 0.35 | PBS | 100 | N6flBA- 80 | 60 | NOG | 100 | 80 | 60 | JLF Scro. | 0.30 | N6 NOG | 100 |
|---|---|---|---|---|---|---|---|---|---|---|---|---|---|---|---|---|---|---|---|---|
| 22 | 1 | 0 | 0 | 0 | 1 | 0 | 0.43 | 1 | 13 | 0 | 0 | 0 | 40 | 0 | 0 | 0 | 0.05 | 0 | 21 | 0 |
| 23 | 0 | 0 | 0 | 1 | 25 | 1 | 0.49 | 1 | 285 | 1 | 1 | 1 | 296 | 1 | 1 | 1 | 0.37 | 1 | >928 | 1 |
| 24 | 9 | 0 | 1 | 1 | 125 | 1 | 0.65 | 1 | 3390 | 1 | 1 | 1 | 3100 | 1 | 1 | 1 | 1.47 | 1 | >928 | 1 |
| 25 | 0 | 0 | 3 | 0 | 0 | 0 | 0.20 | 0 | 34 | 0 | 0 | 0 | 20 | 0 | 0 | 0 | 0.01 | 0 | 51 | 0 |
| 26 | 0 | 0 | 0 | 0 | 2 | 0 | 0.29 | 0 | 97 | 0 | 1 | 1 | 60 | 8 | 0 | 0 | 0.04 | 0 | 105 | 1 |
| 27 | 0 | 0 | 1 | 1 | 10 | 1 | 0.33 | 0 | 265 | 1 | 1 | 1 | 239 | 1 | 1 | 1 | 0.07 | 0 | 359 | 1 |
| 28 | 0 | 0 | 1 | 1 | 7 | 0 | 0.21 | 0 | 26 | 0 | 0 | 0 | 14 | 0 | 0 | 0 | 0.05 | 0 | 27 | 0 |
| 29 | 3 | 0 | 0 | 0 | 6 | 0 | 0.20 | 0 | 3 | 0 | 0 | 0 | 2 | 0 | 0 | 0 | 0.01 | 0 | 0 | 0 |
| 30 | 1 | 0 | 0 | 0 | 2 | 0 | 0.23 | 0 | 3 | 0 | 0 | 0 | 3 | 0 | 0 | 0 | 0.01 | 0 | 4 | 0 |
| 31 | 0 | 0 | 0 | 0 | 1 | 0 | 0.21 | 0 | 0 | 0 | 0 | 0 | 1 | 0 | 0 | 0 | 0.03 | 0 | 0 | 0 |
| 32 | 0 | 0 | 0 | 0 | 2 | 0 | 0.31 | 0 | 24 | 0 | 0 | 0 | 15 | 0 | 0 | 0 | 0.05 | 0 | 30 | 0 |
| 33 | 0 | 0 | 0 | 0 | 1 | 0 | 0.23 | 0 | 14 | 0 | 0 | 0 | 8 | 0 | 0 | 0 | 0.02 | 0 | 8 | 0 |
| 34 | 0 | 0 | 0 | 0 | 3 | 0 | 0.23 | 0 | 0 | 0 | 0 | 0 | 1 | 0 | 0 | 0 | 0.00 | 0 | 2 | 0 |
| 35 | 1293 | 1 | 1 | 1 | 170 | 1 | 0.84 | 1 | 463 | 1 | 1 | 1 | 3103 | 1 | 1 | 1 | 0.96 | 1 | >928 | 1 |
| 36 | 0 | 0 | 0 | 0 | 4 | 0 | 0.36 | 1 | 42 | 0 | 0 | 0 | 32 | 0 | 0 | 0 | 0.04 | 0 | 68 | 0 |
| 37 | 0 | 0 | 0 | 0 | 5 | 0 | 0.22 | 0 | 110 | 1 | 1 | 1 | 109 | 1 | 1 | 1 | 0.02 | 0 | 227 | 1 |
| 38 | 13 | 0 | 0 | 0 | 4 | 0 | 0.47 | 1 | 77 | 0 | 0 | 1 | 68 | 0 | 0 | 1 | 0.07 | 0 | 108 | 1 |
| 39 | 1 | 0 | 0 | 0 | 4 | 0 | 0.34 | 0 | 23 | 0 | 0 | 0 | 13 | 0 | 0 | 0 | 0.05 | 0 | 34 | 0 |
| 40 | 0 | 0 | 0 | 0 | 2 | 0 | 0.19 | 0 | 5 | 0 | 0 | 0 | 8 | 0 | 0 | 0 | 0.02 | 0 | 4 | 0 |
| 41 | 0 | 0 | 0 | 0 | 0 | 0 | 0.24 | 0 | 46 | 0 | 0 | 0 | 23 | 0 | 0 | 0 | 0.05 | 0 | 66 | 0 |
| 42 | 0 | 0 | 0 | 0 | 170 | 1 | 0.59 | 1 | 3388 | 1 | 1 | 1 | 3104 | 1 | 1 | 1 | 1.47 | 1 | >928 | 1 |
| 43 | 0 | 0 | 1 | 1 | 3 | 0 | 0.19 | 0 | 7 | 0 | 0 | 0 | 5 | 0 | 0 | 0 | 0.04 | 0 | 8 | 0 |
| no.of | | 8 | 7 | | 8 | | | 12 | | 8 | 9 | 12 | | 9 | 9 | 10 | | 6 | | 11 |
| % of | 2% | 14% | 16% | | 19% | | | 29% | | 19% | 21% | 28% | | 21% | 21% | 23% | | 14% | | 26% |

The sera which are positive by WHITTAKER serology (CBMS) (Table 3)

Three sera were found to be positive only with the Pylori Stat test (Whittaker). They were not confirmed using any other test.

It may be supposed that this result is due to this test lacking specificity. If the Cobas Core test (Roche), which is one of the best which is currently on the market, is taken as the reference, we can compare our different models in relation to Cobas Core.

The aflagellate N6flbA- strain correlates perfectly with Cobas Core.

The 3 sera which are negative with Cobas Core are also negative with N6flbA-.

The 15 sera which are positive with Cobas Core are also positive with N6flbA-.

The wild-type N6 strain gives the same results as the aflagellate strain.

HspA also lacks sensitivity since 9 Cobas Core-positive sera are negative with HspA.

The 3 sera which are negative with Cobas Core are also negative with HspA.

TABLE 3

19 CBMS sera which are positive by WHITTAKER serology (Pylori Stat)

| No. of Serum | OD | HspA | 150 | C. Core | 8 | PBS | 80 | N6flBA- NOG | 60 | GLY | N6 NOG | 100 |
|---|---|---|---|---|---|---|---|---|---|---|---|---|
| 1 | 1.8 | 0 | 0 | 33 | 1 | 130 | 1 | 289 | 1 | 494 | 830 | 1 |
| 2 | 2.41 | 607 | 1 | >80 | 1 | 471 | 1 | 3257 | 1 | 6587 | >928 | 1 |
| 3 | 2.9 | 675 | 1 | 30 | 1 | 472 | 1 | 3263 | 1 | 1183 | >928 | 1 |
| 4 | 1.4 | 146 | 0 | 42 | 1 | 156 | 1 | 407 | 1 | 825 | 556 | 1 |
| 5 | 1 | 179 | 1 | 44 | 1 | 59 | 0 | 81 | 1 | 317 | 276 | 1 |
| 6 | 2.6 | 193 | 1 | >80 | 1 | 472 | 1 | 3260 | 1 | 1054 | >928 | 1 |
| A | 0.7 | 19 | 0 | 4 | 0 | 13 | 0 | 8 | 0 | 33 | 12 | 0 |
| B | 2.6 | 5 | 0 | >80 | 1 | 471 | 1 | 3255 | 1 | 6600 | >928 | 1 |
| C | 3.1 | 1352 | 1 | >80 | 1 | 470 | 1 | 3246 | 1 | 6582 | >928 | 1 |
| D | 1.3 | 3 | 0 | 18 | 1 | 121 | 1 | 506 | 1 | 448 | >928 | 1 |
| E | 0.6 | 7 | 0 | 1 | 0 | 23 | 0 | 45 | 0 | 150 | 0 | 0 |
| F | 2.1 | 0 | 0 | 15 | 1 | 139 | 1 | 3258 | 1 | 280 | >928 | 1 |
| G | 0.2 | 0 | 0 | 8 | 0 | 3 | 0 | 4 | 0 | 28 | 0 | 0 |
| H | 1.4 | 25 | 0 | 18 | 1 | 127 | 1 | 176 | 1 | 143 | 159 | 1 |
| I | 2.3 | 960 | 1 | >80 | 1 | | | | | | | |
| J | 1.9 | 5 | 0 | 38 | 1 | 91 | 1 | 117 | 1 | 57 | 101 | 1 |
| K | 1.38 | 4 | 0 | 52 | 1 | 88 | 1 | 182 | 1 | 167 | >928 | 1 |
| L | 2.98 | 855 | 1 | >80 | 1 | 471 | 1 | 586 | 1 | 943 | >928 | 1 |
| M | 2.86 | 0 | 0 | 51 | 1 | 471 | 1 | 3256 | 1 | 1200 | >928 | 1 |

The sera of population II 92 sera were selected with the sera dividing into 3 groups:

34: dyspeptic patients diagnosis of ulcer (duodenal or gastric) by endoscopy and histology presence of *Helicobacter pylori*, by culture and/or anatamopathologically; a rapid urea test was also carried out. This group will be termed Hp+/U+

27: dyspeptic patients differential diagnosis of ulcer (gastritis etc.) by endoscopy and histology presence of *Helicobacter pylori* by culture and/or anatamopathologically; a rapid urea test was also carried out. This group will be termed Hp+/U−

31: patients which are or are not dyspeptic normal gastroduodenum by endoscopy and histology absence of *Helicobacter pylori* by culture and anamatopathologically; a rapid urea test was also carried out. This group will be termed Hp−

The clinical, endoscopic, histological, bacteriological and anatomopathological findings are indicated for each patient. This well documented population enabled criteria of sensitivity and specificity to be defined.

HpA: A substantial lack of sensitivity, as observed with population I, is still noticed. The sensitivity is 59%, with a specificity of 100.

N6flbA: A sensitivity of 100% is confirmed for the n-octyl glucoside extract, with a specificity of 90%. This result is comparable to that obtained with the Roche Cobas Core test (98% sensitivity with a specificity of 94%).

N6: On population II, the wild-type strain is entirely comparable to the aflagellate strain. None of the 31 negative sera is positive with the wild-type strain; no cross reaction due to the flagellum was detected with this population II.

TABLE 4

Sera of population II
34 Hp+/U+ patients

| | | | | | | | | | | | | | | Aflagellate variant N6FIBA | | | | | | | | | |
|---|---|---|---|---|---|---|---|---|---|---|---|---|---|---|---|---|---|---|---|---|---|---|---|
| No. | Date | Age | Sex | Clinical | Endos. | UD/ UG | Histo-A | Giemsa | HP Cult | Ure | HP HspA | VS = 150 | PBS | VS = 80 | NOG | VS = 60 | N6 NOG | VS = 100 | C. COR | VS = 8 | P. STAT | VS = 0.19/0.27 | JLF | VS = 0.30 |
| 9 | Jul. 19, 1991 | 33 | 1 | dyspepsia | DU | 1 | G210 | 0 | 1 | 0 | 6 | 0 | 166 | 1 | 305 | 1 | >928 | 1 | 30 | 1 | 0.288 | 1 | 0.91 | 1 |
| 11 | Mar. 12, 1992 | 32 | 1 | dyspepsia | DU | 1 | G313 | 1 | 1 | 1 | 51 | 1 | >464 | 1 | 1000 | 1 | >928 | 1 | 55 | 1 | 0.359 | 1 | 1.03 | 1 |
| 13 | May 19, 1992 | 26 | 1 | dyspepsia | GU | 1 | G311 | 1 | 0 | 0 | 1530 | 1 | >464 | 1 | 1452 | 1 | >928 | 1 | >160 | 1 | 0.377 | 1 | 0.67 | 0 |
| 15 | Jul. 23, 1993 | 27 | 1 | dyspepsia | DU | 1 | G222 | 1 | 1 | 0 | 42 | 1 | 137 | 1 | 229 | 1 | 406 | 1 | 40 | 1 | 0.223 | 1 | 0.26 | 1 |
| 16 | Dec. 10, 1991 | 37 | 1 | dyspepsia | DU | 1 | G410 | 1 | 0 | 0 | 2135 | 1 | >464 | 1 | 870 | 1 | >928 | 1 | 80 | 1 | 0.399 | 1 | 1.14 | 1 |
| 17 | May 18, 1994 | 40 | 1 | perforation | DU | 1 | G230 | 1 | 0 | 0 | 14 | 0 | >464 | 1 | 676 | 1 | >928 | 1 | 62 | 1 | 0.302 | 1 | 1.12 | 1 |
| 18 | Dec. 16, 1992 | 22 | 1 | dyspepsia | DU | 1 | G222 | 1 | 0 | 1 | 16 | 0 | >464 | 1 | 1124 | 1 | >928 | 1 | >160 | 1 | 0.373 | 1 | 0.74 | 1 |
| 26 | Sep. 7, 1994 | 39 | 1 | dyspepsia | DU | 1 | G220 | 1 | 1 | 0 | 11 | 0 | 82 | 1 | 64 | 1 | 403 | 1 | 10 | 1 | 0.209 | 1 | 0.23 | 0 |
| 27 | Feb. 5, 1992 | 47 | 0 | dyspepsia | DU | 1 | G212 | 1 | 1 | 0 | 12 | 0 | 58 | 1 | 104 | 1 | 398 | 1 | 16 | 1 | 0.245 | 1 | 1.73 | 1 |
| 28 | Apr. 27, 1994 | 42 | 1 | GOR-A-GU | GDN | 1 | G320 | 1 | 1 | 1 | 7970 | 1 | >464 | 1 | 2344 | 1 | >928 | 1 | >180 | 1 | 0.477 | 1 | 1.51 | 1 |
| 29 | Jun. 24, 1994 | 57 | 1 | A(illegible) dysphagia | GDN-B | 1 | G222 | 0 | 1 | 0 | 805 | 1 | >464 | 1 | 2360 | 1 | >928 | 1 | >180 | 1 | 0.463 | 1 | | 1 |
| 33 | Nov. 4, 1991 | 60 | 1 | dyspepsia | DU | 1 | G231 | 1 | 1 | 1 | 663 | 1 | >464 | 1 | 2720 | 1 | >928 | 1 | >180 | 1 | 0.505 | 1 | 0.97 | 1 |
| 38 | Sep. 3, 1990 | 46 | 1 | dyspepsia | DU | 1 | G331F | 1 | 0 | 0 | 4580 | 1 | >464 | 1 | 2676 | 1 | >928 | 1 | >180 | 1 | 0.419 | 1 | 1.34 | 1 |
| 39 | Mar. 2, 1994 | 79 | 1 | AEG dyspepsia | GU | 1 | G212 | 1 | 1 | 1 | 422 | 1 | 240 | 1 | 436 | 1 | | 1 | 14 | 1 | 0.253 | 1 | 0.88 | 1 |
| 43 | Jan. 13, 1994 | 67 | 0 | AEG | DU | 1 | G111 | 1 | 0 | 1 | 108 | 0 | 78 | 1 | 75 | 1 | 379 | 1 | 14 | 1 | 0.204 | 1 | 0.52 | 1 |
| 44 | Jul. 1, 1994 | 60 | 0 | dyspepsia | DU | 1 | G321 | 1 | 1 | 1 | 9 | 0 | >464 | 1 | 2876 | 1 | >928 | 1 | >160 | 1 | 0.485 | 1 | 1.69 | 1 |
| 48 | Feb. 2, 1995 | 69 | 1 | dyspepsia | UD | 1 | G120 | 1 | 0 | 1 | 39 | 0 | 123 | 1 | 304 | 1 | >928 | 1 | 100 | 1 | 0.274 | 1 | 1.50 | 1 |
| 52 | Oct. 26, 1994 | 45 | 1 | dyspepsia AU | GDN | 1 | G221F | 1 | 1 | 1 | 6 | 0 | 164 | 1 | 368 | 1 | 595 | 1 | 16 | 1 | 0.257 | 1 | 0.22 | 0 |
| 56 | Sep. 5, 1994 | 72 | 0 | dyspepsia | UD | 1 | G233 | 0 | 0 | 0 | 1620 | 1 | >464 | 1 | 1704 | 1 | >928 | 1 | 65 | 1 | 0.389 | 1 | 1.21 | 1 |
| 60 | Jun. 19, 1991 | 40 | 1 | dyspepsia | UG | 1 | G333 | 1 | 1 | 1 | 3690 | 1 | 123 | 1 | 3192 | 1 | >928 | 1 | >160 | 1 | 0.524 | 1 | 6.28 | 1 |
| 64 | Nov. 7, 1994 | 37 | 1 | urt. | UD | 1 | G323 | 1 | 1 | 1 | 7 | 0 | 173 | 1 | 980 | 1 | >928 | 1 | 40 | 1 | 0.362 | 1 | 0.39 | 1 |
| 65 | Dec. 15, 1994 | 41 | 0 | dyspepsia perforation | UD | 1 | G211F | 1 | 0 | 1 | 3 | 0 | 100 | 1 | 310 | 1 | >928 | 1 | 86 | 1 | 0.318 | 1 | 0.33 | 1 |
| 70 | Apr. 29, 1993 | 47 | 1 | dyspepsia-melaena | UD | 1 | G110 | 1 | 0 | 1 | 8 | 0 | 164 | 1 | 384 | 1 | 804 | 1 | 23 | 1 | 0.256 | 1 | 1.13 | 1 |
| 71 | Mar. 29, 1993 | 39 | 1 | dyspepsia | UD | 1 | G221 | 1 | 0 | 1 | 107 | 0 | 97 | 1 | 121 | 1 | 202 | 1 | 23 | 1 | 0.183 | 1 | 0.14 | 0 |
| 76 | Jun. 9, 1993 | 38 | 1 | dyspepsia | UD | 1 | G121* | 1 | 0 | 0 | 313 | 1 | 140 | 1 | 726 | 1 | 785 | 1 | 37 | 1 | 0.296 | 1 | 0.25 | 0 |
| 78 | May 12, 1993 | 49 | 0 | dyspepsia AU | GDN | 1 | G220 | 1 | 0 | 1 | 1335 | 1 | >464 | 1 | 958 | 1 | >928 | 1 | >160 | 1 | 0.394 | 1 | 1.16 | 1 |
| 81 | Jun. 8, 1994 | 29 | 1 | dyspepsia.A DU | GDN | 1 | G110 | 1 | 1 | 1 | 111 | 0 | 96 | 1 | 175 | 1 | >928 | 1 | 36 | 1 | 0.262 | 1 | 0.72 | 1 |
| 84 | Nov. 22, 1993 | 24 | 1 | perforation | UD | 1 | G223 | 1 | 0 | 1 | 74 | 0 | >464 | 1 | 842 | 1 | >928 | 1 | 68 | 1 | 0.316 | 1 | 0.86 | 1 |
| 88 | Jun. 17, 1993 | 36 | 1 | dyspepsia | UD | 1 | G121 | 1 | 0 | 1 | 250 | 1 | >464 | 1 | 440 | 1 | >928 | 1 | 43 | 1 | 0.288 | 1 | 0.89 | 1 |
| 89 | Jun. 22, 1994 | 23 | 1 | dyspepsia | UD | 1 | G222 | 1 | 1 | 1 | 18 | 0 | 175 | 1 | 712 | 1 | >928 | 1 | 117 | 1 | 0.344 | 1 | 0.51 | 1 |
| 90 | May 25, 1994 | 41 | 0 | dyspepsia | UD | 1 | G321 | 1 | 1 | 1 | 80 | 0 | 384 | 1 | 612 | 1 | >928 | 1 | 97 | 1 | 0.349 | 1 | 0.78 | 1 |
| 92 | Jun. 2, 1993 | 67 | 1 | Ph | UG | 1 | G123 | 1 | 1 | 1 | 21 | 0 | 230 | 1 | 177 | 1 | 125 | 1 | 61 | 1 | 0.168 | 0 | 0.17 | 0 |
| 99 | Feb. 18, 1992 | 36 | 0 | dyspepsia-K dyspepsia | UD | 1 | G321 | 1 | 0 | 1 | 21 | 0 | 294 | 1 | 370 | 1 | >928 | 1 | 29 | 1 | 0.362 | 1 | 1.56 | 1 |
| 100 | May 13, 1992 | 38 | 1 | dyspepsia | UD | 1 | G321 | 1 | 1 | 1 | 20 | 0 | 415 | 1 | 444 | 1 | 359 | 1 | 67 | 1 | 0.369 | 1 | 0.31 | 1 |

TABLE 5

Sera of population II
27 Hp+/U+ patients

| | | | | | | | | | | | | | Aflagellate variant N6FlBA | | | | | | | | | | |
|---|---|---|---|---|---|---|---|---|---|---|---|---|---|---|---|---|---|---|---|---|---|---|---|
| No. | Date | Age | Sex | Clinical | Endos. | UD/UG | Histo-A | Giemsa | HP Cult | Ure | HP | HspA | VS = 150 | PBS | VS = 80 | NOG | VS = 60 | N6 NOG | VS = 100 | C. COR | VS = 8 | P. STAT | VS = 0.19/0.27 | JLF | VS = 0.30 |
| 1 | Apr. 14, 1993 | 24 | 0 | urt. | GDN | 0 | G221 | 1 | 1 | 1 | 1 | 218 | 1 | >464 | 1 | 884 | 1 | >928 | 1 | 42 | 1 | 0.293 | 1 | 0.43 | 1 |
| 2 | Jun. 29, 1994 | 45 | 1 | dyspepsia An. | GDN | 0 | G311 | 1 | 1 | 0 | 1 | 32 | 0 | >464 | 1 | 1896 | 1 | >928 | 1 | >160 | 1 | 0.377 | 1 | 0.50 | 1 |
| 3 | Apr. 8, 1992 | 44 | 1 | dyspepsia | GDN | 0 | G313 | 1 | 1 | 1 | 1 | 63 | 0 | 384 | 1 | 460 | 1 | 480 | 1 | 22 | 1 | 0.196 | 1 | 0.05 | 0 |
| 4 | Dec. 1, 1994 | 28 | 0 | dyspepsia | GDN | 0 | G321F | 1 | 1 | 0 | 1 | 28 | 0 | >464 | 1 | 1788 | 1 | >928 | 1 | 40 | 1 | 0.291 | 1 | 0.59 | 1 |
| 6 | Jun. 22, 1994 | 28 | 0 | dyspepsia | GDN | 0 | G220 | 0 | 1 | 1 | 1 | 14 | 0 | 204 | 1 | 354 | 1 | 324 | 1 | 16 | 1 | 0.233 | 1 | 0.18 | 0 |
| 7 | Apr. 21, 1993 | 58 | 0 | urt. | GDN | 0 | G320 | 1 | 1 | 0 | 1 | 770 | 1 | >464 | 1 | 2088 | 1 | >928 | 1 | 77 | 1 | 0.323 | 1 | 0.42 | 1 |
| 12 | Nov. 4, 1992 | 48 | 0 | dyspepsia-GDR | GDN | 0 | G210 | 1 | 1 | 1 | 1 | 341 | 1 | 251 | 1 | 906 | 1 | >928 | 1 | 101 | 1 | 0.343 | 1 | 0.71 | 1 |
| 23 | Dec. 7, 1994 | 28 | 0 | dyspepsia | GDN | 0 | G312 | 1 | 1 | 0 | 1 | 1550 | 1 | 460 | 1 | 452 | 1 | >928 | 1 | 47 | 1 | 0.33 | 1 | 0.85 | 1 |
| 24 | Apr. 21, 1993 | 39 | 1 | urt. GDR | GDN | 0 | G321 | 1 | 0 | 1 | 1 | 30 | 0 | 94 | 1 | 149 | 1 | >928 | 1 | 37 | 1 | 0.237 | 1 | 0.15 | 0 |
| 25 | Nov. 9, 1994 | 78 | 0 | An. | GDN | 0 | G121 | 1 | 1 | 0 | 1 | 3250 | 1 | >464 | 1 | 1384 | 1 | >928 | 1 | >160 | 1 | 0.41 | 1 | 0.75 | 1 |
| 31 | Jul. 21, 1993 | 53 | 1 | dyspepsia | GDN | 0 | G333 | 1 | 0 | 0 | 1 | 3820 | 1 | >464 | 1 | 3480 | 1 | >928 | 1 | >160 | 1 | 0.493 | 1 | 5.89 | 1 |
| 32 | Dec. 9, 1992 | 53 | 0 | dyspepsia alt. | GDN | 0 | G211 | 1 | 0 | 0 | 1 | 51 | 0 | 455 | 1 | 956 | 1 | >928 | 1 | 45 | 1 | 0.336 | 1 | 0.38 | 1 |
| 37 | Dec. 7, 1992 | 59 | 1 | dyspepsia | erosions G | 0 | G211 | 1 | 1 | 0 | 1 | 71 | 0 | 345 | 1 | 455 | 1 | >928 | 1 | 72 | 1 | 0.3 | 1 | 0.92 | 1 |
| 42 | Dec. 26, 1994 | 29 | 1 | dyspepsia | GDN | 0 | G321F | 0 | 1 | 0 | 1 | 423 | 1 | >464 | 1 | 1692 | 1 | >928 | 1 | 124 | 1 | 0.404 | 1 | 0.87 | 1 |
| 45 | Jun. 8, 1994 | 46 | 0 | urt. | GDN | 0 | G310 | 1 | 1 | 1 | 1 | 247 | 0 | 232 | 1 | 431 | 1 | >928 | 1 | 104 | 1 | 0.325 | 1 | 1.07 | 1 |
| 49 | May 12, 1993 | 43 | 1 | urt. | GDN | 0 | G220 | 1 | 0 | 1 | 1 | 37 | 0 | 47 | 0 | 61 | 1 | 251 | 1 | 28 | 1 | 0.179 | 0 | 0.26 | 0 |
| 55 | May 24, 1993 | 48 | 0 | dyspepsia anaemic(?) | GDN | 0 | G333 | 1 | 0 | 1 | 1 | 2375 | 1 | >464 | 1 | 786 | 1 | >928 | 1 | 100 | 1 | 0.374 | 1 | 0.42 | 1 |
| 58 | Dec. 19, 1994 | 56 | 1 | dyspepsia An | GDN | 0 | G310 | 1 | 0 | 0 | 1 | 1615 | 1 | >464 | 1 | 762 | 1 | >928 | 1 | 91 | 1 | 0.323 | 1 | 0.63 | 1 |
| 59 | May 6, 1993 | 20 | 0 | dyspepsia GDR | GDN | 0 | G111 | 1 | 0 | 0 | 1 | 0 | 0 | 63 | 0 | 134 | 1 | 254 | 1 | 8 | 0 | 0.183 | 0 | 0.44 | 1 |
| 63 | Jan. 6, 1992 | 51 | 1 | dyspepsia | GDN | 0 | G322 | 0 | 1 | 1 | 1 | 22 | 0 | >464 | 1 | 1208 | 1 | >928 | 1 | 68 | 1 | 0.332 | 1 | 0.48 | 1 |
| 67 | Jun. 1, 1994 | 37 | 1 | vomiting | GDN | 0 | G222 | 0 | 1 | 0 | 1 | 72 | 0 | 134 | 1 | 184 | 1 | 168 | 1 | 17 | 1 | 0.203 | 1 | 0.23 | 0 |
| 69 | Sep. 23, 1992 | 29 | 0 | urt. | GDN | 0 | G222 | 1 | 1 | 1 | 1 | 175 | 1 | >464 | 1 | 461 | 1 | 696 | 1 | 35 | 1 | 0.278 | 1 | 0.35 | 1 |
| 73 | Jun. 27, 1994 | 63 | 1 | dyspepsia | GDN | 0 | G212 | 1 | 1 | 1 | 1 | 812 | 1 | 158 | 1 | 309 | 1 | >928 | 1 | 149 | 1 | 0.317 | 1 | 1.28 | 1 |
| 74 | Apr. 20, 1994 | 62 | 0 | dyspepsia | GDN | 0 | G222 | 1 | 1 | 1 | 1 | 4850 | 1 | 319 | 1 | 2156 | 1 | >928 | 1 | >160 | 1 | 0.372 | 1 | 1.01 | 1 |
| 77 | Nov. 4, 1992 | 71 | 1 | anaemic (?) dyspepsia | GDN | 0 | G211 | 1 | 1 | 1 | 1 | 13 | 0 | 142 | 1 | 240 | 1 | 400 | 1 | 20 | 1 | 0.236 | 1 | 0.29 | 0 |
| 85 | Nov. 21, 1994 | 51 | 1 | GDR | GDN | 0 | G121F | 1 | 1 | 1 | 1 | 2 | 0 | 167 | 1 | 326 | 1 | 126 | 1 | 28 | 1 | 0.247 | 1 | 0.18 | 0 |
| 93 | Dec. 7, 1994 | 42 | 0 | GDR | GDN | 0 | G321 | 1 | 1 | 1 | 1 | 59 | 0 | 175 | 1 | 357 | 1 | >928 | 1 | 123 | 1 | 0.281 | 1 | 1.54 | 1 |

TABLE 5a

Sera of population II
31 Hp− patients

| | | | | | | | UD/ | Histo- | | HP | | HP | VS = | | VS = | | VS = | N6 VS = | | C. VS = | P. | VS = | | VS = |
|---|---|---|---|---|---|---|---|---|---|---|---|---|---|---|---|---|---|---|---|---|---|---|---|---|
| No. | Date | Age | Sex | Clinical | Endos. | UG | A | Giemsa | Cult | Ure | HspA | 150 | PBS | 80 | NOG | 60 | NOG | 100 | COR | 8 | STAT | 0.19/0.27 | JLF | 0.30 |

Aflagellate variant N6FIBA

| No. | Date | Age | Sex | Clinical | Endos. | UD/UG | Histo-A | Giemsa | HP Cult | Ure | HP HspA | VS=150 | PBS | VS=80 | NOG | VS=60 | NOG | N6 VS=100 | NOG | C. COR | VS=8 | P. STAT | VS=0.19/0.27 | JLF | VS=0.30 |
|---|---|---|---|---|---|---|---|---|---|---|---|---|---|---|---|---|---|---|---|---|---|---|---|---|---|
| 8 | Jul. 29, 1992 | 44 | 1 | GDR/urt. | GDN | 0 | normal | 0 | 0 | 0 | 23 | 0 | 34 | 0 | 12 | 0 | 0 | 0 | 41 | 9 | 1 | 0.158 | 0 | 0.01 | 0 |
| 14 | Jun. 2, 1993 | 34 | 1 | dyspepsia urt. | GDN | 0 | normal | 0 | 0 | 0 | 8 | 0 | 0 | 0 | 0 | 0 | 0 | 0 | 0 | 2 | 0 | 0.1 | 0 | 0.03 | 0 |
| 19 | Jun. 17, 1993 | 43 | 1 | dyspepsia | GDN | 0 | normal | 0 | 0 | 0 | 16 | 0 | 15 | 0 | 5 | 0 | 0 | 0 | 31 | 8 | 0 | 0.173 | 0 | 0.13 | 0 |
| 20 | Nov. 23, 1994 | 72 | 1 | corticoids | GDN | 0 | normal | 0 | 0 | 0 | 7 | 0 | 0 | 0 | 0 | 0 | 0 | 0 | 0 | 3 | 0 | 0.168 | 0 | 0.01 | 0 |
| 21 | Mar. 15, 1993 | 65 | 0 | dyspepsia | GDN | 0 | normal | 0 | 0 | 0 | 4 | 0 | 0 | 0 | 0 | 0 | 0 | 0 | 0 | 0 | 0 | 0.107 | 0 | 0.06 | 0 |
| 22 | Nov. 16, 1994 | 39 | 1 | urt. | GDN | 0 | normal | 0 | 0 | 0 | 2 | 0 | 64 | 0 | 40 | 0 | 0 | 0 | 88 | 0 | 0 | 0.152 | 0 | 0.04 | 0 |
| 30 | Jan. 25, 1995 | 39 | 0 | dyspepsia | GDN | 0 | normal | 0 | 0 | 0 | 10 | 0 | 28 | 0 | 12 | 0 | 0 | 0 | 34 | 4 | 0 | 0.095 | 0 | 0.02 | 0 |
| 34 | Jan. 13, 1994 | 74 | 1 | dyspepsia | GDN | 0 | normal | 0 | 0 | 0 | 29 | 0 | 38 | 0 | 15 | 0 | 0 | 0 | 56 | 6 | 0 | 0.176 | 0 | 0.00 | 0 |
| 35 | Nov. 14, 1994 | 88 | 0 | GDR | GDN | 0 | normal | 0 | 0 | 0 | 28 | 0 | 35 | 0 | 14 | 0 | 0 | 0 | 62 | 3 | 0 | 0.135 | 0 | 0.00 | 0 |
| 36 | Jan. 31, 1994 | 43 | 1 | dyspepsia | GDN | 0 | normal | 0 | 0 | 0 | 9 | 0 | 4 | 0 | 2 | 0 | 0 | 0 | 22 | 4 | 0 | 0.113 | 0 | 0.08 | 0 |
| 41 | Apr. 21, 1993 | 37 | 1 | urt. | GDN | 0 | normal | 0 | 0 | 0 | 15 | 0 | 122 | 0 | 106 | 0 | 0 | 0 | 219 | 9 | 0 | 0.17 | 0 | 0.03 | 0 |
| 46 | Oct. 7, 1992 | 39 | 1 | dyspepsia | GDN | 0 | normal | 0 | 0 | 0 | 0 | 0 | 0 | 0 | 0 | 0 | 0 | 0 | 0 | 4 | 0 | 0.133 | 0 | 0.00 | 0 |
| 47 | Jan. 27, 1993 | 40 | 0 | urt. | GDN | 0 | normal | 0 | 0 | 0 | 7 | 0 | 114 | 0 | 99 | 0 | 0 | 0 | 199 | 6 | 0 | 0.153 | 0 | 0.03 | 0 |
| 50 | Jul. 9, 1992 | 19 | 1 | dyspepsia | GDN | 0 | normal | 0 | 0 | 0 | 4 | 0 | 11 | 0 | 5 | 0 | 0 | 0 | 13 | 0 | 0 | 0.13 | 0 | 0.01 | 0 |
| 51 | Feb. 10, 1993 | 28 | 1 | urt. | GDN | 0 | normal | 0 | 0 | 0 | 14 | 0 | 7 | 0 | 2 | 0 | 0 | 0 | 7 | 4 | 0 | 0.119 | 0 | 0.00 | 0 |
| 54 | Feb. 24, 1993 | 51 | 1 | dyspepsia | GDN | 0 | normal | 0 | 0 | 0 | 8 | 0 | 24 | 0 | 11 | 0 | 0 | 0 | 29 | 3 | 0 | 0.143 | 0 | 0.00 | 0 |
| 57 | Aug. 6, 1991 | 60 | 1 | GDR | GDN | 0 | normal | 0 | 0 | 0 | 32 | 0 | 61 | 0 | 66 | 0 | 0 | 0 | 436 | 8 | 0 | 0.227 | 1 | 0.38 | 1 |
| 61 | Jan. 11, 1995 | 42 | 0 | GDR | GDN | 0 | normal | 0 | 0 | 0 | 9 | 0 | 10 | 0 | 2 | 0 | 0 | 0 | 11 | 0 | 0 | 0.062 | 0 | 0.00 | 0 |
| 62 | Jul. 21, 1993 | 37 | 0 | dyspepsia | GDN | 0 | normal | 0 | 0 | 0 | 4 | 0 | 6 | 0 | 3 | 0 | 0 | 0 | 8 | 1 | 0 | 0.115 | 0 | 0.01 | 0 |
| 68 | Jan. 7, 1992 | 61 | 1 | dyspepsia | GDN | 0 | normal | 0 | 0 | 0 | 6 | 0 | 70 | 0 | 33 | 0 | 0 | 0 | 89 | 8 | 0 | 0.17 | 0 | 0.07 | 0 |
| 72 | Oct. 21, 1992 | 41 | 1 | GDR | GDN | 0 | normal | 0 | 0 | 0 | 13 | 0 | 1 | 0 | 3 | 0 | 0 | 0 | 3 | 5 | 0 | 0.189 | 0 | 0.09 | 0 |
| 79 | Apr. 7, 1993 | 48 | 0 | dyspepsia | GDN | 0 | normal | 0 | 0 | 0 | 3 | 0 | 12 | 0 | 21 | 0 | 0 | 0 | 32 | 4 | 0 | 0.124 | 0 | 0.03 | 0 |
| 80 | Feb. 3, 1993 | 41 | 0 | urt. | GDN | 0 | normal | 0 | 0 | 0 | 3 | 0 | 11 | 0 | 8 | 0 | 0 | 0 | 27 | 7 | 0 | 0.2 | 1 | 0.06 | 0 |
| 82 | Nov. 24, 1993 | 42 | 1 | dyspepsia | GDN | 0 | normal | 0 | 0 | 0 | 3 | 0 | 25 | 0 | 13 | 0 | 0 | 0 | 25 | 4 | 0 | 0.139 | 0 | 0.00 | 0 |
| 86 | Jan. 11, 1995 | 35 | 0 | GDR | GDN | 0 | normal | 0 | 0 | 0 | 2 | 0 | 0 | 0 | 0 | 0 | 0 | 0 | 0 | 7 | 0 | 0.126 | 0 | 0.00 | 0 |
| 87 | Mar. 30, 1994 | 23 | 0 | GDR | GDN | 0 | normal | 0 | 0 | 0 | 22 | 0 | 3 | 0 | 4 | 0 | 0 | 0 | 11 | 3 | 0 | 0.125 | 0 | 0.01 | 0 |
| 91 | Jul. 13, 1994 | 17 | 0 | dyspepsia | GDN | 0 | normal | 0 | 0 | 0 | 12 | 0 | 40 | 0 | 18 | 0 | 0 | 0 | 41 | 2 | 0 | 0.166 | 0 | 0.01 | 0 |
| 94 | Feb. 13, 1992 | 35 | 0 | dyspepsia | GDN | 0 | normal | 0 | 0 | 0 | 21 | 0 | 22 | 0 | 15 | 0 | 0 | 0 | 38 | 1 | 0 | 0.274 | 1 | 0.07 | 0 |
| 95 | Mar. 21, 1990 | 33 | 1 | dyspepsia | GDN | 0 | normal | 0 | 0 | 0 | 19 | 0 | 43 | 0 | 22 | 0 | 0 | 0 | 54 | 1 | 0 | 0.268 | 0 | 0.00 | 0 |
| 97 | Jan. 5, 1995 | 42 | 1 | GDR | GDN | 0 | normal | 0 | 0 | 0 | 3 | 0 | 3 | 0 | 4 | 0 | 0 | 0 | 11 | 0 | 0 | 0.246 | 0 | 0.02 | 0 |
| 98 | May 22, 1992 | 54 | 1 | dyspepsia | GDN | 0 | normal | 0 | 0 | 0 | 2 | 0 | 1 | 0 | 0 | 0 | 0 | 0 | 3 | 0 | 0 | 0.122 | 0 | 0.00 | 0 |

TABLE 6

Sera of population II
In relation to the presence of Hp (culture and/or anamatopathologically) and ulcer

| | | | | Sensibility | Specificity |
|---|---|---|---|---|---|
| In relation to Hp+ and DU/GU that is: 34Hp+/U+ | N6flbA | HspA malE | VS = 100 | 44.1% (15/34) | 100% (31/31) |
| | | | VS = 50 | 52.9% (18/34) | 100% (31/31) |
| | | | VS = 20 | 64.7% (22/34) | 73.8% (25/31) |
| | | NOG | VS = 100 | 94.1% (32/34) | 96.8% (30/31) |
| | | | VS = 80 | 94.1% (32/34) | 93.6% (29/31) |
| | | | VS = 60 | 100% (34/34) | 90.3% (28/31) |
| | | PBS | VS = 100 | 82.4% (28/34) | 93.6% (29/31) |
| | | | VS = 80 | 94.1% (32/34) | 93.6% (29/31) |
| | | | VS = 60 | 97.1% (33/34) | 83.9% (26/31) |
| | | JLF Sero | VS = 0.30 | 82.4% (28/34) | 96.8% (30/31) |
| | | Pylori Stat | | 94.1% (32/34) | 90.3% (28/31) |
| | | Cobas Core | | 100% (34/34) | 93.6% (29/31) |

TABLE 7

Sera of population II
In relation to the presence of Hp (culture and/or anamatopathologically)

| | | | | Specificity | Sensibility |
|---|---|---|---|---|---|
| In relation to Hp+: -34 DU/GU -27 GNU that is: 61 Hp+ 31 Hp- | N6flbA- | HspA malE | VS = 100 | 45.9% (28/61) | 100% (31/31) |
| | | | VS = 50 | 59% (36/61) | 100% (31/31) |
| | | | VS = 20 | 80.7% (45/61) | 73.8% (25/31) |
| | | NOG | VS = 100 | 95.1% (58/61) | 96.8% (30/31) |
| | | | VS = 80 | 95.1% (58/61) | 93.6% (29/31) |
| | | | VS = 60 | 100% (61/61) | 90.3% (28/31) |
| | | PBS | VS = 100 | 85.3% (52/61) | 93.6% (29/31) |
| | | | VS = 80 | 93.4% (57/61) | 93.6% (29/31) |
| | | | VS = 60 | 96.7% (59/61) | 83.9% (26/31) |
| | | JLF sero | VS = 0.30 | 78.7% (48/61) | 96.8% (30/31) |
| | | Pylori Stat | | 93.4% (57/61) | 90.3% (28/31) |
| | | Cobas Core | | 93.3% (60/61)* | 93.6% (29/31) |

*Serum = VS

TABLE 8

Sera of population II
In relation to the presence of Hp (culture and/or anamatopathologically) and the absence of an ulcer

| | | | | Specificity | Sensibility |
|---|---|---|---|---|---|
| In relation to Hp+ and GNU that is: 27 Hp+/U- | Nbf1bA- | HspA malE | VS = 100 | 48.2% (13/27) | 100% (31/31) |
| | | | VS = 50 | 66.7% (18/27) | 100% (31/31) |
| | | | VS = 20 | 85.2% (23/27) | 73.8% (25/31) |
| | | NOG | VS = 100 | 96.3% (26/27) | 96.8% (30/31) |
| | | | VS = 80 | 93.6% (26/27) | 93.6% (29/31) |
| | | | VS = 60 | 100% (27/27) | 90.3% (28/31) |
| | | PBS | VS = 100 | 88.9% (24/27) | 93.6% (29/31) |
| | | | VS = 80 | 92.6% (25/27) | 93.6% (29/31) |
| | | | VS = 60 | 96.3% (26/27) | 83.9% (26/31) |
| | | JLF sero | VS = 0.30 | 74.1% (20/27) | 96.8% (30/31) |
| | | Pylori stat | | 92.6% (25/27) | 90.3% (28/31) |
| | | Cobas Core | | 96.3% (26/27) | 93.6% (29/31) |

The place of serology

Serology is placed at 2 levels:

Very sensitive serology: for the purpose of detecting the presence of the bacterium in young subjects complaining of epigastric pains. If the serology turns out to be negative, the subject will not have to suffer endoscopy or a biopsy and another cause for his pains will be sought.

Risk-specific serology: this involves demonstrating the risk of having a serious infection with *Helicobacter pylori*, that is an ulcer, a cancer or a gastric lymphoma (MALT lymphoma).

either using a molecule which is specific for the risk in question or using a risk-specific threshold (threshold value which is higher in subjects which are at risk than in subjects which are not at risk).

This specific serology can be employed to screen the general population and thus to detect cancers and lymphomas which are associated with *Helicobacter pylori* and which would not be detected because of a lack of symptoms. (Only subjects which complain of pain will consult a gastroenterologist).

The response to the sensitivity issue is good.

TABLE 9

Mean and standard deviation of the A.U.'s in the 3 groups of patients

| | | Hp- (n = 31) | Hp+/U- (n = 27) | Hp+/U+ (n = 34) |
|---|---|---|---|---|
| Hsp A | mean | 10.61 | 775.72 | 770.32 |
| | standard deviation | 8.81 | 1312.56 | 1666.52 |
| N6flBA-(NOG) | mean | 17.16 | 895.50 | 944.85 |
| | standard deviation | 26.69 | 818.57 | 915.27 |

TABLE 10

Mean and standard deviation of the A.U.'s in terms of gastric histology

| Intensity | | Atrophy | | | Inflammation | | | | Activity | | |
|---|---|---|---|---|---|---|---|---|---|---|---|
| | | Hsp A | NOG | P. Stat | Cag A | Hsp A | NOG | P. Stat | Hsp A | NOG | P. Stat |
| 0 | Mean | | | | | | | | 977 | 712 | 0.31 |
| | (standard deviation) | | | | | | | | 2052 | 680 | 0.08 |
| 1 | Mean | 410 | 412 | 0.26 | 93 | 437 | 577 | 0.30 | 479 | 938 | 0.32 |
| | (standard deviation) | 1004 | 390 | 0.07 | 122 | 669 | 466 | 0.06 | 1117 | 876 | 0.09 |
| 2 | Mean | 423 | 730 | 0.30 | 188 | 639 | 878 | 0.31 | 733 | 796 | 0.31 |
| | (standard deviation) | 964 | 707 | 0.08 | 200 | 1655 | 780 | 0.09 | 1382 | 753 | 0.07 |
| 3 | Mean | 1321 | 1403 | 0.36 | 554 | 2409 | 2176 | 0.43 | 1302 | 1402 | 0.35 |
| | (standard deviation) | 2059 | 1012 | 0.08 | 607 | 1742 | 1132 | 0.08 | 1629 | 1174 | 0.12 |

61 Hp+:

| Distribution | Atrophy | Inflammation | Activity |
|---|---|---|---|
| 0 | 0 | 0 | 15 |
| 1 | 10 | 21 | 25 |
| 2 | 28 | 33 | 12 |
| 3 | 22 | 7 | 9 |
| 4 | 1 | 0 | 0 |

Correlation between the Intensity of the Gastritis and the Antibody Levels

The gastritis is defined by 3 parameters:

Atrophy (represented by the first figure after G); its intensity is marked from 1 to 4.

The global inflammation corresponds to infiltration with neutrophilic polynuclear cells and with monocytes; (represented by the second figure after the G). Its intensity is marked from 1 to 3.

Activity corresponds to the number of neutrophilic polynuclear cells (represented by the third figure after the G); its intensity is marked from 0 to 3. Some folicular forms are marked F.

Normally, the following correlation can be observed:

The activity correlates very well with *Helicobacter pylori*.

The inflammation correlates well with *Helicobacter pylori*.

The means of the titren observed in each group have therefore been calculated in terms of these 3 parameters and their intensity.

Interpretation of the Results

Use of a t test makes it possible to demonstrate whether a difference between 2 observed means is significant or not with a 5% risk.

The hypothesis on which the t test is based is the equality of variances, demonstrated by an F test (Fisher test).

Since some variances are not equal, it is not therefore possible to compare all the means with each other.

By comparing the means, when possible, it has been possible to demonstrate whether the differences between the different groups are significant or not.

Significant difference

Between the means of "2" and "3" for HspA and NOG in the "Inflammation" group.

Non-significant Difference

With regard to activity, no significant differences were demonstrated between the different intensity levels:

| | |
|---|---|
| HspA: | |
| no significant difference between levels | 0 and 2 |
| | 0 and 3 |
| | 1 and 2 |
| | 1 and 3 |
| | 2 and 3 |
| NOG: | |
| no significant difference between levels | 0 and 1 |
| | 0 and 2 |
| | 1 and 2 |
| | 1 and 3 |
| | 2 and 3. |

It is nevertheless possible to observe a tendency for the titres to increase in dependence on the intensity of the gastritis:

with regard to atrophy, the means double, for HspA and for the NOG extract of the aflagellate strain, when passing from level 1 to 2 and from level 2 to 3.

with regard to inflammation, the means double when passing from level 1 to 2.

The numbers in each group are relativity low (in each case <30) for drawing conclusions with regard to statistically significant differences.

TABLE 11

Means of the A.U.'s in terms of gastric histology

For HP+/U+

| Intensity | | Atrophy | | | Inflammation | | | Activity | | |
|---|---|---|---|---|---|---|---|---|---|---|
| | | Hsp A | NOG | P. Stat | Hsp A | NOG | P. Stat | Hsp A | NOG | P. Stat |
| 0 | Mean | | | | | | | 1292 | 675 | 0.32 |
| | (standard deviation) | | | | | | | 2619 | 697 | 0.09 |
| 1 | Mean | 121 | 326 | 0.25 | 438 | 511 | 0.30 | 599 | 1015 | 0.34 |
| | (standard deviation) | 118 | 218 | 0.05 | 759 | 451 | 0.06 | 1298 | 1050 | 0.10 |
| 2 | Mean | 304 | 793 | 0.32 | 586 | 845 | 0.33 | 219 | 827 | 0.32 |
| | (standard deviation) | 507 | 784 | 0.09 | 1820 | 813 | 0.09 | 329 | 835 | 0.09 |
| 3 | Mean | 2004 | 1722 | 0.41 | 2133 | 2194 | 0.43 | 911 | 1316 | 0.35 |
| | (standard deviation) | 2856 | 1060 | 0.07 | 1989 | 1006 | 0.09 | 1502 | 1040 | 0.12 |

34 Hp+/U+:

| Distribution | Atrophy | Inflammation | Activity |
|---|---|---|---|
| 0 | 0 | 0 | 9 |
| 1 | 7 | 10 | 13 |
| 2 | 17 | 19 | 6 |
| 3 | 9 | 5 | 6 |
| 4 | 1 | 0 | 0 |

Sera able to Exhibit Cross Reactions 2 types of sera were employed.

- 20 sera (10 anti-Legionella+ and 10 anti-Chlamydia +) being able to exhibit cross reactions with HspA, because these 3 bacterial possess heat shock proteins which are very akin to each other.
- 3 anti-Campylobacter positive sera, in order to demonstrate cross reactions with the flagellate strain N6 which would disappear with the aflagellate strain N6flbA-. It is very difficult to obtain anti-Campylobacter positive sera; this is the reason for there only being 3 sera.

HspA does not exhibit any cross reaction, either with the 10 anti-Legionella positive sera or with the 10 anti-Chlamydia positive sera.

While some of these sera have positive titres of anti-*Helicobacter pylori* antibodies, both with the flagellate strain and with the aflagellate strain, the clinical contest of these sera is not known.

TABLE 12

Sera which are able to exhibit cross reactions

| | Titer | N6 | VS = 100 | N6flBA- | VS = 60 | HspA | VS = 100 |
|---|---|---|---|---|---|---|---|
| Legionella + | | | | | | | |
| A | P2 P3 = 256 | 0 | 0 | 4 | 0 | 47 | 0 |
| B | P4 P5 = 64 | >928 | 1 | 641 | 1 | 42 | 0 |
| C | P2 P3 = 128 | 212 | 1 | 87 | 1 | 68 | 0 |
| D | P2 P3 = 64 | 70 | 0 | 19 | 0 | 15 | 0 |
| E | P1 = 256/P2 = 512 | >928 | 1 | 239 | 1 | 258 | 1 |
| F | P2 P3 P4 P5 = 128 | 322 | 1 | 121 | 1 | 41 | 0 |
| G | P1 = 512/P6 = 1024 | >928 | 1 | 193 | 1 | 121 | 1 |
| H | P4 P5 = 64 | >928 | 1 | 479 | 1 | 18 | 0 |
| I | P2 = 128/P3 = 64 | 33 | 0 | 17 | 0 | 25 | 0 |
| J | P2 = 256/P3 = 128 | 16 | 0 | 8 | 0 | 32 | 0 |
| Chlamydis + | | | | | | | |
| A | 256 | 5 | 0 | 8 | 0 | 25 | 0 |
| B | 256 | 7 | 0 | 9 | 0 | 34 | 0 |
| C | 64 | 636 | 1 | 290 | 1 | 39 | 0 |
| D | 256 | 367 | 1 | 225 | 1 | 19 | 0 |
| E | 32 | >928 | 1 | 855 | 1 | 19 | 0 |
| F | 128 | >928 | 1 | 783 | 1 | 27 | 0 |
| G | 32 | 115 | 1 | 55 | 0 | 15 | 0 |
| H Twar | 16 | 19 | 0 | 10 | 0 | 14 | 0 |
| I | 32 | >928 | 1 | 592 | 1 | >928 | 1 |
| J Twar | 64 | 610 | 1 | 280 | 1 | 44 | 0 |

TABLE 12-continued

Sera which are able to exhibit cross reactions

| Titer | N6 | VS = 100 | N6flBA- | VS = 60 | HspA | VS = 100 |
|---|---|---|---|---|---|---|
| Campylobacter + | | | | | | |
| A | 35 | 0 | 28 | 0 | 17 | 0 |
| B | 13 | 0 | 4 | 0 | 27 | 0 |
| C | 50 | 0 | 68 | 1 | 89 | 0 |

CONCLUSION

HspA malE

It is still not possible to use this molecule on its own since it also lacks sensitivity, but it could be of interest if it is associated with other molecules.

It nevertheless carries a risk of cross reactions due to the substantial conservation of these heat shock proteins between the different bacterial species.

N6flbA-

This aflagellate variant appears to be of great interest; the sensitivity and specificity which were obtained with serum population II demonstrate a very favourable efficacy.

N6

For the time being, the flagellate strain appears to be of interest. However, the cross reactions relating to the flagellum have only been studied to a limited extent due to the difficulty of obtaining sera which are well documented with regard to *Campylobacter serology*.

JLF test

A serological test based on an aqueous (PBS) extract of several strains of *Helicobacter pylori* was developed. This test appears to be very efficacious.

A NOG extract of the aflagellate variant was used to test serum population I.

87 sera, which were documented only from the bacteriological and anatomopathological points of view, were tested with the aflagellate bacterial extract.

A serum is positive if the culture is positive or if the anatomopathology and the rapid urea test are positive.

A serum is negative if the 3 tests (culture, anatomopathology and rapid urea test) are negative.

A sensitivity of 90.3% (28/31) is found together with a specificity of 71.4% (40/56).

Of 16 sera which are falsely positive using a first test, 9 are positive either using JLF serology or using the JLF Western blot, or using both of them.

Of the 3 sera which are falsely negative using a first test, all 3 are negative either with JLF serology or with JLF Western blot, and one serum is negative with both the systems.

TABLE 13

87 sera from population I tested with the n-octyl glucoside extract of the aflagellate strain

| | | JLF | | | | WB | | | N6flBA- | |
|---|---|---|---|---|---|---|---|---|---|---|
| No. of serum | HspA | VS 150 | sero | VS 35 | WB JLF | interp | Bioptim | Hp | NOG | VS = 60 |
| 572 | 35 | 0 | 21 | 0 | 2p | − | + | 0 | 128 | |
| 573 | 11 | 0 | 46 | 1 | 3p | + | − | 1 | 229 | 1 |
| 574 | 11 | 0 | 3 | 0 | 1p | − | − | 0 | 9 | 0 |
| 575 | 0 | 0 | 63 | | 3p | | − | 0 | 166 | |
| 576 | 121 | 0 | 19 | 0 | 3p | | + | 0 | 246 | |
| 577 | 0 | 0 | 1 | 0 | 0 | − | − | 0 | 3 | 0 |
| 578 | 6 | 0 | 4 | 0 | 0 | − | − | 0 | 24 | 0 |
| 579 | 2630 | 1 | 114 | 1 | 3p | + | − | 1 | >464 | 1 |
| 580 | 721 | 1 | 125 | 1 | 4p | + | − | 1 | >464 | 1 |
| 581 | 0 | 0 | 2 | 0 | 0 | − | − | 0 | 2 | 0 |
| 582 | 0 | 0 | 2 | 0 | 1p | − | − | 0 | 6 | 0 |
| 583 | 0 | 0 | 3 | 0 | 2p | − | − | 0 | 27 | 0 |
| 584 | 36 | 0 | 1 | 0 | 2p | − | − | 0 | 12 | 0 |
| 585 | 2114 | 1 | 125 | 1 | 4p | + | + | 1 | >464 | 1 |
| 587 | 19 | 0 | 2 | 0 | 2p | − | − | 0 | 11 | 0 |
| 588 | 1388 | 1 | 58 | 1 | 3p | + | − | 1 | >464 | 1 |
| 589 | 323 | 1 | 3 | 0 | 4p | | + | 0 | >464 | |
| 591 | 4 | 0 | 4 | 0 | 2p | − | − | 0 | 9 | 0 |
| 592 | 6 | 0 | 0 | 0 | 2p | − | − | 0 | 9 | 0 |
| 593 | 44 | 0 | 28 | 0 | 3p | | − | 1 | 3 | |
| 595 | 76 | 0 | 78 | 1 | 4p | + | + | 1 | >464 | 1 |
| 597 | 0 | 0 | 0 | 0 | 0 | − | − | 0 | 9 | 0 |
| 599 | 49 | 0 | 125 | 1 | 4p | + | + | 1 | >464 | 1 |
| 600 | 0 | 0 | 3 | 0 | 0 | − | − | 0 | 3 | 0 |
| 601 | 6 | 0 | 1 | 0 | 0 | − | − | 0 | 6 | 0 |
| 602 | 0 | 0 | 0 | 0 | 0 | − | − | 0 | 0 | 0 |
| 605 | 11 | 0 | 0 | 0 | 0 | − | − | 0 | 10 | 0 |
| 608 | 5 | 0 | 5 | 0 | 0 | − | − | 0 | 9 | 0 |
| 609 | 308 | 1 | 8 | 0 | 0 | − | − | 0 | 13 | 0 |
| 610 | 2370 | 1 | 111 | 1 | 4p | + | − | 1 | >464 | 1 |
| 612 | 477 | 1 | 34 | 0 | 4p | | + | 0 | 422 | |
| 613 | 46 | 0 | 0 | 0 | 0 | − | − | 0 | 3 | 0 |

TABLE 13-continued 87 sera from population I tested with the n-octyl glucoside extract of the aflagellate strain

| No. of serum | HspA | JLF VS 150 | sero | VS 35 | WB JLF | WB interp | Bioptim | Hp | N6flBA-NOG | VS = 60 |
|---|---|---|---|---|---|---|---|---|---|---|
| 616 | 741 | 1 | 73 | 1 | 4p | + | + | 1 | >464 | 1 |
| 617 | 1725 | 1 | 125 | 1 | 4p | + | − | 1 | 286 | 1 |
| 618 | 426 | 1 | 101 | 1 | 4p | + | + | 1 | >464 | 1 |
| 621 | 0 | 0 | 82 | 1 | 4p | + | + | 1 | >464 | 1 |
| 622 | 15 | 0 | 6 | 0 | 2p | − | − | 0 | 25 | 0 |
| 624 | 411 | 1 | 110 | | 4p | | + | 0 | >464 | |
| 626 | 46 | 0 | 11 | | 1p | | − | 1 | 53 | |
| 627 | 0 | 0 | 48 | | 1p | | − | 1 | 27 | |
| 629 | 6 | 0 | 2 | 0 | 0 | − | − | 0 | 2 | 0 |
| 631 | 31 | 0 | 21 | 0 | 2p | − | − | 0 | 92 | |
| 632 | 0 | 0 | 3 | 0 | 0 | − | − | 0 | 22 | 0 |
| 633 | 285 | 1 | 104 | 1 | 3p | + | + | 1 | >464 | 1 |
| 634 | 48 | 0 | 69 | 1 | 4p | + | − | 1 | >464 | 1 |
| 636 | 523 | 1 | 33 | 0 | 2p | − | − | 1 | 71 | 1 |

TABLE 14

87 sera from population I tested with the n-octyl glucoside extract of the aflagellate strain

| No. of serum | HspA | JLF VS 150 | Sero | VS 35 | WB JLF | WB interp | Bioptim | Hp | N6flBA-NOG | VS = 60 |
|---|---|---|---|---|---|---|---|---|---|---|
| 638 | 922 | 1 | 36 | 1 | 3p | + | + | 1 | >464 | 1 |
| 641 | 0 | 0 | 6 | 0 | 1p | − | − | 0 | 8 | 0 |
| 645 | 29 | 0 | 8 | 0 | 1p | − | − | 0 | 29 | 0 |
| 647 | 0 | 0 | 2 | 0 | 1p | − | − | 0 | 4 | 0 |
| 649 | 5 | 0 | 5 | 0 | 0 | − | − | 0 | 12 | 0 |
| 650 | 6 | 0 | 0 | 0 | 0 | − | − | 0 | 3 | 0 |
| 654 | 0 | 0 | 1 | 0 | 0 | − | − | 0 | 4 | 0 |
| 655 | 49 | 0 | 59 | 1 | 2p | − | − | 1 | 229 | 1 |
| 656 | 0 | 0 | 3 | 0 | 0 | − | − | 0 | 8 | 0 |
| 657 | 363 | 1 | 105 | 1 | 4p | + | + | 1 | >464 | 1 |
| 658 | 0 | 0 | 8 | 0 | 1p | − | − | 0 | 8 | 0 |
| 659 | 0 | 0 | 3 | 0 | 0 | − | − | 0 | 3 | 0 |
| 662 | 73 | 0 | 3 | 0 | 2p | − | − | 0 | 40 | 0 |
| 663 | 25 | 0 | 21 | 0 | 2p | − | − | 0 | 103 | |
| 467 | 86 | 0 | 26 | 0 | 4p | | − | 0 | 96 | |
| 468 | 32 | 0 | 68 | 1 | 4p | + | + | 1 | >464 | 1 |
| 469 | 265 | 1 | 118 | 1 | 3p | + | + | 1 | >464 | 1 |
| 470 | 734 | 1 | 77 | | 2p | −/+ | + | 0 | >464 | |
| 471 | 214 | 1 | 100 | 1 | 4p | + | − | 1 | >464 | 1 |
| 472 | 4 | 0 | 5 | 0 | 0 | − | − | 0 | 0 | 0 |
| 473 | 1023 | 1 | 55 | 1 | 3p | + | − | 1 | >464 | 1 |
| 474 | 12 | 0 | 10 | 0 | 0 | − | − | 0 | 21 | 0 |
| 475 | 9 | 0 | 13 | 0 | 0 | − | + | 0 | 210 | |
| 476 | 2611 | 1 | 74 | 1 | 4p | + | + | 1 | >464 | 1 |
| 478 | 0 | 0 | 0 | 0 | 0 | − | − | 0 | 1 | 0 |
| 479 | 175 | 1 | 9 | 0 | 4p | | − | 0 | 348 | |
| 480 | 0 | 0 | 1 | 0 | 0 | − | − | 0 | 7 | 0 |
| 481 | 800 | 1 | 92 | 1 | 3p | + | + | 1 | 425 | 1 |
| 482 | 0 | 0 | 1 | 0 | 0 | − | − | 0 | 8 | 0 |
| 483 | 0 | 0 | 39 | 1 | 3p | + | + | 1 | >464 | 1 |
| 484 | 0 | 0 | 3 | 0 | 0 | − | − | 0 | 20 | 0 |
| 485 | 0 | 0 | 1 | 0 | 0 | − | − | 0 | 11 | 0 |
| 486 | 0 | 0 | 2 | 0 | 0 | − | − | 0 | 6 | 0 |
| 725 | 0 | 0 | 7 | 0 | 0 | − | − | 0 | 198 | |
| 730 | 190 | 1 | 45 | | 1p | − | − | 0 | 372 | |
| 732 | 0 | 0 | 10 | 0 | 1p | − | − | 0 | 145 | |
| 735 | 0 | 0 | 30 | 0 | 2p | − | − | 0 | 143 | 1 |
| 736 | 0 | 0 | 0 | 0 | 0 | − | − | 0 | 0 | 0 |
| 737 | 25 | 0 | 102 | 1 | 4p | + | − | 1 | 155 | 1 |
| 738 | 2233 | 1 | 125 | 1 | 4p | + | − | 1 | >464 | 1 |
| 739 | 79 | 0 | 33 | 0 | 1p | − | + | 0 | 274 | |

Technique

| Plates coated with: | HspA antigen at 2 μg/ml |
| --- | --- |
| | NOG extract of NflbA and N6 at 3 μg/ml |
| Range: | 5 range points negative control |
| | positive control used at 4 dilutions |
| Patient sera: | 1/100 dilution |
| volume deposited: | 100 μl |
| Incubation: | 37° C. for 1 hour |
| 3 washings: | |
| Monoclonal conjugate (IgG toxo) used at | 1/32,000 for HspA |
| | 1/64,000 for N6flbA- |
| | 1/56,000 for N6 |
| volume deposited: | 100 μl |

Incubation of the conjugate: 37° C. for 1 hour 4 washings

Development of the enzyme reaction using OPD+ substrate 30 minutes in the dark

Termination of the enzyme reaction with $H_2SO_4$

Reading of the OD at 492 nm/620 nm

Conversion of the OD's into arbitrary units (AU).

TABLE 15

Documented sera from population I
42 Hp + sera

| No. of serum | Sex | Date of birth | Endos. | ANAMATOPATHOLOGY Giemsa | Histo | BACTERIOLOGY Gram | Urea | Cult. | Hp | JLF Sero | VS = 0.3 | NOG | VS = 60 |
| --- | --- | --- | --- | --- | --- | --- | --- | --- | --- | --- | --- | --- | --- |
| 952253 | 1 | Oct. 1, 1960 | G, H | 0 | G | 1 | 1 | 1 | 1 | 1 | 1 | >464 | 1 |
| 236174 | 1 | May 2, 1960 | G | 0 | G | 1 | 1 | 1 | 1 | 10.42 | 1 | 216 | 1 |
| 974107 | 2 | Feb. 15, 1932 | G(mini) | 0 | G | 1 | 1 | 1 | 1 | 1.39 | 1 | 272 | 1 |
| 34812 | 1 | Dec. 10, 1952 | G, B | 0 | G | 1 | 1 | 1 | 1 | 0.82 | 1 | 452 | 1 |
| 229712 | 2 | Aug. 11, 1953 | G | 0 | G | 1 | 1 | 1 | 1 | 0.11 | | 148 | 1 |
| 46511 | 1 | Jan. 17, 1970 | G | 0 | G | 1* | 0 | 1 | 1 | 1.26 | 1 | 213 | 1 |
| 180334 | 2 | Jan. 14, 1959 | G | 0 | U | 1 | 1 | 1 | 1 | 0.83 | 1 | >464 | 1 |
| 189005 | 2 | Oct. 23, 1925 | U | 0 | U | 1 | 1 | 1 | 1 | 0.87 | 1 | >464 | 1 |
| 49860 | 1 | Jul. 6, 1964 | U | 0 | U | 1 | 1 | 1 | 1 | 2 | 1 | >464 | 1 |
| 168332 | 1 | Nov. 6, 1960 | G | 1 | G | 1 | 1 | 1 | 1 | 0.23 | | 394 | 1 |
| 195282 | 1 | Jun. 11, 1946 | G | 1 | G | 1 | 0 | 1 | 1 | 0.91 | 1 | 180 | 1 |
| 176859 | 1 | Apr. 24, 1950 | G | 1 | G | 1 | 1 | 1 | 1 | 1.39 | 1 | >464 | 1 |
| 987898 | 1 | May 13, 1958 | G | 1 | G | 1 | 1 | 1 | 1 | 0.69 | 1 | 297 | 1 |
| 954498 | 2 | Dec. 1, 1945 | G | 1 | G | 1 | 1 | 1 | 1 | 1.12 | 1 | >464 | 1 |
| 195175 | 2 | Sep. 1, 1908 | G | 1 | G | 0 | 0 | 1 | 1 | 2.7 | 1 | >464 | 1 |
| 156007 | 2 | Sep. 27, 1956 | G, B | 1 | G | 1 | 1 | 1 | 1 | 1.68 | 1 | 437 | 1 |
| 18318 | 1 | Dec. 19, 1963 | G, B | 1 | G | 1 | 1 | 1 | | 0.36 | 1 | 45 | |
| 215979 | 2 | May 4, 1919 | H, G, B | 1 | G | 1 | 1 | 1 | 1 | 1.2 | 1 | >464 | 1 |
| 25322 | 2 | Feb. 12, 1916 | G | 1 | G | 1 | 1 | 1 | 1 | 2.5 | 1 | >464 | 1 |
| 26555 | 1 | Nov. 9, 1965 | U, H | 1 | G | 1 | 1 | 1 | 1 | 2.4 | 1 | >464 | 1 |
| 193295 | 1 | Jan. 24, 1916 | ant. bu. U | 1 | G | 1 | 1 | 1 | 1 | 2.5 | 1 | >464 | 1 |
| 237220 | 1 | Jun. 1, 1965 | bulb. U | 1 | G | 1 | 0 | 1 | 1 | 0.14 | | 328 | 1 |
| 237191 | 1 | May 6, 1942 | bulb. U | 1 | G | 1 | 0 | 1 | 1 | 1.16 | 1 | >464 | 1 |
| 238683 | 1 | Sep. 13, 1930 | G, bulb. U | 1 | G | 1 | 1 | 1 | 1 | 1.73 | 1 | >464 | 1 |
| 79163 | 1 | Jul. 6, 1972 | G | 1 | G | 1 | 1 | 1 | 1 | 0.46 | 1 | 312 | 1 |
| 87951 | 1 | Apr. 15, 1941 | G | 1 | G | 1 | 1 | 1 | 1 | 0.7 | 1 | >464 | 1 |
| 93773 | 1 | May 12, 1943 | G | 1 | G | 0 | 0 | 1 | 1 | 1.05 | 1 | >464 | 1 |
| 97478 | 1 | May 4, 1965 | G | 1 | G | 1 | 1 | 1 | 1 | 0.42 | 1 | >464 | 1 |
| 96436 | 1 | Nov. 6, 1974 | G | 1 | G | 1 | 1 | 1 | 1 | 0.84 | 1 | 183 | 1 |
| 66502 | 1 | Oct. 2, 1945 | G | 1 | G | 1 | 1 | 1 | 1 | 0.78 | 1 | >464 | 1 |
| 42230 | 2 | Jun. 12, 1958 | G | 1 | G | 1 | 1 | 1 | 1 | 0.81 | 1 | >464 | 1 |
| 51105 | 2 | Aug. 12, 1945 | G, DU | 1 | G | 1 | 1 | 1 | 1 | 1.1 | 1 | >464 | 1 |
| 58631 | 1 | Aug. 21, 1943 | G | 1 | G | 1 | 1 | 1 | 1 | 0.8 | 1 | 214 | 1 |
| 79105 | 2 | Jan. 28, 1961 | G, DU | 1 | G | 1 | 1 | 1 | 1 | 1.25 | 1 | >464 | 1 |
| 99121 | 1 | Oct. 28, 1959 | G | 1 | G | 1 | 1 | 1 | 1 | 0.9 | 1 | 449 | 1 |
| 216779 | 1 | Apr. 8, 1947 | G, U | 1 | G/U | 1 | 1 | 1 | 1 | 0.25 | | 283 | 1 |
| 996070 | 1 | Jan. 29, 1947 | G | 1 | preatroph. G | 1 | 1 | 1 | 1 | 0.31 | 1 | 121 | 1 |
| 72420 | 1 | May 15, 1955 | G, DU | 1 | G, DU | 1 | 1 | 1 | 1 | 1.2 | 1 | >464 | 1 |
| 205110 | 1 | Jun. 10, 1961 | DU | 1 | U | 1 | 1 | 1 | 1 | 0.3 | | 386 | 1 |
| 62720 | 1 | Oct. 18, 1956 | GU | 1 | U | 1 | 1 | 1 | 1 | 0.68 | 1 | >464 | 1 |

TABLE 15-continued

Documented sera from population I
42 Hp + sera

| No. of serum | Sex | Date of birth | Endos. | ANAMATOPATHOLOGY Giemsa | Histo | BACTERIOLOGY Gram | Urea | Cult. | Hp | JLF Sero | VS = 0.3 | NOG | VS = 60 |
|---|---|---|---|---|---|---|---|---|---|---|---|---|---|
| 67767 | 2 | Oct. 1, 1944 | GDU | 1 | U | 1 | 1 | 1 | 1 | 1.2 | 1 | >464 | 1 |
| 205855 | 1 | Jul. 9, 1938 | G, U | 1 | DU | 1 | 1 | 1 | 1 | 0.25 | | 71 | 1 |

Legend
G = Gastritis
H = Hiatus hernia
U = Ulcer
(DU = Duodenal ulcer)
(GU = Gastric ulcer)
D = Duodenitis
B/bulb = Bulbitis
O = Oesophagitis

TABLE 16

Documented sera from population I
55 Hp − sera

| No. of serum | Sex | Date of birth | Endos. | ANAMATOPATHOLOGY Giemsa | Histo | BACTERIOLOGY Gram | Urea | Cult. | Hp | JLF Sero | VS = 0.3 | NOG | VS = 60 |
|---|---|---|---|---|---|---|---|---|---|---|---|---|---|
| 79476 | 1 | Jun. 23, 1931 | G | 0 | Ulcerated adenoma | 0 | 0 | 0 | 0 | 0.02 | 0 | 6 | 0 |
| 75439 | 2 | May 14, 1932 | G | 0 | G | 0 | 0 | 0 | | 1.19 | | >464 | |
| 97286 | 2 | Jan. 3, 1937 | G | 0 | G | 0 | 0 | 0 | | 1.45 | | 66 | |
| 68053 | 1 | May 2, 1948 | G | 0 | G | 0 | 0 | 0 | | 1.02 | | 304 | |
| 71300 | 2 | Oct. 14, 1963 | G | 0 | G | 0 | 0 | 0 | | 0.89 | | >464 | |
| 944990 | 1 | Oct. 1, 1954 | G | 0 | G | 0 | 0 | 0 | 0 | 0.04 | 0 | 4 | 0 |
| 967659 | 2 | Jan. 28, 1946 | G | 0 | G | 0 | 0 | 0 | 0 | 0.01 | 0 | 5 | 0 |
| 985409 | 2 | Jul. 26, 1920 | min. U | 0 | G | 0 | 0 | 0 | | 0.21 | 0 | 69 | |
| 985551 | 2 | Aug. 18, 1909 | G, U, B | 0 | G | 0 | 0 | 0 | 0 | 0.05 | 0 | 14 | 0 |
| 992025 | 1 | Mar. 22, 1932 | G | 0 | G | 0 | 0 | 0 | | 0.07 | | 65 | |
| 998792 | 2 | Apr. 11, 1944 | G | 0 | G | 1* | 0 | 0 | 0 | 0.08 | 0 | 26 | 0 |
| 16479 | 1 | Jul. 13, 1993 | RAS | 0 | G | 0 | 0 | 0 | 0 | 0.02 | 0 | 0 | 0 |
| 77183 | 2 | Aug. 24, 1914 | G, U | 0 | G | 0 | 0 | 0 | 0 | 0.03 | 0 | 9 | 0 |
| 77566 | 1 | Jan. 25, 1932 | G | 0 | G | 0 | 0 | 0 | 0 | 0.01 | 0 | 22 | 0 |
| 991337 | 1 | Oct. 24, 1960 | G | 0 | G + hyperplasia | 0 | 0 | 0 | 0 | 0.07 | 0 | 26 | 0 |
| 78471 | 2 | Dec. 15, 1915 | G | 0 | G + intest. metapl. | 0 | 0 | 0 | | 0.07 | 0 | 106 | |
| 83356 | 1 | Jul. 10, 1921 | cicat. U | 0 | min. G | 0 | 0 | 0 | | 0.37 | | >464 | |
| 936515 | 2 | Jun. 5, 1981 | RAS | 0 | min. G | 0 | 0 | 0 | 0 | 0.2 | 0 | 0 | 0 |
| 991386 | 2 | Jan. 22, 1971 | G | 0 | min. G | 1* | 0 | 0 | 0 | 0.17 | 0 | 3 | 0 |
| 6130 | 1 | May 5, 1972 | G | 0 | min. G | 0 | 0 | 0 | 0 | 0.06 | 0 | 0 | 0 |
| 81415 | 1 | Aug. 23, 1931 | G | 0 | min. G | 0 | 0 | 0 | 0 | 0.03 | 0 | 5 | 0 |
| 82175 | 1 | Jan. 13, 1949 | cicat. U | 0 | min. G | 0 | 0 | 0 | 0 | 0.03 | 0 | 34 | 0 |
| 78652 | 1 | Aug. 1, 1918 | G, U | 0 | gast. hypotrophia | 0 | 0 | 0 | 0 | 0.04 | 0 | 10 | 0 |
| 89819 | 2 | Feb. 16, 1942 | Normal | 0 | Normal | 0 | 0 | 0 | | 0.88 | | >464 | |
| 942184 | 2 | Feb. 9, 1967 | G | 0 | Normal | 0 | 0 | 0 | 0 | 0.1 | 0 | 52 | 0 |
| 981000 | 2 | Oct. 10, 1947 | G | 0 | Normal | 0 | 0 | 0 | 0 | 0.06 | 0 | 19 | 0 |
| 1613 | 1 | Jan. 11, 1926 | G, B, D | 0 | Normal | 0 | 0 | 0 | | 0.68 | | 195 | |
| 984979 | 2 | Apr. 23, 1929 | GU | 0 | Normal | 0 | 0 | 0 | 0 | 0 | 0 | 3 | 0 |
| 58767 | 2 | Dec. 19, 1993 | RAS | 0 | Normal | 0 | 0 | 0 | 0 | 0.08 | 0 | 0 | 0 |
| 79861 | 2 | Jul. 26, 1963 | G, O | 0 | Normal | 0 | 0 | 0 | 0 | 0.06 | 0 | 16 | 0 |
| 85290 | 2 | Apr. 26, 1963 | RAS | 0 | Normal | 0 | 0 | 0 | 0 | 0.01 | 0 | 2 | 0 |
| 91423 | 1 | Feb. 13, 1939 | RAS | 0 | Normal | 0 | 0 | 0 | 0 | 0.03 | 0 | 0 | 0 |
| 93252 | 2 | Aug. 26, 1985 | RAS | 0 | Normal | 0 | 0 | 0 | 0 | 0.09 | 0 | 10 | 0 |
| 94430 | 1 | Apr. 6, 1962 | RAS | 0 | Normal | 0 | 0 | 0 | | 0.13 | 0 | >464 | |
| 990363 | 2 | Jun. 3, 1936 | G, B | 0 | Normal +/− | 0 | 0 | 0 | 0 | 0.18 | 0 | 42 | 0 |
| 87467 | 1 | Oct. 7, 1950 | GDU | 0 | U | 0 | 0 | 0 | 0 | 0.02 | 0 | 60 | 0 |
| 239085 | 1 | Feb. 5, 1945 | Bulb., GU | 0 | U | 0 | 0 | 0 | | 0.03 | 0 | 73 | |
| 3473 | 1 | Feb. 6, 1946 | G, U | 1 | G | 0 | 0 | 0 | | 1.01 | | >464 | |
| 78605 | 1 | May 14, 1983 | bulb. U | 1 | G | 0 | 0 | 0 | | 0.56 | | >464 | |
| 83721 | 1 | Jan. 21, 1995 | G | 1 | G | 0 | 0 | 0 | | 0.61 | | >245 | |
| 90169 | 1 | Apr. 18, 1938 | G, B | 1 | G | 0 | 0 | 0 | | 1.15 | | >464 | |
| 91081 | 2 | Jan. 8, 1945 | G, D | 1 | G | 0 | 0 | 0 | | 1.8 | | >464 | |
| 43127 | 1 | Feb. 24, 1941 | G | 1 | G | 0 | 0 | 0 | | 1.15 | | >464 | |
| 928133 | 2 | Mar. 25, 1971 | G | 1 | G | 0 | 0 | 0 | 0 | 0.03 | 0 | 3 | 0 |
| 9128 | 1 | Mar. 8, 1977 | G | 1 | G | 0 | 0 | 0 | 0 | 0.01 | 0 | 0 | 0 |
| 974895 | 1 | May 11, 1938 | B, G | 1 | G | 0 | 0 | 0 | 0 | 0.08 | 0 | 2 | 0 |

TABLE 16-continued

Documented sera from population I
55 Hp − sera

| No. of serum | Sex | Date of birth | Endos. | ANAMATOPATHOLOGY Giemsa | ANAMATOPATHOLOGY Histo | BACTERIOLOGY Gram | BACTERIOLOGY Urea | BACTERIOLOGY Cult. | BACTERIOLOGY Hp | JLF Sero | VS = 0.3 | NOG | VS = 60 |
|---|---|---|---|---|---|---|---|---|---|---|---|---|---|
| 26697 | 1 | Aug. 23, 1944 | H, O, U | 1 | G | 0 | 0 | 0 | 0 | 0.21 | 0 | 8 | 0 |
| 78414 | 1 | Feb. 6, 1921 | G, B, U | 1 | G | 0 | 0 | 0 | 0 | 0.02 | 0 | 5 | 0 |
| 78451 | 1 | Nov. 26, 1945 | G | 1 | G | 0 | 0 | 0 | 0 | 0.02 | 0 | 19 | 0 |
| 79500 | 1 | Mar. 1, 1950 | Oesoph. U | 1 | G | 0 | 0 | 0 | 0 | 0.01 | 0 | 3 | 0 |
| 79880 | 1 | Jan. 2, 1974 | GU, B | 1 | G | 0 | 0 | 0 | 0 | 0.06 | 0 | 5 | 0 |
| 416 | 1 | Feb. 18, 1971 | O, G | 1 | min G | 0 | 0 | 0 | 0 | 0.03 | 0 | 1 | 0 |
| 74548 | 1 | Feb. 25, 1945 | GDU | 1 | U | 0 | 0 | 0 | | 0.38 | | 371 | |
| 99538 | 1 | Apr. 2, 1958 | bulb. U | 1 | U | 0 | 0 | 0 | | 1.08 | | >464 | |
| 98953 | 2 | Dec. 19, 1916 | U | 1 | U | 0 | 0 | 0 | | 0.62 | | >464 | |

TABLE 17

Documented population from population I
55 Hp− sera
42 Hp+ sera

| | SENSITIVITY | SPECIFICITY |
|---|---|---|
| JLF sero | 85.7% (36/42) | 70.9% (39/55) |
| NOG 60 | 97.6% (41/42) | 61.8% (34/55) |

EXTRACTION PROTOCOLS USING THE AFLAGELLATE STRAIN N6flba-.

Quantity supplied: 800 mg of bacteria collected using PBS and centrifuged.

3 extractions tested.

| | EXTRACTIONS OF THE AFLAGELLATE STRAIN | | |
|---|---|---|---|
| | Glycine extraction | n-octyl glucoside extraction | PBS extraction |
| Recovery | PBS | 0.01M PBS | PHS, pH 7.4 |
| Washing | Twice in PBS; 8000 rpm/12 min | Twice in PBS; 8000 rpm/12 min | |
| Extraction | 0.2M acid glycine buffer, pH 2.2, for 15 min and at room temperature gentle agitation 100 mg (wet weight) per 2.5 ml | PBS containing: 1% n-octyl glucocide, pH 7.2 (Sigma Chemical Co.), for 20 min at room temperature | Vortex for 1 min. |
| Centrifugation | 11,000 g for 15 min | 23,500 g for 20 min | 5,000 g for 10 min |
| Neutralization | 1M NaOH | | |
| Dialysis | PBS, pH 7.2, for 24 h at +4° C. cut-off: 10,000 | PBS, pH 7.2, for 24 hours at +4° C. cut-off: 10,000 | PBS, pH 7.2, for 24 h at +4° C. cut-off: 10,000 |
| Storage | determination of the concentration storage at −20° C. | removal of the insoluble particles storage at −20° C. | determination of the concentration storage at −20° C. |

SDS PAGE ON DIFFERENT EXTRACTS OF THE AFLAGELLATE STRAIN N6 FLBA-

| Well No. | Sample Type | Concentration μg/ml | Sample volume/ buffer volume | Volume loaded |
|---|---|---|---|---|
| 1 | MW standard | | 5 + 5/190 | 10 |
| 2 | Glycine extract | 202.9 | 60/60 | 60 |
| 3 | | | | |
| 4 | n-octyl glucoside extract | 874 | 51/39 | 60 |
| 5 | | | | |
| 6 | PBS 1 extract | 539.2 | 60/20 | 60 |
| 7 | | | | |
| 8 | PBS 2 extract | 77.9 | 60/20 | 60 |
| 9 | | | | |
| 10 | MW standard | | 5 + 5/190 | 10 |
| 11 | Glycine extract pellet | 2778.7 | 20/20 | 20 |
| 12 | | | | |
| 13 | Glucoside extract pellet | 972.9 | 40/40 | 60 |
| 14 | | | | |
| 15 | Sedimented glycine extract | 309.3 | 60/20 | 60 |
| 16 | | | | |
| 17 | HspA Mal E | 3000 | 20/20 | 20 |
| 18 | | | | |
| 19 | | | | |
| 20 | Kaleidoscope | | | 20 |

REFERENCES

1. Andrews, G. P., Maurelli, A. T.: mxiA of *Shigella flexneri* 2a, which facilitates export of invasion plasmid antigens, encodes a homolog of the low-calcium-response protein LcrD of *Yersinia Pestis*. Infect. Immun. 60: 3287–3295 (1992).

2. Galan, J. E., Ginocchio, C. Cosleas, P.: Molecular and functional characterization of the *Salmonella* invasion gene invA: homology of InvA to members of a new protein family. J. Bacteriol. 174, 4338–4349 (1992.

3. Leying, H., Suerbaum, S. Geis, G., Haas, R.: Cloning and genetic characterization of a *Helicobacter pylori* flagellin gene. Mol. Microbiol. 6. 2563–2874 (1993).

5. O'Toole, P. W., Kostrzynska, M., Trust. T. J. : Nonmobile mutants of *Helicobacter pylori* and *Helicobacter muslelae* defective in flagellar hook production. Mol. Microbiol. 14, 691–703 (1994).

6. Plano, G. V., Barve, S. S., Straley, S. C.: LcrD, a membrane-bound regulator of the *Yersinia pestis* low-calcium response. J. Bacteriol. 173, 7293–7303 (1991).

7. Ramakrishnaan, G., Zhao, J-L., Newton A.: The cell cycle-regulated gene fibF of *Caulobacter crescentus* is homologous to a virulence locus of *Yersinia pestis*. J. Bacteriol. 173, 7283–7292 (1991).

8. Suerbaum. S., Josenhans. C., Labigne. A.: Cloning and genetic characterization of the *Helicobacter pylori* and *Helicobacter mustelae* flab flagellin genes and construction of *H. pylori* flaA- and flaB-negative mutants by electroporation-mediated allelic exchange. J. Bacteriol. 175, 3278–3288 (1993).

What is claimed is:

1. An *H. pylori* bacterial strain, or an extract of an *H. pylori* bacterial strain, wherein the *H. pylori* bacterial strain has an aflagellate phenotype resulting from a mutation in the flbA gene of the *H. pylori* bacterial strain.

2. The *H. pylori* bacterial strain, or extract of an *H. pylori* bacterial strain, according to claim 1, wherein the flbA gene is able to hybridize, under conditions of stringency, with a probe corresponding to a nucleotide fragment from *H. pylori*, which has been amplified using two oligonucleotides having the following sequences:

OLF1bA-1: ATGCCTCGAGGTCGAAAAGCAAGATG (SEQ ID NO:1).

OLF1bA-2: GAAATCTTCATACTGGCAGCTCC AGTC (SEQ ID NO:2).

3. The *H. pylori* bacterial strain, or extract of an *H. pylori* bacterial strain, according to claim 1, wherein the flbA gene comprises SEQ ID NO: 6.

4. The *H. pylori* bacterial strain, or extract of an *H. pylori* bactenal strain, according to claim 1, wherein the *H. pylori* bacterial strain does not express the hook protein (or anchoring protein) of the flagellum of *H. pylori*.

5. The *H. pylori* bacterial strain, or extract of an *H. pylori* bacterial strain, according to claim 1, wherein the *H. pylori* bacterial strain also lacks the flagellum sheath.

6. The *H. pylori* bacterial strain, or extract of an *H. pylori* bacterial strain, according to claim 5, wherein the *H. pylori* bacterial strain does not express the hook protein (or anchoring protein) of the flagellum of *H. pylori*.

7. The *H. pylori* bacterial strain, or extract of an *H. pylori* bacterial strain, according to claim 1, wherein the *H. pylori* bacterial strain is obtained from strain N6 having deposit Accession No. NCIMB 40512.

8. The *H. pylori* bacterial strain, or extract of an *H. pylori* bacterial strain, according to claim 1, wherein the *H. pylori* bacterial strain is strain N6flbA⁻ having deposit Accession No. NCIMB 40747.

9. The extract of an *H. pylori* bacterial strain according to claim 1, wherein the bacterial extract is a total bacterial extract.

10. The extract of an *H pylori* bacterial strain according to claim 1, wherein the bacterial extract is a n-octyl glucoside extract.

11. The extract of an *H. pylori* bacterial strain according to claim 1, wherein the bacterial extract is obtained after extracting with PBS or glycine.

12. An *H. pylori* bacterial strain, or an extract of an *H. pylori* bacterial strain, wherein the *H. pylori* bacterial strain has an aflagellate phenotype resulting from a mutation in the flbA gene of the *H. pylori* bacterial strain, and wherein the *H. pylori* bacterial strain does not express the FlaA and FlaB proteins.

13. The *H. pylori* bacterial strain, or extract of an *H. pylori* bacterial strain, according to claim 12, wherein the flbA gene is able to hybridize, under conditions of stringency, with a probe corresponding to a nucleotide fragment from *H. pylori*, which has been amplified using two oligonucleotides having the following sequences:

OLF1bA-1: ATGCCTCGAGGTCGAAAAGCAAGATG (SEQ ID NO:1),

OLF1bA-2: GAAATCTTCATACTGGCAGCTCC AGTC (SEQ ID NQ:2).

14. The *H. pylori* bacterial strain, or extract of an *H. pylori* bacterial strain, according to claim 12, wherein the flbA gene comprises SEQ ID NO:6.

15. The *H. pylori* bacterial strain, or extract of an *H. pylori* bacterial strain, according to claim 12, wherein the *H. pylori* bacterial strain does not express the hook protein (or anchoring protein) of the flagellum of *H. pylori*.

16. The *H. pylori* bacterial strain, or extract of an *H. pylori* bacterial strain, according to claim 12, wherein the *H. pylori* bacterial strain also lacks the flagellum sheath.

17. The *H. pylori* bacterial strain, or extract of an *H. pylori* bacterial strain, according to claim 16, wherein the *H. pylori* bacterial strain does not express the hook protein (or anchoring protein) of the flagellum of *H. pylori*.

18. The *H. pylori* bacterial strain, or extract of an *H. pylori* bacterial strain, according to claim 12, wherein the *H. pylori* bacterial strain is obtained from strain N6 having deposit Accession No. NCIMB 40512.

19. The *H. pylori* bacterial strain, or extract of an *H. pylori* bacterial strain, according to claim 12, wherein the *H. pylori* bacterial strain is strain N6flbA⁻ having deposit Accession No. NCIMB 40747.

20. The extract of an *H. pylori* bacterial strain according to claim 12, wherein the bacterial extract is a total bacterial extract.

21. The extract of an *H. pylori* bactenal strain according to claim 12, wherein the bacterial extract is a n-octyl glucoside extract.

22. The extract of an *H. pylori* bacterial strain according to claim 12, wherein the bacterial extract is obtained after extracting with PBS or glycine.

* * * * *

UNITED STATES PATENT AND TRADEMARK OFFICE
CERTIFICATE OF CORRECTION

PATENT NO. : 6,838,273 B2  Page 1 of 1
APPLICATION NO. : 09/015078
DATED : January 4, 2005
INVENTOR(S) : Suerbaum et al.

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by (184) days Delete the phrase "by 184" and insert --by 68 days--

Signed and Sealed this

Nineteenth Day of February, 2008

JON W. DUDAS
*Director of the United States Patent and Trademark Office*